(12) United States Patent
Smolke et al.

(10) Patent No.: US 9,315,862 B2
(45) Date of Patent: Apr. 19, 2016

(54) APTAMER REGULATED NUCLEIC ACIDS AND USES THEREOF

(75) Inventors: Christina D. Smolke, Pasadena, CA (US); Travis S. Bayer, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 584 days.

(21) Appl. No.: 11/243,889

(22) Filed: Oct. 5, 2005

(65) Prior Publication Data

US 2006/0088864 A1    Apr. 27, 2006

Related U.S. Application Data

(60) Provisional application No. 60/641,658, filed on Jan. 6, 2005, provisional application No. 60/615,977, filed on Oct. 5, 2004.

(51) Int. Cl.

| | | |
|---|---|---|
| *C12N 15/11* | (2006.01) | |
| *A61K 48/00* | (2006.01) | |
| *C07H 21/04* | (2006.01) | |
| *C12Q 1/68* | (2006.01) | |
| *C12N 15/113* | (2010.01) | |
| *C12N 15/115* | (2010.01) | |
| *C12N 15/63* | (2006.01) | |
| *A61K 38/00* | (2006.01) | |

(52) U.S. Cl.
CPC .............. *C12Q 1/686* (2013.01); *C12N 15/111* (2013.01); *C12N 15/113* (2013.01); *C12N 15/115* (2013.01); *C12N 15/635* (2013.01); *C12Q 1/6897* (2013.01); *A61K 38/00* (2013.01); *C12N 2310/11* (2013.01); *C12N 2310/111* (2013.01); *C12N 2310/14* (2013.01); *C12N 2310/16* (2013.01)

(58) Field of Classification Search
USPC .......................... 536/23.1, 24.5; 514/44; 435/6
See application file for complete search history.

(56) References Cited

U.S. PATENT DOCUMENTS

| | | |
|---|---|---|
| 4,235,871 A | 11/1980 | Papahadjopoulos et al. |
| 4,426,330 A | 1/1984 | Sears |
| 4,501,728 A | 2/1985 | Geho et al. |
| 4,534,899 A | 8/1985 | Sears |
| 4,737,323 A | 4/1988 | Martin et al. |
| 4,837,028 A | 6/1989 | Allen et al. |
| 4,897,355 A | 1/1990 | Eppstein et al. |
| 5,013,556 A | 5/1991 | Woodle |
| 5,013,830 A | 5/1991 | Ohtsuka et al. |
| 5,093,246 A | 3/1992 | Cech |
| 5,108,921 A | 4/1992 | Low |
| 5,176,996 A | 1/1993 | Hogan |
| 5,213,804 A | 5/1993 | Martin |
| 5,214,135 A | 5/1993 | Srivastava et al. |
| 5,227,170 A | 7/1993 | Sullivan |
| 5,256,775 A | 10/1993 | Froehler |
| 5,264,221 A | 11/1993 | Tagawa |
| 5,264,423 A | 11/1993 | Cohen et al. |
| 5,264,564 A | 11/1993 | Matteucci |
| 5,270,163 A | 12/1993 | Gold |
| 5,276,019 A | 1/1994 | Cohen et al. |
| 5,354,844 A | 10/1994 | Beug |
| 5,356,633 A | 10/1994 | Woodle |
| 5,395,619 A | 3/1995 | Zalipsky |
| 5,416,016 A | 5/1995 | Low |
| 5,417,978 A | 5/1995 | Tari |
| 5,459,127 A | 10/1995 | Felgner |
| 5,462,854 A | 10/1995 | Coassin |
| 5,469,854 A | 11/1995 | Unger |
| 5,500,357 A | 3/1996 | Taira et al. |
| 5,512,295 A | 4/1996 | Kornberg |
| 5,521,291 A | 5/1996 | Curiel |
| 5,525,719 A | 6/1996 | Srivastava et al. |
| 5,527,528 A | 6/1996 | Allen |
| 5,534,259 A | 7/1996 | Zalipsky |
| 5,543,152 A | 8/1996 | Webb |
| 5,543,158 A | 8/1996 | Gref |
| 5,547,932 A | 8/1996 | Curiel |
| 5,556,948 A | 9/1996 | Tagawa |
| 5,580,575 A | 12/1996 | Unger |
| 5,582,981 A | 12/1996 | Toole |
| 5,583,020 A | 12/1996 | Sullivan |
| 5,591,721 A | 1/1997 | Agrawal |
| 5,595,756 A | 1/1997 | Bally |
| 5,736,392 A | 4/1998 | Hawley-Nelson et al. |
| 5,756,291 A | 5/1998 | Griffin |
| 5,767,099 A | 6/1998 | Harris et al. |

(Continued)

FOREIGN PATENT DOCUMENTS

| | | |
|---|---|---|
| AU | 2004206255 B2 | 8/2008 |
| WO | WO 88/04300 | 6/1988 |

(Continued)

OTHER PUBLICATIONS

Vuyisich et al., Controlling protein activity with ligand-regulated RNA aptamers, 2002, Chemistry & Biology, vol. 9, pp. 907-913.*
Agrawal et al., RNA interference: biology, mechanism, and applications, 2003, Microbiology and Molecular Biology Reviews, vol. 67, pp. 657-685.*
Soukup et al., Nucleic acid molecular switches, 1999, Trends in Biotechnology, vol. 17, pp. 469-476.*
Carmell et al., RNase III enzymes and the initiation of gene silencing, 2004, Nature Structural & Molecular Biology, vol. 11, pp. 214-218.*
Tuleuova et al., Modulating endogenous gene expression of mammalian cells via RNA-small molecule interaction, 2008, BBRC, vol. 376, pp. 169-173.*
Buskirk et al., "Engineering a Ligand-Dependent RNA Transcriptional Activator," *Chemistry & Biology* 11:1157-1163 (2004).
Buskirk et al., "In Vivo Evolution of an RNA-Based Transcriptional Activator," *Chemistry & Biology* 10:533-540 (2003).

(Continued)

*Primary Examiner* — Dana Shin
(74) *Attorney, Agent, or Firm* — McCarter & English, LLP; Yu Lu

(57) ABSTRACT

The invention relates to trans-acting ligand-responsive nucleic acids and uses thereof. In particular, a ligand responsive nucleic acid comprises an effector domain and an aptamer domain that is responsive to a ligand.

20 Claims, 29 Drawing Sheets

(56) References Cited

U.S. PATENT DOCUMENTS

| | | | |
|---|---|---|---|
| 5,777,153 A | 7/1998 | Lin et al. | |
| 5,780,053 A | 7/1998 | Ashley et al. | |
| 5,830,430 A | 11/1998 | Unger et al. | |
| 5,830,653 A | 11/1998 | Froehler et al. | |
| 5,851,548 A | 12/1998 | Dattagupta et al. | |
| 5,855,910 A | 1/1999 | Ashley et al. | |
| 6,458,559 B1 * | 10/2002 | Shi et al. | 435/69.1 |
| 6,706,474 B1 | 3/2004 | Lu et al. | |
| 6,936,416 B2 * | 8/2005 | Zhu et al. | 435/5 |
| 6,951,720 B2 * | 10/2005 | Burgin et al. | 435/6.11 |
| 6,951,722 B2 * | 10/2005 | Mukai et al. | 435/6.1 |
| 6,953,688 B2 * | 10/2005 | Ferrick et al. | 435/320.1 |
| 6,958,215 B1 * | 10/2005 | Testa et al. | 435/6.13 |
| 2002/0106648 A1 | 8/2002 | Lizardi et al. | |
| 2002/0150996 A1 | 10/2002 | Nilsen-Hamilton | |
| 2002/0166132 A1 * | 11/2002 | Scherman et al. | 800/8 |
| 2003/0105051 A1 * | 6/2003 | McSwiggen | 514/44 |
| 2003/0124595 A1 | 7/2003 | Lizardi | |
| 2003/0157030 A1 | 8/2003 | Davis et al. | |
| 2004/0063654 A1 | 4/2004 | Davis | |
| 2004/0072785 A1 | 4/2004 | Wolff et al. | |
| 2004/0086884 A1 | 5/2004 | Beach | |
| 2004/0162235 A1 | 8/2004 | Trubetskoy et al. | |
| 2004/0204377 A1 | 10/2004 | Rana et al. | |
| 2005/0003362 A1 | 1/2005 | Crylov et al. | |
| 2005/0026286 A1 | 2/2005 | Chi et al. | |
| 2005/0037496 A1 | 2/2005 | Rozema et al. | |
| 2005/0042227 A1 | 2/2005 | Zankel et al. | |
| 2005/0048647 A1 * | 3/2005 | Taira et al. | 435/375 |
| 2005/0064595 A1 | 3/2005 | MacLachlan et al. | |
| 2005/0256071 A1 * | 11/2005 | Davis | 514/44 |
| 2005/0265957 A1 | 12/2005 | Monahan et al. | |
| 2006/0008910 A1 | 1/2006 | MacLachlan et al. | |
| 2006/0088864 A1 | 4/2006 | Smolke et al. | |
| 2006/0105975 A1 * | 5/2006 | Pendergrast et al. | 514/44 |
| 2006/0121510 A1 | 6/2006 | Breaker et al. | |
| 2006/0172925 A1 * | 8/2006 | Gorenstein et al. | 514/8 |
| 2006/0178327 A1 | 8/2006 | Yeung et al. | |
| 2006/0240093 A1 | 10/2006 | MacLachlan et al. | |
| 2007/0077571 A1 | 4/2007 | Ellington | |
| 2007/0083947 A1 * | 4/2007 | Huang et al. | 800/278 |
| 2007/0231392 A1 | 10/2007 | Wagner et al. | |
| 2008/0038296 A1 | 2/2008 | Brahmbhatt et al. | |
| 2008/0107694 A1 | 5/2008 | Trogden et al. | |
| 2008/0112916 A1 | 5/2008 | Wagner et al. | |
| 2008/0152661 A1 | 6/2008 | Rozema et al. | |
| 2009/0082217 A1 | 3/2009 | Smolke et al. | |
| 2009/0098561 A1 | 4/2009 | Smolke et al. | |
| 2009/0143327 A1 | 6/2009 | Smolke et al. | |
| 2009/0234109 A1 | 9/2009 | Han et al. | |
| 2010/0226901 A1 | 9/2010 | Smolke et al. | |
| 2010/0255545 A1 | 10/2010 | Smolke et al. | |
| 2011/0002892 A1 | 1/2011 | Galloway et al. | |
| 2012/0165387 A1 | 6/2012 | Smolke et al. | |

FOREIGN PATENT DOCUMENTS

| | | |
|---|---|---|
| WO | WO 88/09810 | 12/1988 |
| WO | WO 89/10134 | 11/1989 |
| WO | WO 90/11364 | 10/1990 |
| WO | WO 90/14074 A1 | 11/1990 |
| WO | WO 91/16024 A1 | 10/1991 |
| WO | WO 91/17424 A1 | 11/1991 |
| WO | WO 92/03568 A1 | 3/1992 |
| WO | WO 97/42317 | 11/1997 |
| WO | WO 98/13526 A1 | 4/1998 |
| WO | WO 9904800 | 2/1999 |
| WO | WO 99/27133 | 6/1999 |
| WO | WO 99/54506 | 10/1999 |
| WO | WO 00/20040 | 4/2000 |
| WO | WO 2004033653 A2 * | 4/2004 |
| WO | WO 2004/048545 A2 | 6/2004 |
| WO | WO 2004/065601 A2 | 8/2004 |
| WO | WO 2005001039 A2 * | 1/2005 |
| WO | WO 2005111238 A2 * | 11/2005 |
| WO | WO 2006086669 | 8/2006 |
| WO | WO 2007/089607 A2 | 8/2007 |
| WO | WO 2008/036825 A2 | 3/2008 |
| WO | WO 2008/058291 | 5/2008 |

OTHER PUBLICATIONS

Famulok, "Bringing Picomolar Protein Detection Into Proximity," *Nature Biotechnology* 20:448-449 (2002).
Fredriksson et al., "Protein Detection Using Proximity-Dependent DNA Litagation Assays," *Nature Biotechnology* 20:473-477 (2002).
Hesselberth et al., "Simultaneous Detection of Diverse Analytes with an Aptazyme Ligase Array," *Analytical Biochemistry* 312:106-112 (2003).
Luzi et al., "New Trends in Affinity Sensing: Aptamers for Ligand Binding," *Trends in Analytical Chemistry* 22:810-818 (2003).
Nutiu et al., "Structure-Switching Signaling Aptamers: Transducing Molecular Recognition Into Fluorescence Signaling," *Chem. Eur. J.* 10:1866-1876 (2004).
Nutiu et al., "Structure-Switching Signaling Aptamers," *J. Am. Chem. Soc.* 125:4771-4778 (2003).
Silverman, "Rube Goldberg Goes (RIBO)Nuclear? Molecular Switches and Sensors Made From RNA," *RNA* 9:377-383 (2003).
Winkler et al., "An MRNA Structure That Controls Gene Expression by Binding FMN," *PNAS* 99:15908-15913 (2002).
Winkler et al., "Genetic Control by Metabolite-Binding Riboswitches," *ChemBioChem* 4:1024-1032 (2003).
Al-Douahji et al., "The cyclin kinase inhibitor p21$^{WAF1-CIP1}$ is required for glomerular hypertrophy in experimental diabetic nephropathy," *Kidney Int* 56:1691-1699 (1999).
Banerjee et al., "Control of developmental timing by small temporal RNAs: a paradigm for RNA-mediated regulation of gene expression," *Bioessays* 24:119-129 (2002).
Barrick et al., "New RNA motifs suggest an expanded scope for riboswitches in bacterial genetic control," *Proc Natl Acad Sci USA* 101:6421-6426 (2004).
Bartel, "MicroRNAs: genomics, biogenesis, mechanism, and function," *Cell* 116:281-297 (2004).
Batzer et al., "Enhanced evolutionary PCR using oligonucleotides with inosine at the 3'-terminus," *Nucleic Acids Res* 19:5081 (1991).
Bayer et al., "Programmable ligand-controlled riboregulators of eukaryotic gene expression," *Nat Biotechnol* 23:337-343 (2005).
Been and Cech, "One binding site determines sequence specificity of Tetrahymena pre-rRNA self-splicing, trans-splicing, and RNA enzyme activity," *Cell* 47:207-216 (1986).
Benoist et al., "In vivo sequence requirements of the SV40 early promotor region," *Nature* 290:304-310 (1981).
Berens et al., "A tetracycline-binding RNA aptamer," *Bioorg Med Chem* 9:2549-2556 (2001).
Blind et al., "Cytoplasmic RNA modulators of an inside-out signal-transduction cascade," *Proc Natl Acad Sci USA* 96:3606-3610 (1999).
Brennecke et al., "Towards a complete description of the microRNA complement of animal genomes," *Genome Biol* 4:228.1-228.3 (2003).
Brinster et al., "Regulation of metallothionein-thymidine kinase fusion plasmids injected into mouse eggs," *Nature* 296:39-42 (1982).
Brummelkamp et al., "A system for stable expression of short interfering RNAs in mammalian cells," *Science* 296:550-553 (2002).
Buskirk et al., "Engineering a ligand-dependent RNA transcriptional activator," *Chem Biol* 11:1157-1163(2004).
Caplen et al., "Specific inhibition of gene expression by small double-stranded RNAs in invertebrate and vertebrate systems," *Proc Natl Acad Sci USA* 98:9742-9747 (2001).
Caponigro et al., "A small segment of the MATα1 transcript promotes mRNA decay in *Saccharomyces cerevisiae*: a stimulatory role for rare codons," *Mol Cell Biol* 13:5141-5148 (1993).
Chen et al., "Synthesis of oligodeoxyribonucleotide N3'→P5' phosphoramidates," *Nucleic Acids Res* 23:2661-2668 (1995).
Cox et al., "Automated selection of aptamers against protein targets translated in vitro: from gene to aptamer," *Nucleic Acids Res* 30:e108 (2002).

(56) References Cited

OTHER PUBLICATIONS

Dragun et al., "Inhibition of intercellular adhesion molecule-1 with antisense deoxynucleotides prolongs renal isograft survival in the rat," *Kidney Int* 54:2113-2122 (1998).
Dragun et al., "ICAM-1 antisense oligodesoxynucleotides prevent reperfusion injury and enhance immediate graft function in renal transplantation," *Kidney Int* 54:590-602 (1998).
Egholm et al., "PNA hybridizes to complementary oligonucleotides obeying the Watson-Crick hydrogen-bonding rules," *Nature* 365:566-568 (1993).
Elbashir et al., "Duplexes of 21-nucleotide RNAs mediate RNA interference in cultured mammalian cells," *Nature* 411:494-498 (2001).
Ellington et al., "In vitro selection of RNA molecules that bind specific ligands," *Nature* 346:818-822 (1990).
Famulok, "Oligonucleotide aptamers that recognize small molecules," *Curr Opin Struct Biol* 9:324-329 (1999).
Gardner et al., "Inferring genetic networks and identifying compound mode of action via expression profiling," *Science* 301:102-105 (2003).
Gautier et al., "α-DNA. IV: α-anomeric and β-anomeric tetrathymidylates covalently linked to intercalating oxazolopyridocarbazole. Synthesis, physicochemical properties and poly (rA) binding," *Nucleic Acids Res* 15:6625-6641 (1987).
Gil et al., "Induction of apoptosis by the dsRNA-dependent protein kinase (PKR): mechanism of action," *Apoptosis* 5:107-114 (2000).
Good, "Diverse antisense mechanisms and applications," *Cell Mol Life Sci* 60:823-824 (2003).
Good, "Translation repression by antisense sequences," *Cell Mol Life Sci* 60:854-861 (2003).
Gouda et al., "Free energy calculations for theophylline binding to an RNA aptamer: Comparison of MM-PBSA and thermodynamic integration methods," *Biopolymers* 68:16-34 (2003).
Haller et al., "Antisense oligonucleotides for ICAM-1 attenuate reperfusion injury and renal failure in the rat," *Kidney Int* 50:473-480 (1996).
Hamm et al., "Anti-idiotype RNA selected with an anti-nuclear export signal antibody is actively transported in oocytes and inhibits Rev- and cap-dependent RNA export," *Proc Natl Acad Sci USA* 94:12839-12844 (1997).
Haseloff et al., "Simple RNA enzymes with new and highly specific endoribonuclease activities," *Nature* 334:585-591 (1988).
Heidenreich et al., "RNase H-independent antisense activity of oligonucleotide N3'→P5' phosphoramidates," *Nucleic Acids Res* 25:776-780 (1997).
Hermann et al., "Adaptive recognition by nucleic acid aptamers," *Science* 287:820-825 (2000).
Hesselberth et al., "Simultaneous detection of diverse analytes with an aptazyme ligase array," *Anal Biochem* 312:106-112 (2003).
Hirschbein et al., "31P NMR spectroscopy in oligonucleotide research and development," *Antisense Nucleic Acid Drug Dev* 7:55-61 (1997).
Huizenga et al., "A DNA aptamer that binds adenosine and ATP," *Biochemistry* 34:656-665 (1995).
Inoue et al., "Sequence-dependent hydrolysis of RNA using modified oligonucleotide splints and RNase H," *FEBS Lett* 215:327-330 (1987).
Inoue et al., "Synthesis and hybridization studies on two complementary nona(2'-O-methyl)ribonucleotides," *Nucleic Acids Res* 15:6131-6148 (1987).
Isaacs et al., "Engineered riboregulators enable post-transcriptional control of gene expression," *Nat Biotechnol* 22:841-847 (2004).
Jhaveri et al., "In vitro selection of signaling aptamers," *Nat Biotechnol* 18:1293-1297 (2000).
Jose et al., "Cooperative binding of effectors by an allosteric ribozyme," *Nucleic Acids Res* 29:1631-1637 (2001).
Kertsburg et al., "A versatile communication module for controlling RNA folding and catalysis," *Nucleic Acids Res* 30:4599-4606 (2002).
Khosla et al., "Metabolic engineering for drug discovery and development," *Nat Rev Drug Discov* 2:1019-1025 (2003).

Kim, "Small RNAs: classification, biogenesis, and function," *Mol Cells* 19:1-15 (2005).
Kipshidze et al., "Local delivery of c-myc neutrally charged antisense oligonucleotides with transport catheter inhibits myointimal hyperplasia and positively affects vascular remodeling in the rabbit balloon injury model," *Catheter Cardiovasc Interv* 54:247-256 (2001).
Kipshidze et al., "Intramural coronary delivery of advanced antisense oligonucleotides reduces neointimal formation in the porcine stent restenosis model," *J Am Coll Cardiol* 39:1686-1691 (2002).
Kobayashi et al., "Programmable cells: interfacing natural and engineered gene networks," *Proc Natl Acad Sci USA* 101:8414-8419 (2004).
Koch, "The metabolism of methylpurines by *Escherichia coli*. I. Tracer studies," *J Biol Chem* 219:181-188 (1956).
Koizumi et al., "Allosteric selection of ribozymes that respond to the second messengers cGMP and cAMP," *Nat Struct Biol* 6:1062-1071 (1999).
Kramer et al., "Role for antisense RNA in regulating circadian clock function in Neurospora crassa," *Nature* 421:948-952 (2003).
Kutryk et al., "Local intracoronary administration of antisense oligonucleotide against c-myc for the prevention of in-stent restenosis: results of the randomized investigation by the Thoraxcenter of antisense DNA using local delivery and IVUS after coronary stenting (ITALICS) trial," *J Am Coll Cardiol* 39:281-287 (2002).
Kuwabara et al., "Allosterically controllable ribozymes with biosensor functions," *Curr Opin Chem Biol* 4:669-677 (2000).
Kuwabara et al., "Allosterically controllable maxizyme-mediated suppression of progression of leukemia in mice," *Biomacromolecules* 2:1220-1228 (2001).
Kuwabara et al., "Allosterically controlled single-chained maxizymes with extremely high and specific activity," *Biomacromolecules* 2:788-799 (2001).
Lavorgna et al., "In search of antisense," *Trends Biochem Sci* 29:88-94 (2004).
Lemaitre et al., "Specific antiviral activity of a poly(L-lysine)-conjugated oligodeoxyribonucleotide sequence complementary to vesicular stomatitis virus N protein mRNA initiation site," *Proc Natl Acad Sci USA* 84:648-652 (1987).
Letsinger et al., "Cholesteryl-conjugated oligonucleotides: synthesis, properties, and activity as inhibitors of replication of human immunodeficiency virus in cell culture," *Proc Natl Acad Sci USA* 86:6553-6556 (1989).
Lilley, "The origins of RNA catalysis in ribozymes," *Trends Biochem Sci* 28:495-501 (2003).
Lorsch et al., "In vitro selection of RNA aptamers specific for cyanocobalamin," *Biochemistry* 33:973-982 (1994).
Mandal et al., "Adenine riboswitches and gene activation by disruption of a transcription terminator," *Nat Struct Mol Biol* 11:29-35 (2004).
Mannironi et al., "In vitro selection of dopamine RNA ligands," *Biochemistry* 36:9726-9734 (1997).
Mateus et al., "Destabilized green fluorescent protein for monitoring dynamic changes in yeast gene expression with flow cytometry," *Yeast* 16:1313-1323 (2000).
Mathews et al., "Incorporating chemical modification constraints into a dynamic programming algorithm for prediction of RNA secondary structure," *Proc Natl Acad Sci USA* 101:7287-7292 (2004).
McCaffrey et al., "RNA interference in adult mice," *Nature* 418:38-39 (2002).
McManus et al., "Gene silencing using micro-RNA designed hairpins," *RNA* 8:842-850 (2002).
Nagai et al., "A variant of yellow fluorescent protein with fast and efficient maturation for cell-biological applications," *Nat Biotechnol* 20:87-90 (2002).
Nutiu et al., "Structure-switching signaling aptamers," *J Am Chem Soc* 125:4771-4778 (2003).
Ohtsuka et al., "An alternative approach to deoxyoligonucleotides as hybridization probes by insertion of deoxyinosine at ambiguous codon positions," *J Biol Chem* 260:2605-2608 (1985).
Paddison et al., "Stable suppression of gene expression by RNAi in mammalian cells," *Proc Natl Acad Sci USA* 99:1443-1448 (2002).

(56) References Cited

OTHER PUBLICATIONS

Paddison et al., "Short hairpin RNAs (shRNAs) induce sequence-specific silencing in mammalian cells," *Genes Dev* 16:948-958 (2002).
Perry-O'Keefe et al., "Peptide nucleic acid pre-gel hybridization: an alternative to Southern hybridization," *Proc Natl Acad Sci USA* 93:14670-14675 (1996).
Piganeau et al., "In vitro selection of allosteric ribozymes: theory and experimental validation," *J Mol Biol* 312:1177-1190 (2001).
Robertson et al., "Design and optimization of effector-activated ribozyme ligases," *Nucleic Acids Res* 28:1751-1759 (2000).
Rossolini et al., "Use of deoxyinosine-containing primers vs degenerate primers for polymerase chain reaction based on ambiguous sequence information," *Moll Cell Probes* 8:91-98 (1994).
Roth et al., "Selection in vitro of allosteric ribozymes," *Methods Mol Biol* 252:145-164 (2004).
Samarsky et al., "A small nucleolar RNA:ribozyme hybrid cleaves a nucleolar RNA target in vivo with near-perfect efficiency," *Proc Natl Acad Sci USA* 96:6609-6614 (1999).
Sarver et al., "Ribozymes as potential anti-HIV-1 therapeutic agents," *Science* 247:1222-1225 (1990).
Scherer et al., "Recent applications of RNAi in mammalian systems," *Curr Pharm Biotechnol* 5:355-360 (2004).
Scherer et al., "Approaches for the sequence-specific knockdown of mRNA," *Nat Biotechnol* 21:1457-1465 (2003).
Smolke et al., "Coordinated, differential expression of two genes through directed mRNA cleavage and stabilization by secondary structures," *Appl Environ Microbiol* 66:5399-5405 (2000).
Soukup et al., "Altering molecular recognition of RNA aptamers by allosteric selection," *J Mol Biol* 298:623-632 (2000).
Soukup et al., "Generating new ligand-binding RNAs by affinity maturation and disintegration of allosteric ribozymes," *RNA* 7:524-536 (2001).
Soukup et al., "Design of allosteric hammerhead ribozymes activated by ligand-induced structure stabilization," *Structure* 7:783-791 (1999).
Stein et al., "Oligodeoxynucleotides as inhibitors of gene expression: a review," *Cancer Res* 48:2659-2668 (1988).
Stojanovic et al., "Modular aptameric sensors," *J Am Chem Soc* 126:9266-9270 (2004).
Sui et al., "A DNA vector-based RNAi technology to suppress gene expression in mammalian cells," *Proc Natl Acad Sci USA* 99:5515-5520 (2002).
Taira et al., "Construction of a novel RNA-transcript-trimming plasmid which can be used both in vitro in place of run-off and (G)-free transcriptions and in vivo as multi-sequences transcription vectors," *Nucleic Acids Res* 19:5125-5130 (1991).
Tang et al., "Rational design of allosteric ribozymes," *Chem Biol* 4:453-459 (1997).
Tuerk et al., "Systematic evolution of ligands by exponential enrichment: RNA ligands to bacteriophage T4 DNA polymerase," *Science* 249:505-510 (1990).
Vacek et al., "Antisense-mediated redirection of mRNA splicing," *Cell Mol Life Sci* 60:825-833 (2003).
van der Krol et al., "Modulation of eukaryotic gene expression by complementary RNA or DNA sequences," *Biotechniques* 6:958-976 (1988).
Wagner et al., "Nucleotide sequence of the thymidine kinase gene of herpes simplex virus type 1," *Proc Natl Acad Sci USA* 78:1441-1445 (1981).
Wagner, "Gene inhibition using antisense oligodeoxynucleotides," *Nature* 372:333-335 (1994).
Wang et al., "A general approach for the use of oligonucleotide effectors to regulate the catalysis of RNA-cleaving ribozymes and DNAzymes," *Nucleic Acids Res* 30:1735-1742 (2002).
Wang et al., "A general strategy for effector-mediated control of RNA-cleaving ribozymes and DNA enzymes," *J Mol Biol* 318:33-43 (2002).
Watkins et al., "Metabolomics and biochemical profiling in drug discovery and development," *Curr Opin Mol Ther* 4:224-228 (2002).

Weiss et al., "Antisense RNA gene therapy for studying and modulating biological processes," *Cell Mol Life Sci* 55:334-358 (1999).
Werstuck et al., "Controlling gene expression in living cells through small molecule-RNA interactions," *Science* 282:296-298 (1998).
Wilda et al., "Killing of leukemic cells with a BCR/ABL fusion gene by RNA interference (RNAi)," *Oncogene* 21:5716-5724 (2002).
Wilson et al., "The interaction of intercalators and groove-binding agents with DNA triple-helical structures: the influence of ligand structure, DNA backbone modifications and sequence," *J Mol Recognit* 7:89-98 (1994).
Winkler et al., "Control of gene expression by a natural metabolite-responsive ribozyme," *Nature* 428:281-286 (2004).
Winkler et al., "Thiamine derivatives bind messenger RNAs directly to regulate bacterial gene expression," *Nature* 419:952-956 (2002).
Yamamoto et al., "Identification of a functional promoter in the long terminal repeat of Rous sarcoma virus," *Cell* 22:787-797 (1980).
Yelin et al., "Widespread occurrence of antisense transcrip ion in the human genome," *Nat Biotechnol* 21:379-386 (2003).
Yen et al., "Exogenous control of mammalian gene expression through modulation of RNA self-cleavage," *Nature* 431:471-476 (2004).
Yu et al., "RNA interference by expression of short-interfering RNAs and hairpin RNAs in mammalian cells," *Proc Natl Acad Sci USA* 99:6047-6052 (2002).
Zaug et al., "A labile phosphodiester bond at the ligation junction in a circular intervening sequence RNA," *Science* 224:574-578 (1984).
Zaug et al., "The intervening sequence RNA of Tetrahymena is an enzyme," *Science* 231:470-475 (1986).
Zaug et al., "The Tetrahymena ribozyme acts like an RNA restriction endonuclease," *Nature* 324:429-433 (1986).
Zimmermann et al., "Interlocking structural motifs mediate molecular discrimination by a theophylline-binding RNA," *Nat Struct Biol* 4:644-649 (1997).
Zimmermann et al., "Molecular interactions and metal binding in the theophylline-binding core of an RNA aptamer," *RNA* 6:659-667 (2000).
Zon, "Oligonucleotide analogues as potential chemotherapeutic agents," *Pharm Res* 5:539-549 (1988).
Beisel et al., "Model-guided design of ligand-regulated RNAi for programmable control of gene expression," 2008 Molecular Systems Biology 4:224.
Chen et al., "Genetic control of mammalian T-cell proliferation with synthetic RNA regulatory systems." 2010 Proc. Natl. Acad. Sci. USA. 107: 8531-6.
Culler et al., "Functional selection and systematic analysis of intronic splicing elements identifies active sequence motifs and associated splicing factors." 2010 Nuc. Acids Res. 38: 5152-65.
Hoff et al., "In vivo fluorescent detection of Fe-S clusters coordinated by human GRX2." 2009 Chem. Biol. 16: 1299-308.
Smolke, "Building outside of the box: iGEM and the BioBricks Foundation." 2009 Nat. Biotech. 27:1099-102.
Smolke, "It's the DNA that counts." 2009 Science. 324: 1156-7.
Beisel et al., "Design principles for riboswitch function." 2009 PLoS Comp. Biol. 5: e1000363.
Win et al., "Frameworks for programming biological function through RNA parts and devices." 2009 Chem. Biol. 16: 298-310.
Bayer et al., "Synthetic control of a fitness tradeoff in yeast nitrogen metabolism." 2009 J. Biol. Eng. 3: 1.
Hoff et al., "Fluorescence detection of a protein-bound 2Fe2S cluster." 2009 Chembiochem. 10: 667-70.
Hawkins et al., "Production of benzylisoquinoline alkaloids in *Saccharomyces cerevisiae*." 2008 Nat. Chem. Biol. 4: 564-73.
Benenson, "Small hairpin RNA as a small molecule sensor." 2008 Mol. Sys. Biol. 4: 227.
Keasling, "From yeast to alkaloids." 2008 Nat. Chem. Biol. 4: 524-5.
Win et al., "Higher-order cellular information processing with synthetic RNA devices." 2008 Science. 322: 456-60.
Shapiro et al., "RNA computing in a living cell." 2008 Science. 322: 387-8.
Baker et al., "Engineering life: building a Fab for biology." 2006 Scientific American. 294: 44-51.

(56) References Cited

OTHER PUBLICATIONS

Win et al., "Codeine-binding RNA aptamers and rapid determination of their binding constants using a direct coupling surface plasmon resonance assay." 2006 Nuc. Acids Res. 34: 5670-82.
Pfleger et al., "Combinatorial engineering of intergenic regions in operons tunes expression of multiple genes." 2006 Nat. Biotech. 24: 1027-32.
Hawkins et al., "The regulatory roles of the galactose permease and kinase in the induction response of the GAL network in *Saccharomyces cerevisiae*." 2006 J. Biol. Chem. 281: 13485-92.
Isaacs et al., "Plug and play with RNA." 2005 Nat. Biotech. 23: 306-7.
Martin et al., "Redesigning cells for the production of complex organic molecules." 2002 ASM News 68: 336-43.
Smolke et al., "Effect of gene location, mRNA secondary structures, and Rnase sites on expression of two genes in an engineered operon." 2002 Biotech. Bioeng. 80: 762-76.
Smolke et al., "Effect of copy number and mRNA processing and stabilization on transcript and protein levels from an engineered dual-gene operon." 2002 Biotech. Bioeng. 78: 412-24.
Smolke et al., "Effects of transcription induction homogeneity and transcript stability on expression of two genes in a constructed operon." 2001 Appl. Micro. Biotech. 57: 689-96.
Smolke et al., "Controlling the metabolic flux through the carotenoid pathway using directed mRNA processing and stabilization." 2001 Met. Eng. 3: 313-21.
U.S. Appl. No. 12/218,628, filed Mar. 26, 2009, Christina D. Smolke.
An et al., Artificial control of gene expression in mammalian cells by modulating RNA interference through aptamer-small molecule interaction, 2006, RNA 12(5):710-716.
Bauer G. et al., Engineered riboswitches as novel tools in molecular biology, 2006, Journal of Biotechnology 124(1):4-11.
Berezovski et al., Nonequilibrium Capillary Electrophoresis of Equilibrium Mixtures: A Universal Tool for Development of Aptamers, 2005, J. Am. Chem. Soc. 127:3165-3171.
Davidson et al., Synthetic RNA circuits, 2007, Nature Chemical Biology 3(1):23-28.
Desai et al., Genetic screens and selections for small molecules based on a synthetic riboswitch that activates protein translation. 2004, Journal of the American Chemical Society 126:13247-13254.
Drabovich et al., Selection of Smart Aptamers by Equilibrium Capillary Electrophoresis of Eauilibrium Mixtures (ECEEM). 2005 J. Am. Chem. Soc. 127:11224-11225.
Isaacs et al., RNA synthetic biology. 2006 Nature Biotechnology 24(5):545-554.
John J. Rossi, Targeted cleavage: Tuneable cis-cleaving ribozymes. 2007 PNAS 104(38):14881-14882.
Mendonsa et al., In Vito Evolution of Functional DNA Using Capillary Electrophoresis. 2004 J. Am. Chem. Soc. 126:20-21.
Mendonsa et al., In Vitro Selection of Aptamers with Affinity for Neuropeptide Y Using D Capillary Electrophoresis. 2005 J. Am. Chem. Soc. 127:9382-9383.
Mendonsa et al., In Vitro Selection of High-Affinity DNA Ligands for Human IgE Using Capillary Electrophoresis. 2004 Anal. Chern. 76:5387-5392.
Smolke et al., Molecular Switches for Cellular Sensors. 2005 Engineering & Science 67(4):28-37.
Sudarsan et al., Tandem riboswitch architectures exhibit complex gene control functions. 2006 Science 314(5797):300-304.
Suess et al., A theophylline responsive riboswitch based on helix slipping contois gene expression in vivo. 2004 Nucleic Acids Research. 32(4):1610-1614.
Win et al., A modular and extensible RNA-based gene-regulartory platform for engineering cellular function. 2007 PNAS 104(36):14283-14288.
Win et al., RNA as a Versatile and Powerful Platform for Engineering Genetic Regulatory Tools. 2007 Biotechnoloay and Genetic Engineerinq Reviews 24:311-346.

Berens et al., Synthetic riboregulators—an alternative means to control gene expression. 2005 Gene Therapy and Molecular Biology 9:417-422.
Yokobayashi et al., Directed evolution of a genetic circuit. 2002 Proc Natl Acad Sci USA 99:16587-16591.
Basu et al., Spatiotemporal control of gene expression with pulse-generating networks. 2004 Proc Natl Acad Sci USA 101:6355-6360.
Levine et al., Quantitative Characteristics of Gene Regulation by Small RNA. 2007 PLoS Biol 5(e229):1998-2010.
Hebert et al., Loss of microRNA cluster miR-29a/b-1 in sporadic Alzheimer's disease correlates with increased BACE1/13-secretase expression. 2008 Proc Natl Acad Sci USA 105:6415-6420.
Calin et al., MiR-15a and miR-16-1 cluster functions in human leukemia. 2008 Proc Natl Acad Sci USA 105:5166-5171.
Ventura et al., Targeted Deletion Reveals Essential and Overlapping Functions of the miR17~92 Family of miRNA Clusters. 2008 Cell 132:875-886.
Welz et al., Ligand binding and gene control characteristics of tandem riboswitches in Bacillus anthracis. 2007 RNA 13:573.
Rodionov et al., Reconstruction of regulatory and metabolic pathways in metal-reducing δ-proteobacteria. 2004 Genome Biol 5:R90. 1-R90.27.
Rinaudo et al., A universal RNAi-based logic evaluator that operates in mammalian cells. 2007 Nat Biotechnol 25:795-801.
Deans et al., A Tunable Genetic Switch Based on RNAi and Repressor Proteins for Regulating Gene Expression in Mammalian Cells. 2007 Cell 130:363-372.
Berge et al., Pharmaceutical Salts. 1977 J. of Pharm Sci. 66:1-19.
Guet et al., Combinatorial synthesis of genetic networks. 2002 Science 296:1466-1470.
Kramer et al., BioLogic gates enable logical transcription control in mammalian cells. 2004 Biotechnol Bioeng 87:478-484.
Cox et al., Programming gene expression with combinatorial promoters. 2007 Mol Syst Biol 3:145.
Anderson et al., Environmental signal integration by a modular AND gate. 2007 Mol Syst Biol 3:133.
Seelig et al., Enzyme-Free Nucleic Acid Logic Circuits. 2006 Science 314:1585-1588.
Benenson et al., an autonomous molecular computer for logical control of gene expression. 2004 Nature 429:423-429.
Dirks et al., Triggered amplification by hybridization chain reaction. 2004 Proc Natl Acad Sci USA 101:15275-15278.
Stojanovic et al., A deoxyribozyme-based molecular automaton. 2003 Nat Biotechnol 21:1069-1074.
Penchovsky et al., Computational design and experimental validation of oligonucleotide-sensing allosteric ribozymes. 2005 Nat Biotechnol 23:1424-1433.
Breaker, Engineered allosteric ribozymes as biosensor components. 2002 Curr Opin Biotechnol 13:31-39.
Robertson et al., In vitro selection of an allosteric ribozyme that transduces analytes to amplicons. 1999 Nat Biotechnol 17:62-66.
Suess et al., Engineered riboswitches: overview, problems and trends. 2008 RNA Biol 5(1):1-6.
Brown et al., Endogenous microRNA can be broadly exploited to regulate transgene expression according to tissue, lineage and differentiation state. 2007 Nat Biotechnol 25:1457-1467.
Parisien et al., The MC-Fold and MC-Sym pipeline infers RNA structure from sequence data. 2008 Nature 452:51-55.
Mathews et al., Prediction of RNA secondary structure by free energy minimization. 2006 Curr Opin Struct Biol 16:270-278.
Khvorova et al., Sequence elements outside the hammerhead ribozyme catalytic core enable intracellular activity. 2003 Nat Struct Bioi 10:708-872.
Mandal et al., A glycine-dependent riboswitch that uses cooperative binding to control gene expression. 2004 Science 306:275-279.
Woodside et al., Nanomechanical measurements of the sequence-dependent folding landscapes of single nucleic acid hairpins. 2006 Proc Natl Acad Sci USA 103:6190-6195.
Stein et al., Physicochemical properties of phosphorothioate oligodeoxynucleotides. 1988 Nucl. Acids Res. 16:3209-3221.
Sarin et al., Inhibition of acquired immunodeficiency syndrome virus by oligodeoxynucleoside methylphosphonates. 1988 Proc. Natl. Acad. Sci. USA 85:7448-7451.

(56) References Cited

OTHER PUBLICATIONS

MacRae et al., Structural Basis for Double-Stranded RNA Processing by Dicer. 2006 Science 311( 5758):195-198.
Zeng and Cullen, Structural requirements for pre-microRNA binding and nuclear export by Exportin 5. 2004 Nucleic Acids Res. 32(16):4776-85.
Griffiths-Jones, The microRNA Registry. 2004 Nucleic Acids Res. 32:D109-111.
Griffiths-Jones et al., miRBase: microRNA sequences, targets and gene nomenclature. 2006 Nucleic Acids Res. 34:D140-144.
Soukup and Breaker, Relationship between internucleotide linkage geometry and the stability of RNA. 1999 RNA 5:1308-1325.
Abbas-Terki et al. , Lentiviral-mediated RNA interference. 2002 Hum Gene Ther 13: 2197-2201.
Hutvagner et al., Sequence-specific inhibition of small RNA function. 2004 PLoS Biol 2: E98.
Meister, Sequence-specific inhibition of microRNA- and siRNA-induced RNA silencing. 2004 RNA 10:544-550.
Bartlett and Davis, Insights into the kinetics of siRNA-mediated gene silencing from live-cell and live-animal bioluminescent imaging. 2006 Nucleic Acids Res 34:322-333.
Malphettes and Fussenegger, Impact of RNA interference on gene networks. 2006 Metab Eng 8:672-683.
Raab and Stephanopoulos, Dynamics of gene silencing by RNA interference. 2004 Biotechnol Bioeng 88:121-132.
Kiga et al., An RNA aptamer to the xanthine/guanine base with a distinctive mode of purine recognition. 1998 Nucleic Acids Res 26:1755-1760.
Thompson et al., Group I aptazymes as genetic regulatory switches. 2002 BMC Biotechnol 2:21.
Suel et al., Tunability and noise dependence in differentiation dynamics. 2007 Science 315:1716-1719.
Gardner et al., Construction of a genetic toggle switch in *Escherichia coli.* 2000 Nature 403:339-342.
Yi et al., Exportin-5 mediates the nuclear export of premicroRNAs and short hairpin RNAs. 2003 Genes Dev 17:3011-3016.
Ketting et al., Dicer functions in RNA interference and in synthesis of small RNA involved in developmental timing in C. elegans. 2001 Genes Dev 15:2654-2659.
Gregory et al., Human RISC couples microRNA biogenesis and posttranscriptional gene silencing. 2005 Cell 123:631-640.
Kok et al., Human TRBP and PACT directly interact with each other and associate with dicer to facilitate the production of small interfering RNA. 2007 J Biol Chem 282:17649-17657.
Lee et al., The role of PACT in the RNA silencing pathway. 2006 EMBO J 25:522-532.
Matranga et al., Passenger-strand cleavage facilitates assembly of siRNA into Ag02-containing RNAi enzyme complexes. 2005 Cell 123:607-620.
Rand et al., Argonaute2 cleaves the anti-guide strand of siRNA during RISC activation. 2005 Cell 123:621-629.
Westerhout and Berkhout, A systematic analysis of the effect of target RNA structure on RNA interference. 2007 Nucleic Acids Res. 35(13):4322-4330.
Grimm et al., Fatality in mice due to oversaturation of cellular microRNNshort hairpin RNA pathways. 2006 Nature 441:537-541.
Yi et al., Overexpression of exportin 5 enhances RNA interference mediated by short hairpin RNAs and microRNAs. 2005 RNA 11:220-226.
Danilova et al., RNAKinetics: a web server that models secondary structure kinetics of an elongating RNA. 2006 J Bioinform Comput Biol 4:589-596.
Croft et al., Is prokaryotic complexity limited by accelerated growth in regulatory overhead? 2003 Genome Biology 5:P2.
Dueber et al., Engineering synthetic signaling proteins with ultrasensitive input/output control. 2007 Nat Biotechnol 25:660-662.
Elowitz and Leibler, A synthetic oscillatory network of transcriptional regulators. 2000 Nature 403:335-338.
Flotte, Size does matter: overcoming the adeno-associated virus packaging limit. 2000 Respir Res 1:16-18.

Grate and Wilson, Inducible regulation of the *S. cerevisiae* cell cycle mediated by an RNA aptamer-ligand complex. 2001 Bioorg Med Chem 9:2565-2570.
Grieger and Samulski, Packaging capacity of adeno-associated virus serotypes: impact of larger genomes on infectivity and postentry steps. 2005 J Virol 79:9933-9944.
Grundy and Henkin, From ribosome to riboswitch: control of gene expression in bacteria by RNA structural rearrangements. 2006 Crit Rev Biochem Mol Biol 41:329-338.
Hall et al., Computational selection of nucleic acid biosensors via a slip structure model. 2007 Biosens Bioelectron 22:1939-1947.
Hooshangi et al., Ultrasensitivity and noise propagation in a synthetic transcriptional cascade. 2005 Proc Natl Acad Sci USA 102: 3581-3586.
Huang and Ferrell, Ultrasensitivity in the mitogen-activated protein kinase cascade. 1996 Proc Natl Acad Sci USA 93: 10078-10083.
Jenison et al., High-resolution molecular discrimination by RNA. 1994 Science 263:1425-1429.
Lee et al., Aptamer database. 2004 Nucleic Acids Res 32:D95-100.
Lynch et al., A high-throughput screen for synthetic riboswitches reveals mechanistic insights into their function. 2007 Chem Biol 14:173-184.
Ogawa and Maeda, An artificial aptazyme-based riboswitch and its cascading system in *E. coli.* 2008 Chembiochem 9:206-209.
Shalgi et al., Global and Local Architecture of the Mammalian microRNA-Transcription Factor Regulatory Network. 2007 PLoS Comput Biol 3:e131.
Sudarsan et al., Metabolite-binding RNA domains are present in the genes of eukaryotes. 2003 RNA 9:644-647.
Suess et al., Conditional gene expression by controlling translation with tetracycline-binding aptamers. 2003 Nucleic Acids Res 31:1853-1858.
Weigand and Suess, Tetracycline aptamer-controlled regulation of pre-mRNA splicing in yeast. 2007 Nucleic Acids Res 35:4179-4185.
Wieland and Hartig, Improved aptazyme design and in vivo screening enable riboswitching in bacteria. 2008 Angew Chern Int Ed Eng147:2604-2607.
Javaherian et al., Selection of aptamers for a protein target in cell lysate and their application to protein purification. 2009 Nucleic Acids Res. 37(8):e62.
Yunusov et al., Kinetic capillary electrophoresis-based affinity screening of aptamer clones. 2009 Anal Chim Acta. 631(1):102-7.
Amarzguioui et. al. , Tolerance for mutations and chemical modifications in a siRNA, *Nucleic Acid Research* 31: 589-595, 2003.
Chiu & Rana, RNAi in Human Cells: Basic Structural and Functional Features of Small Interfering RNA, Mol. Cell 10: 549-561,2002.
Chiu & Rana, siRNA function in RNAi: A chemical modification analysis, RNA 9: 1034-1048,2003.
Geiger, Burgstaller et al., RNA aptamers that bind L-arginine with sub-micromolar dissociation constants and high enantioselectivity,Nucleic Acids Research vol. 24, Issue 6, 1029-1036.
Hamada et al.,Effects on RNA Interference in Gene Expression (RNAi) in Cultured Mammalian Cells of Mismatches and the Introduction of Chemical Modifications at the 3'-Ends of siRNAs, *Antisense Nucleic Acid Drug Dev.* 12(5): 301-309,2002.
Harborth et al.,Sequence, Chemical, and Structural Variation of Small Interfering RNAs and Short Hairpin RNAs and the Effect on Mammalian Gene Silencing ,*Antisense Nucleic Acid Drug Dev.* 13(2): 83-105,2003.
Hwang et al., A Hexanucleotide Element Directs MicroRNA Nuclear Import, *Science* 315: 97-100, 2007.
Kim et al., Synthetic dsRNA Dicer substrates enhance RNAi potency and efficacy ,*Nature Biotech.* 23: 222-226, 2008.
Lescoute and Westhof, Topology of three-way junctions in folded RNAs, *RNA* 12: 83-93, 2006.
Li and Breaker, Kinetics of RNA Degradation by Specific Base Catalysis of Transesterification Involving the 2'-Hydroxyl Group, *J Am. Chem. Soc.* 121: 5364-5372, 1999.
McBride et al., Artificial miRNAs mitigate shRNA-mediated toxicity in the brain: Implications for the therapeutic development of RNAi, *PNAS* 105: 5868, 2008.

(56) References Cited

OTHER PUBLICATIONS

Nickols et al.,Suppression of androgen receptor-mediated gene expression by a sequence-specific DNA-binding polyamide ,*Proc. Natl.Acad. Sci. USA* 104: 10418-10423,2007.
Ohrt et ai., Fluorescence correlation spectroscopy and fluorescence cross-correlation spectroscopy reveal the cytoplasmic origination of loaded nuclear RISC in vivo in human cells, *Nucleic Acids Res.* 36(20): 6439-6449, 2008.
Schwarz et. al., Evidence that siRNAs Function as Guides, Not Primers, in the *Drosophila* and Human RNAi Pathways, Mol. Cell 10: 537-548, 2002.
Soukup and Soukup, Riboswitches exert genetic control through metabolite-induced conformational change, Current Opinions in Structural Biology 14: 344, 2004.
Zhou et al.,Novel Dual Inhibitory Function Aptamer—siRNA Delivery System for HIV-1 Therapy ,*Molecular Therapy* 16: 1481-1489,2008.
Aagard and Rossi, "RNAi Therapeutics: Principles, Prospects and Challenges," *Adv Drug Deliv Rev* 59(2-3):75-86 (2007).
Alberts et al., "The molecular biology of the Cell, Chapter 6: DNA Replication, Repair, and Recombination," Preliminary Version (2003) 6:1-33, Garland Sciences.
Araki et al., "Allosteric regulation of a ribozyme activity through ligand-induced conformational change," *Nucleic Acids Research* 26(14): 3379-3384 (1998).
Birikh et al., "The structure, function and application of the hammerhead ribozyme," *Eur J. Biochem* 245:1-16 (1997).
Blount and Uhlenbeck, "The structure-function dilemma of the hammerhead ribozyme," *Annu Rev Biophys Biomol Struct*, 34:415-440 (2005).
Bunka and Stockley, "Aptamers come of age—at last," *Nat Rev Microbiol* 4:588-596 (2006).
Burke and Greathouse, "Low-magnesium, trans-cleavage activity by type III, tertiary stabilized hammerhead ribozymes with stem 1 discontinuities," *BMC Biochem* 6:14 (2005).
Canny et al., "Fast cleavage kinetics of a natural hammerhead ribozyme," *J. Am. Chem Soc* 126(35):10848-10849 (2004).
Dambach, D.M., "Potential adverse effects associated with inhibition of p38a/β MAP kinases," *Curr Top Med Chem* 5(10):929-939 (2005).
De La Pena et al., "Peripheral regions of natural hammerhead ribozymes greatly increase their self-cleavage activity," *Embo J.* 22(20):5561-5570 (2003).
Dellarole et al., "Thermodynamics of Cooperative DNA Recognition at a Replication Origin and Transcription Rejulatory Site," Biochemistry (2010) 49:10277-10286.
Elion, "The Ste5p scaffold," *J. Cell Sci*, 114(22):3967-3978 (2001).
Endy, "Foundations for engineering biology," *Nature* 438:449-453 (2005).
Gossen and Bujard, "Tight control of gene expression in mammalian cells by tetracycline-responsive responsive promoters," *Proc Natl Acad Sci USA* 89:5547-5551 (1992).
Grassi et al., "Cleavage of collagen RNA transcripts by hammerhead ribozymes in vitro is mutation-specific and shows competitive binding effects," *Nucleic Acids Res* 25(17):3451-3458 (1997).
Hammann et al., "Dissection of the ion-induced folding of the hammerhead ribozyme using 19F NMR," *Proc Natl Acad Sci USA* 98(10):5503-5508 (2001).
Hanahan and Weinberg, "The Hallmarks of Cancer," *Cell*, 100(1):57-70 (2000).
Hanson et al., "Tetracycline-aptamer-mediated translational regulation in yeast," *Mol Microbiol* 49(6):1627-1637 (2003).
International Search Report in International Application No. PCT/US07/84364 (Aug. 19, 2008).
Liu et al., "Soafenib blocks the RAF/MEK/ERK pathway, inhibits tumor angiogenesis, and induces tumor cell apoptosis in hepatocellular carcinoma model PLC/PRF/5," *Cancer Res* 66(24):11851-11858 (2006).
Long and Uhlenbeck, "Self-cleaving catalytic RNA," *Faseb J.* 7(1):25-30 (1993).

Lutz and Bujard, "Independent and tight regulation of transcriptional units in *Escherichia coli* via the LacR/O, the TetR/O and AraC/$I_1$-$I_2$ regulatory elements," *Nucleic Acids Res* 25(6):1203-1210 (1997).
Mandal and Breaker, "Gene regulation by riboswitches," *Natl Rev Mol Cell Biol* 5:451-463 (2004).
Marschall et al., "Inhibition of gene expression with ribozymes," *Cell Mol Neurobiol* 14(5):523-538 (1994).
McCormick, F., "Signalling Networks that Cause Cancer," *Trends Cell Biol*, 9(12):M53-M56 (1999).
Ng and Abelson, "Isolation and sequence of the gene for actin in *Saccharomyces cerevisiae*," *Proc Natl Acad Sci USA* 77(7):3912-3916 (1980).
Nishiwaki et al., "Structure of the yeast HIS5 gene responsive to general control of amino acid biosynthesis," Mol Gen Genet 208:159-167 (1987).
Ogawa et al., "Purification, Characterization, and Gene Cloning of Purine Nucleosidase from *Ochrobactrum anthropi*," *Appl Environ Microbiol* 67(1):1783-1787 (2001).
Pan et al., "A self-processing ribozyme cassette: utility against human papillomavirus 11 E6/E7 mRNA and hepatitis B virus," *Mol Ther* 9(4):596-606 (2004).
Park et al., "Rewiring MAP kinase pathways using alternative scaffold assembly mechanisms," *Science* 299:1061-1064 (2003).
Pelletier and Sonenberg, "Insertion mutagenesis to increase secondary structure within the 5' noncoding region of a eukaryotic mRNA reduces translational efficiency," *Cell* 40:515-526 (1985).
Penedo et al., "Folding of the natural hammerhead ribozyme is enhanced by interaction of auxiliary elements," *RNA* 10(5):880-888 (2004).
Pley et al, "Three-dimensional structure of a hammerhead ribozyme," *Nature* 372:68-74 (1994).
Qi and Elion, "MAP Kinase Pathways," *J. Cell Sci*, 118(16):3569-3571 (2005).
Saksmerprome et al., "Artificial tertiary motifs stabilizing trans-cleaving hammerhead ribozymes under conditions of submillimolar divalent ions and high temperatures," *RNA* 10(12):1916-1924 (2004).
Salehi-Ashtiani and Szostak, "In vitro evolution suggests multiple origins for the hammerhead ribozyme," *Nature* 414:82-84 (2001).
Scherr et al., "Specific hammerhead ribozyme-mediated cleavage of mutant N-ras mRNA in vitro and ex vivo," *J. Biol Chem* 272(22):14304-14313 (1997).
Shapiro, "Discovering New MPA Kinase Inhibitors," *Chem Biol* 13(8):807-809 (2006).
Silverman, Rube Goldberg goes (ribo)nuclear? Molecular switches and sensors made From RNA. *RNA*, 9:377-383 (2003).
Soukup and Breaker, "Engineering precision RNA molecular switches," *Proc Natl Acad Sci USA*, 96:3584-3589 (1999).
Tindall et al., "Fidelity of DNA Synthesis by the Thermus aquaticus DNA Polymerase," *Biochem.*, 27(16):6008-6013 (1988).
Voigt, "Genetic parts to program bacteria," *Curr Opin Biotechnol* 17:548-557 (2006).
Weinberg and Rossi, "Comparative single-turnover kinetic analyses of trans-cleaving hammerhead ribozymes with naturally derived non-conserved sequence motifs," *FEBS Lett* 579(7):1619-1624 (2005).
Weinberg et al., "Effective anti-hepatitis B virus hammerhead ribozymes derived from multimeric precursors," *Oligonucleotides* 17(1):104-112 (2007).
Duconge and Toulme, "In vitro selection identifies key determinants for loop-loop interactions: RNA aptamers selective for the TAR RNA element of HIV-1." RNA (19 99); 5: 1605-1614.
Aagaard et al., "Engineering and optimization of the miR-1 06b cluster for ectopic expression of multiplexed anti-HIV RNAs." Gene Ther (2008); 15: 1536-1549.
Bauer et al., "Prevention of interferon-stimulated gene expression using microRNA-designed hairpins." Gene Ther. (2009); 16: 142-147.
Baulcombe, "Diced defence." Nature (2001); 409(6818):295-6.
Biesecker et al, "Derivation of RNA aptamer inhibitors of human complement C5." Immunopharmacology (1999); 42 (1-3): 219-30.
Boiziau et al. "DNA Aptamers Selected Against the HIV-1 trans-Activationresponsive RNA Element Form RNA-DNA Kissing Complexes." Journal of biological chemistry (1999); 274(18): 12730-12737.

(56) References Cited

OTHER PUBLICATIONS

Boiziau et al., "Identification of Aptamers Against the DNA Template for In Vitro Transcription of the HIV-1 TAR Element." Antisense Nucleic Acid Drug Dev. (1997); 7(4): 369-380.
Boudreau et al., "Artificial microRNAs as siRNA shuttles: improved safety as compared to shRNAs in vitro and in vivo." Mol. Ther. (2009); 17(1): 169-175.
Brockstedt et al., "In vitro evolution of RNA aptamers recognizing carcinogenic aromatic amines." Biochem. Biophys. Res. Commun. (2004); 313(4): 1004-1008.
Burke et al., "RNA aptamers to the adenosine moiety of S-adenosyl methionine: structural inferences from variations on a theme and the reproducibility of SELEX." Nucleic Acids Research (1997); 25(10): 2020-2024.
Cai et al., "Human microRNAs are processed from capped, polyadenylated transcripts that can also function as mRNAs." RNA (2004); 10: 1957-1966.
Daniels, "A tenascin-C aptamer identified by tumor cell SELEX: Systematic evolution of ligands by exponential enrichment." PNAS (2003); 100(26): 15416-15421.
Eulberg et al., "Development of an automated in vitro selection protocol to obtain RNA-based aptamers: identification of a biostable substance P antagonist." Nucleic Acids Res. (2005); 33(4): e45.
Flinders et al., "Recognition of planar and nonplanar ligands in the malachite green-RNA aptamer complex." Chembiochem (2004); 5(I): 62-72.
Friedman et al., "Most mammalian mRNAs are conserved targets of microRNAs." Genome Res. (2009); 19: 92-105.
Fukusaki et al., "DNA aptamers that bind to chitin." Bioorg. Med. Chem. Lett. (2000); 10(5): 423-425.
Gebhardt, "RNA aptamers to s-adenosylhomocysteine: kinetic properties, divalent cation dependency, and comparison with anti-s-adenosyl homocysteine antibody." Biochemistry (2000); 39(24): 7255-7265.
Gilbert et al., "RNA aptamers that specifically bind to a K Ras-derived farnesylated peptide." Bioorg. Med. Chem. (1997); 5(6): 1115-1122.
Gopinath et al., "An efficient RNA aptamer against human influenza B virus hemagglutinin." J Biochem (Tokyo) (2006); 139(5): 837-846.
Gregory et al., "The Microprocessor complex mediates the genesis of microRNAs." Nature (2004); 432: 235-240.
Guil et al., "The multifunctional RNA-binding protein hnRNP A1 is required for processing of miR-18a." Nat Struct Mol Biol (2007); 14: 591-596.
Haller et al., "In vitro selection of a 7-methyl-guanosine binding RNA that inhibits translation of capped mRNA molecules." PNAS (1997); 94: 8521-8526.
Hammond et al., "Argonaute2, a Link Between Genetic and Biochemical Analyses of RNAi." Science (2001); 293(5532): 1146-1150.
Han et al., "Molecular basis for the recognition of primary microRNAs by the Drosha-DGCR8 complex." Cell (2006); 125: 887-901.
Han et al., "The Drosha-DGCR8 complex in primary microRNA processing." Genes Dev (2004); 18: 3016-3027.
Han et al., "Posttranscriptional crossregulation between Drosha and DGCR8." Cell (2009); 136: 75-84.
Hesselberth et al., "In Vitro Selection of RNA Molecules That Inhibit the Activity of Ricin A-chain." Journal of Biological Chemistry (2000); 275(7): 4937-4942.
Hicke et al., "Tenascin-C Aptamers Are Generated Using Tumor Cells and Purified Protein." J. Biol. Chem. (2001); 276(52): 48644-4854.
Hirao et al., "RNA Aptamers That Bind to and Inhibit the Ribosome-inactivating Protein, Pepocin." Journal of Biological Chemistry (2000); 275(7): 4943-4948.
Hornung et al., "In vitro selected RNA molecules that bind to elongation factor tu." Biochemistry (1998); 37: 7260-7267.

Jeong et al., "In vitro selection of the RNA aptamer against the sialyl lewis x and its inhibition of the cell adhesion." Biochemical and Biophysical Research Communications (2001); 281(I): 237-243.
Kato et al., "In vitro selection of DNA aptamers which bind to cholic acid." Biochim. Biophys. Acta (2000); 1493(1-2): 12-18.
Kedde et al., "RNA-binding protein Dndl inhibits microRNA access to target mRNA." Cell (2007); 131: 1273-1286.
Kimoto et al., "Anti-(Raf-1) RNA aptamers that inhibit Ras-induced Raf-1 activation." Eur. J. Biochem. (2002); 269(2): 697-704.
Kimoto et al., "RNA aptamers that specifically bind to the Ras-binding domain of Raf-1." FEBS Lett. (1998); 441(2): 322-326.
Koizumi et al., "Molecular recognition of cAMP by an RNA aptamer." Biochemistry (2000); 39(30): 8983-8992.
Zeng et al., "Recognition and cleavage of primary microRNA precursors by the nuclear processing enzyme Drosha." EMBO J. (2005); 24: 138-148.
Kraus et al, "Cutting Edge: Novel RNA Ligands Able to Bind CD4 Antigen and Inhibit CD4+ T Lymphocyte Function." J. Immunol. (1998); 160(II): 5209-5212.
Lee et al., "The nuclear RNase III Drosha initiates microRNA processing." Nature (2003); 425:415-419.
Lee et al., "In vitro and in vivo assays for the activity of Drosha complex." Methods Enzymol (2007); 427: 89-106.
Lee et al., "MicroRNA maturation: stepwise processing and subcellular localization." EMBO J. (2002); 21(17): 4663-4670.
Legiewicz et al., "A More Complex Isoleucine Aptamer with a Cognate Triplet." J. Biol. Chem. (2005); 280(20): 19815-19822.
Liu, et al., "RNA aptamers specific for bovine thrombin." Journal of Molecular Recognition (2003); 16(1): 23-27.
Lozupone et al., "Selection of the simplest RNA that binds isoleucine." RNA (2003); 9(II): 1315-1322.
Misono et al., "Selection of RNA aptamers against human influenza virus hemagglutinin using surface plasmon resonance." Anal. Biochem. (2005); 342(2): 312-317.
Muller et al., "Thermodynamic characterization of an engineered tetracycline-binding riboswitch." Nucleic Acids Res (2006); 34(9): 2607-2617.
Osborne et al., "Nucleic Acid Selection and the Challenge of Combinatorial Chemistry." Chern. Rev (1997); 97: 349-370.
Roychowdhury-Saha et al., "Flavin recognition by an RNA aptamer targeted toward FAD." Biochemistry (2002); 41(8): 2492-2499.
Ruckman, et al., "2'-Fluoropyrimidine RNA-based Aptamers to the 165-Amino Acid Form of Vascular Endothelial Growth Factor (VEGF165)." J. Biol. Chem. (1998); 273(32): 20556-20567.
Saran et al., "The tyranny of adenosine recognition among RNA aptamers to coenzyme A." BMC Evol. Biol. (2003); 3(I): 26.
Schneider et al, "Selective enrichment of RNA species for tight binding to Escherichia coli rho factor." FASEB J. (1993); 7(I): 201-207.
Sontheimer, "Assembly and Function of RNA Silencing Complexes." Nat Rev Mol Cell Biol. (2005); 6(2):127-138.
Stern et al., "A system for Cre regulated RNA interference in vivo." Proc Natl Acad Sci USA (2008); 105: 13895-13900.
Sun et al., "Multi-miRNA hairpin method that improves gene knockdown efficiency and provides linked multi-gene knockdown." Biotechniques (2006); 41: 59-63.
Tahiri-Alaoui et al., "High affinity nucleic acid aptamers for strptavidin incorporated into bi-specific capture ligands." Nucleic Acids Res. (2002); 30(10): e45.
Takeno et al., "Selection of an RNA Molecual That Specifically Inhibits the Protease Activity of Subtilisin." Journal of Biochemistry (1999); 125(6): 1115-1119.
Tao et al., "Arginine-binding RNAs resembling tar identified by in vitro selection." Biochemistry (1996); 35(7): 2229-2238.
Rusconi et al., "Blocking the initiation of coagulation by RNA aptamers to factor VIIa." Thromb Haemost. (2000); 84(5): 841-848.
Tuerk et al., "RNA pseudoknots that inhibit human immunodeficiency virus type 1 reverse transcriptase." Proc Natl Acad Sci USA (1992); 89:6988-6992.
Tuleuova et al., "Modulating endogenous gene expression of mammalian cells via RNA-small molecule interaction." Biochem Biophys Res Commun (2008); 376: 169-173.

(56) References Cited

OTHER PUBLICATIONS

Ulrich et al., "In vitro selection of RNA molecules that displace cocaine from the membrane-bound nicotinic acetylcholine receptor." Proc. Natl. Acad. Sci. USA (1998); 95(24): 14051-14056.

Urvil et al., "Selection of RNA aptamers that bind specifically to the NS3 protease of hepatitis C virus." European Journal of Biochemistry (1997); 248(I): 130-138.

Vaish et al., "A novel, modification-dependent ATP-binding aptamer selected from an RNA library incorporating a cationic functionality." Biochemistry (2003); 42( 29): 8842-8851.

Wallace et al., "In vitro selection and characterization of streptomycin-binding RNAs: Recognition discrimination between antibiotics." RNA (1998); 4(I): 112-123.

Wang et al., "RNA molecules that specifically and stoichiometrically bind aminoglycoside anitibiotics with high affinities." Biochemistry (1996); 35(38): 12338-12346.

Wang et al., "Recent patents on the identification and clinical application of microRNAs and target genes." Recent Pat DNA Gene Seq (2007); 1: 116-124.

Wang et al., "MicroRNA-based therapeutics for cancer." BioDrugs (2009); 23:15-23.

Weigand et al., "Screening for engineered neomycin riboswitches that control translation initiation." RNA (2008); 14: 89-97.

Wieland et al., "Artificial ribozyme switches containing natural riboswitch aptamer domains." Angew Chern Int Ed Eng (2009); 148: 2715-2718.

Wilson et al., "Functional requirements for specific ligand recognition by a biotin-binding RNA pseudoknot." Biochemistry (1998); 37: 14410-14419.

Xia et al., "Multiple shRNAs expressed by an inducible pol II promoter can knock down the expression of multiple target genes." Biotechniques (2006); 41: 64-68.

Yang et al., "DNA ligands that bind tightly and selectively to cellobiose." PNAS (1998); 95(10): 5462-5467.

Yeom et al., "Characterization of DGCR8/Pasha, the essential cofactor for Drosha in primary miRNA processing." Nucleic Acids Res. (2006); 34(16):4622-4629.

Zeng et al., "Sequence requirements for micro RNA processing and function in human cells." RNA (2003); 9: 112-123.

Zeng et al., "Efficient processing of primary microRNA hairpins by Drosha requires flanking nonstructured RNA sequences." J Biol Chern (2005); 280: 27595-27603.

Zeng et al., "Both natural and designed micro RNAs can inhibit the expression of cognate mRNAs when expressed in human cells." Mol Cell (2002); 9: 1327-1333.

Wieland M., et al., "Artificial riboswitches: synthetic mRNA-based regulators of gene expression." Chembiochem. (2008); 9:1873-1878.

Novina CD, et al., "The RNAi revolution." Nature (2004); 430(6996):161-164.

Fedor MJ, et al., "The catalytic diversity of RNAs." Nat Rev Mol Cell Biol. (2005); 6:399-412.

Breaker RR. "Complex riboswitches." Science (2008); 319:1795-1797.

Wilson DS, et al., "In vitro selection of functional nucleic acids." Annu Rev Biochem. (1999); 68:611-647.

Kim et al., "An artificial riboswitch for controlling pre-mRNA splicing." RNA (2005) 11:1667-1677.

Wang et al., "General and Specific Functions of Exonic Splicing Silencers in Splicing Control." Molecular Cell (2006); 23: 61-70.

Villemaire et al., "Reprogramming Alternative Pre-messenger RNA Splicing through the Use of Protein-binding Antisense Oligonucleotides." Biol. Chem. (2003); 278(50): 50031-50039.

Hanson et al., "Molecular analysis of a synthetic tetracycline-binding riboswitch," *RNA*, 11:503-511 (2005).

Montange and Batey, "Structure of the S-adenosylmethionine riboswitch regulatory mRNA element," *Nature*, 441:1172 (2006).

Schwalbe et al., "Structures of RNA Switches: Insight into Molecular Recognition and Tertiary Structure," *Angew. Chem. Int. Ed.*, 46:1212-1219 (2007).

Serganov and Patel, "Ribozymes, riboswitches and beyond: regulation of gene expression without proteins," *Nature*, 8:776-790 (2007).

Snyder et al., "Bent DNA at a yeast autonomously replicating sequence," *Nature*, 324:87-89 (1986).

* cited by examiner

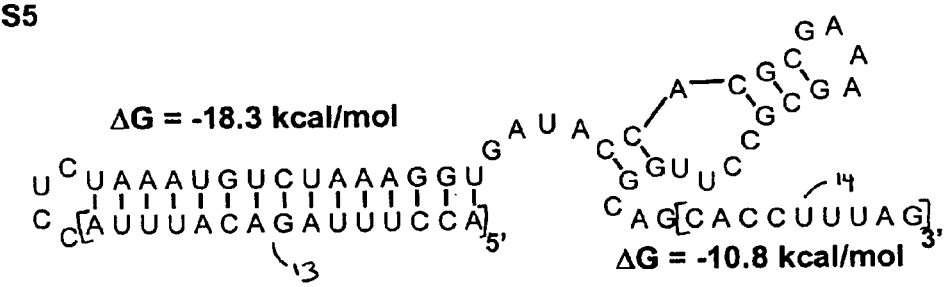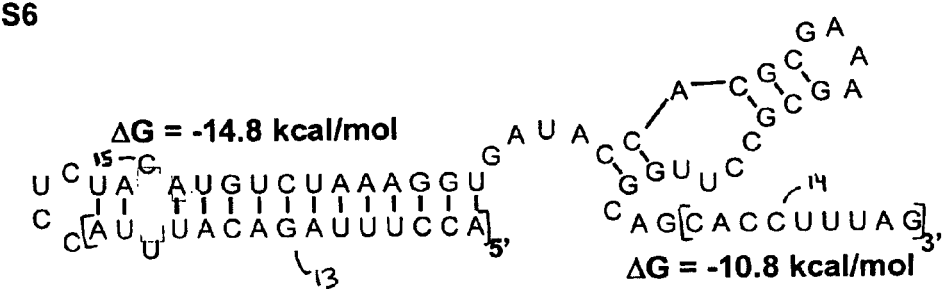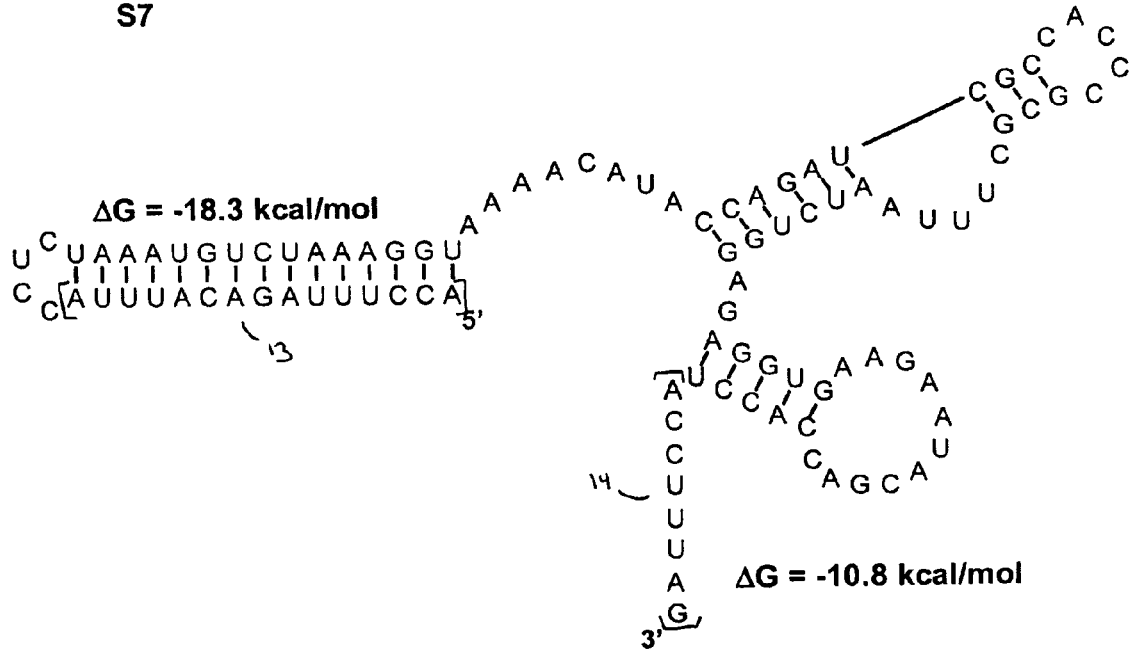
Figure 8

| RNA | 0 mM theophylline | 2 mM theophylline |
|---|---|---|
| GFP mRNA | 1±0.048 | 1.1±0.052 |
| Antiswitch s1 | 990±46.2 | 971±47.1 |
| Uncleaved hammerhead | 0.158±0.009 | 0.149±0.008 |

Figure 11

| Plasmid | Description | Parent plasmid |
|---|---|---|
| pTARGET1.gfp | pRS314-Gal expressing yEGFP | pRS314-Gal |
| pTARGET2.gfp/V | pRS314-Gal expressing yEGFP and Venus | pRS314-Gal |
| pSWITCH1.s1 | GAL1 / ribozyme construct expressing s1 | pRS316-Gal |
| pSWITCH1.s2 | GAL1 / ribozyme construct expressing s2 | pRS316-Gal |
| pSWITCH1.s3 | GAL1 / ribozyme construct expressing s3 | pRS316-Gal |
| pSWITCH1.s4 | GAL1 / ribozyme construct expressing s4 | pRS316-Gal |
| pSWITCH1.s5 | GAL1 / ribozyme construct expressing s5 | pRS316-Gal |
| pSWITCH1.s6 | GAL1 / ribozyme construct expressing s6 | pRS316-Gal |
| pSWITCH1.s7 | GAL1 / ribozyme construct expressing s7 | pRS316-Gal |
| pSWITCH1.s8 | GAL1 / ribozyme construct expressing s8 | pRS316-Gal |
| pSWITCH2.s1/9 | GAL1 / ribozyme construct expressing s1 and s9 | pRS316-Gal |
| pSWITCH1.anti | GAL1 / ribozyme construct expressing GFP antisense | pRS316-Gal |
| pSWITCH1.aptamer | GAL1 / ribozyme construct expressing theophylline aptamer | pRS316-Gal |

Figure 12

| Antiswitch construct | RNA sequence |
|---|---|
| s1 | ACCUUUAGACAUUUACCUCUAAAUGUCUAAAGGUGAUACCAGCAUCGUCUUGAUGCCCUUGGCAGCACCUUUAG |
| s2 | ACCUUUAGACAUUUACCUCUACAUGUCUAAAGGUGAUACCAGCAUCGUCUUGAUGCCCUUGGCAGCACCUUUAG |
| s3 | ACCUUUAGACAUUUAAUUAACCUCUAAAUGUCUAAUUAAAGGUGAUACCAGCAUCGUCUUGAUGCCCUUGGCAGCUUCCACCUUUAG |
| s4 | ACCUUUAGACAUUUACCCCUACAUGUCUAAAGGUGAUACCAGCAUCGUCUUGAUGCCCUUGGCAGCACCUUUAG |
| s5 | ACCUUUAGACAUUUACCUCUAAAUGUCUAAAGGUGAUACCAGCGAAAGCGCCUUGCGAAAGCGCCUUGGCAGCACCUUUAG |
| s6 | ACCUUUAGACAUUUACCUCUACAUGUCUAAAGGUGAUACCAGCGAAAGCGCCUUGGCAGCACCUUUAG |
| s7 | ACCUUUAGACAUUUACCUCUAAAUGUCUAAAGGUGAAAACAUACCAGAUCGCCACCCGGCCUUUAAUCUGGAGAGG UGAAGAAUACGACCACCUUUAG |
| s8 | ACCUUUAGACAUUUAGAUACCAGCAUCGUCUUGAUGCCCUUGGCAGCUAAAUGUC |
| s9 | UUGCUCACCAUGGUCCUCACCAUGGAGCAAAAAACAUACCAGAUCGCCACCCGGCCUUUAAUCUGGAGAGGUG AAGAAUACGACCACCUUGCUCAC |
| GFP antisense | ACCUUUAGACAUUUA |
| Theophylline aptamer | AGGUGAUACCAGCAUCGUCUUGAUGCCCUUGGCAGCACCU |
| s1.qpcr.fwd | ACCAGACAACCCAAAGCAA |
| s1.qpcr.rev | CTAAAGGTGCTGCCAAGGG |
| s1/2ham.qpcr.fwd | TAGCGGATCCAGGTCTGATGAGTCCGTGAGGACG |
| gfp.qpcr.fwd | ATTTTGGTTGAATTAGATGGTGA |
| gfp.qpcr.rev | CTGGCAATTTACCAGTAGTACAAA |

Figure 13

APTAMER REGULATED NUCLEIC ACIDS AND USES THEREOF

CROSS-REFERENCE TO RELATED APPLICATIONS

This application claims the benefit of priority from U.S. Provisional Application No. 60/615,977 filed on Oct. 5, 2004 and U.S. Provisional Application No. 60/641,658, filed on Jan. 6, 2005, the specifications of which are incorporated herein by reference.

BACKGROUND OF THE INVENTION

In recent years, cis- and trans-RNA elements have become well recognized as important regulators of gene expression. Cells use diverse non-coding RNA-based elements to regulate complex genetic networks such as those involved in developmental timing and circadian clocks (Banerjee et al., *Bioessays* 24, 119-29 (2002); and Kramer et al., *Nature* 421, 948-52 (2003)). Antisense RNAs are small trans-acting RNAs (taRNAs) that bind to complementary segments of a target messenger RNA (mRNA) and regulate gene expression through mechanisms such as targeting decay, blocking translation, and altering splicing patterns (Good, *Cell Mol Life Sci* 60, 823-4 (2003); Good, *Cell Mol Life Sci* 60, 854-61 (2003); and Vacek et al., *Cell Mol Life Sci* 60, 825-33 (2003)). MicroRNAs (miRNAs), small taRNAs that affect either translation or RNA decay by interacting with complementary sequences in mRNA and the genome, are likely widespread in metazoan gene regulation (Bartel, *Cell* 116, 281-97 (2004)). Small interfering RNAs (siRNAs) and double-stranded RNAs (dsRNAs) are able to precisely target mRNAs and inhibit their expression through the RNA interference (RNAi) pathway in metazoans, and are thought to be part of the cell's host defense system (Scherer, *Curr Pharm Biotechnol* 5, 355-60 (2004)). Ribozymes are RNA molecules exhibiting catalytic function and have been shown to be used by viruses to regulate gene expression (Lilley, *Trends Biochem Sci* 28, 495-501 (2003)). Riboswitches, cis-acting metabolite binding structures in mRNAs, control gene expression by modulating translation initiation, disruption of transcriptional termination, or cleavage of mRNA by ribozyme mechanisms (Mandal et al., *Nat Struct Mol Biol* 11, 29-35 (2004); Winkler, *Nature* 419, 952-6 (2002); and Winkler, *Nature* 428, 281-6 (2004)). Recent studies have demonstrated the prevalence of these RNA-based regulators across diverse groups of organisms from prokaryotes to humans (Barrick et al., *Proc Natl Acad Sci USA* 101, 6421-6 (2004); Yelin et al., *Nat Biotechnol* 21, 379-86 (2003); and Lavorgna et al., *Trends Biochem Sci* 29, 88-94 (2004)).

Researchers have taken advantage of the relative ease with which RNA libraries can be generated and searched to create synthetic RNA-based molecules with novel functional properties. Aptamers are nucleic acid binding species that interact with high affinity and specificity to selected ligands. These molecules are generated through iterative cycles of selection and amplification known as in vitro selection or SELEX (Systematic Evolution of Ligands by EXponential enrichment) (Ellington et al., *Nature* 346, 818-22 (1990); and Tuerk et al., *Science* 249, 505-10 (1990)). Aptamers have been selected to bind diverse targets such as dyes, proteins, peptides, aromatic small molecules, antibiotics, and other biomolecules (Hermann et al., *Science* 287, 820-5 (2000)). High-throughput methods and laboratory automation have been developed to generate aptamers in a rapid and parallel manner (Cox et al., *Nucleic Acids Res* 30, e108 (2002)). Researchers have demonstrated that aptamers can impart allosteric control properties onto other functional RNA molecules. Such allosteric control strategies have been employed to construct and select in vitro signaling aptamers, in vitro sensors, and in vitro allosterically controlled ribozymes (Jhaveri et al., *Nat Biotechnol* 18, 1293-7 (2000); Roth et al., *Methods Mol Biol* 252, 145-64 (2004); and Stojanovic et al., *J Am Chem Soc* 126, 9266-70 (2004)).

In addition to the widespread occurrence of RNA-based regulator elements in natural systems, researchers have recently described engineered riboregulator systems. Cis-acting RNA elements were described that regulate relative expression levels in *Escherichia coli* from a two gene transcript by controlling RNA processing and decay (Smolke et al, *Appl Environ Microbiol* 66, 5399-405 (2000)). In another example, a combined cis/trans riboregulator system was described in *E. coli* in which cis-acting RNA elements mask the ribosome binding site of a transcript, thereby inhibiting translation, and trans-activating RNAs bind to the cis-acting elements to allow translation (Isaacs et al., *Nat Biotechnol* 22, 841-7 (2004)). Cis-acting elements were recently described that control gene expression in mammalian cells and mice by acting through RNA cleavage and whose activity can be regulated by a small molecule drug and antisense oligonucleotides (Yen et al., *Nature* 431, 471-6 (2004)). Finally, an allosteric aptamer construct was recently described that upon binding the dye tetramethylrosamine, interacts with protein-based transcriptional activators to induce transcription (Buskirk et al., *Chem Biol* 11, 1157-63 (2004)).

Riboregulators present powerful tools for flexible genetic regulation. However, there is a need to couple the ability of RNA-based regulators that can directly target transcripts with allosteric control typically associated with protein-based regulators.

SUMMARY OF THE INVENTION

The present invention provides aptamer-regulated trans-acting nucleic acids, or "aptaSwitches" herein. The subject aptaSwitches are a versatile class of nucleic acids that can be readily engineered to be responsive to a variety of ligands, and are useful in many applications. For example, aptaSwitches can be designed to modulate the activity of genes targeted in a ligand-dependent manner, and are therefore useful for modulating the expression of endogenous or heterologous genes.

The trans-acting aptaSwitches of the invention comprises an effector domain, that directs the ligand-dependent activity of the aptaSwitch, such as in a sequence dependent manner, and an aptamer domain that binds to a ligand and induces an allosteric change in the structure of the aptaSwitch so as to affect activity of the effector domain. For instance, binding of the ligand to the aptamer domain can cause a conformational change in the nucleic acid that alters the ability of the effector domain to interact with other molecules (such as enzymes) or target sequences (such as target genes). The effector domain can have at least two conformational states, an "off" state and an "on" state, that is defined by its availability to interact with its target molecule or nucleic acid. For example, in the case of the effector domain being an antisense sequence, the effector domain can adopt a hairpin loop conformation in which the targeting sequence is rendered unavailable to interact with its target gene, and therefore, the aptaSwitch is considered "off." In this antisense embodiment, an aptaSwitch that is "on" may have the effector domain in a configuration that allows it to interact with its target gene, i.e., by being free to hybridize through intermolecular basepairing with a sequence in the target gene. In contrast, considering embodiments having an RNAi construct as the effector domain, the "on" state may be one in which intramolecular basepairing of a targeting sequence within the aptaSwitch creates a duplex (such as a hairpin) that is a substrate for an RNAase III enzyme (such as Dicer), whereas in the "off" state, the targeting sequence is not part of a structure that is (or is as efficient) a substrate. An effector domain of the invention can be switched between its "on" and "off" state in response to ligand binding to the aptamer domain. Aptamer-regulated nucleic acids, therefore, act as a switch whose activity is turned "on" and "off" in response to ligand binding. In certain embodiments, the effector domain's function is dependent on the presence or absence of the ligand, and/or the amount or concentration of the ligand available to bind to the aptamer domain.

In certain embodiments, the subject aptaSwitches include: (i) a substrate sequence that can form a substrate for an extrinsic enzymatic activity, and (ii) an aptamer that binds to a ligand. Binding of the ligand to the aptamer causes a conformational change in the nucleic acid that alters the ability of the substrate sequence to form the substrate for the enzyme and/or alters the efficiency of it to be a substrate for the extrinsic enzymatic activity, e.g., by altering the Km and/or Kcat. In certain embodiments, the substrate sequence forms the substrate only in the presence of the ligand ("ligand activated substrate"), while in other embodiments the substrate sequence forms the substrate only in the absence of the ligand ("ligand inactivated substrate"). In certain preferred embodiments, the effect is dependent on the dose of the ligand.

To further illustrate these embodiments, the conformational change can be one that produces or removes an intramolecular double-stranded feature (which includes the substrate sequence), where the double-stranded feature is the substrate for the extrinsic enzymatic activity.

For instance, the extrinsic enzymatic activity is an RNAse enzyme. In certain cases, the the RNAse enzyme is an RNAse III enzyme, such as DICER or DROSHA. In those embodiments, the substrate sequence is selected to produce siRNA, miRNA or a precursor or metabolite thereof in an RNA Interference pathway, as a product of reaction with the RNAse III enzyme.

In certain embodiments the enzymatic activity can act on the substrate aptaSwitch such that a product of the reaction is a nucleic acid that (a) can induce a biological consequence (e.g. a phenotypic change) in the cell, and (b) partitions in the cell in a manner different from the substrate aptaSwitch. For instance, the product can translocate from the nucleus to the cytplasm whereas the substrate is predominantly localized in the nucleus. To further illustrate, the aptaSwitch can include a substrate sequence that forms a pri-miRNA or pre-miRNA substrate for Drosha (i.e., localized in the nucleus), and the product of Drosha-mediated cleavage is an miRNA that can translocate to the cytplasm and be acted on by Dicer, i.e., inputs into the RNA Interference pathway.

In another illustration, the conformation change can be one that alters the ability of the substrate sequence to form an intermolecular double-stranded feature with a second (discrete) nucleic acid species, such as a target gene, where the double stranded feature is the substrate for the extrinsic enzymatic activity. For instance, the second nucleic acid species can be an mRNA, and the extrinsic enzymatic activity alters the mRNA in a manner dependent on the formation of the double-stranded feature with the aptaSwitch, such as by activation of an RNAse H enzyme and/or RNAse P enzyme or the like.

In still other examples, ligand binding to the aptamer can induce or prevent the substrate sequence from forming a substrate for such other extrinsic enzymatic activities as polymerases, recombinases, ligases, methylases, glycosylases, or nucleases.

In certain embodiments, the nucleic acids of the present invention include: (i) an antisense sequence for inhibiting expression of a target gene, and (ii) an aptamer that binds to a ligand. In these embodiments, binding of the ligand to the aptamer causes a conformational change in the nucleic acid that alters the ability of the antisense sequence to inhibit expression of the target sequence in a second, target gene. Such conformational changes may include altering intramolecular base-pairing within the nucleic acid such that the antisense sequence becomes available to hybridize with a sequence in the target gene. In certain embodiments, the antisense sequence is able to hybridize with the target sequence only in the presence of the ligand ("ligand activated antisense"), while in other embodiments it can hybridize with the target sequence only in the absence of the ligand ("ligand inactivated antisense"). In certain preferred embodiments, the effect is dependent on the dose of the ligand.

To further exemplify, the aptaSwitch can be designed so that ligand binding to the aptamer causes a conformational change that renders the antisense sequence available for hybridization to the target gene, or can be designed so that ligand binding causes a conformational change that renders the antisense sequence unavailable for hybridization to the target gene. In certain designs, the binding of the ligand to the aptamer causes a conformational change in the nucleic acid that alters the melting point ($T_m$) of a duplex formed by hybridization of the antisense sequence to the target gene.

Such embodiments are useful for inhibiting gene expression through the use of an antisense sequence that is selected to hybridize to an RNA transcript of the target gene, or which is selected to hybridize to a genomic sequence of the target gene.

Similarly, the antisense sequence can be selected to alter the levels of expression of different splice variants through hybridization to transcripts in a manner that effects intron splicing.

In certain embodiments, the invention provides a trans-acting nucleic acid for altering expression of a target gene. Such constructs include: (i) a targeting sequence that is capable of hybridizing to the target gene and regulate expression of the target gene; and (ii) an aptamer sequence that binds to a ligand. The targeting sequence can be a single, contiguous stretch of sequence in the aptaSwitch, or can be derived from several discontinuous sequences (i.e. interrupted by one or more intervening nucleotides). When bound by the aptamer, the ligand causes a conformational change in the nucleic acid structure affecting the ability of the targeting sequence to regulate expression of the target gene, resulting in its regulation in a manner dependent on the presence of the ligand. In certain preferred embodiments, the effect is dependent on the dose of the ligand. Exemplary aptaSwitch constructs that are included within these embodiments are those that work through antisense or RNAi mechanisms.

As an example, the targeting sequence can be selected to hybridize to an RNA transcript of the target gene and thereby reduce the amount of protein translated from the RNA transcript, and/or alter splicing of the RNA transcript. Alternatively, the targeting sequence can be selected to hybridize to a genomic sequence of the target gene and reduces the amount of RNA transcribed from the genomic sequence.

In certain embodiments, the subject nucleic acids include: (i) a hybridization sequence that hybridizes to a target sequence of a second nucleic acid, and (ii) an aptamer that binds to a ligand. Ligand binding to the aptamer causes a conformational change in the nucleic acid that alters the ability of the hybridization sequence to hybridize to the target sequence. In certain embodiments, the hybridization sequence is able to hybridize with the target sequence only in the presence of the ligand ("ligand activated hybridization"), while in other embodiments it can hybridize with the target sequence only in the absence of the ligand ("ligand inactivated hybridization"). In certain preferred embodiments, the effect is dependent on the dose of the ligand.

In each of the various embodiments above, the nucleic acid can be a ribonucleic acid (RNA). Likewise, the invention also provides for expression constructs that include (i) a coding sequence which, when transcribed, produces an aptaSwitch in the cell, and (ii) one or more transcriptional regulatory sequences that regulate transcription of the coding sequence for the aptaSwitch in a cell containing the expression construct.

In certain embodiments, the aptaSwitch includes a polyadenylate tail, or in the case of the expression constructs, a coding sequence that when transcribed, produces a poly-A tail on the aptaSwitch transcript. It will be appreciated by those skilled in the art that the subject aptaSwitch constructs can be derived from various nucleotides and nucleotide analogs, as well as utilizing various linkage chemistries, such as may be adapted for use in the present invention from the art of antisense and siRNA constructs. To further illustrate, the aptaSwitch can include one or more non-naturally occurring nucleoside analogs and/or one or more non-naturally occurring backbone linkers between nucleoside residues. Such analogs and linkers can be used to alter the stability, nuclease susceptibility (or resistance) and/or bioavailability (such as cell permeability) relative to a corresponding nucleic acid of naturally occurring nucleosides and phosphate backbone linkers.

In certain preferred embodiments of the subject aptaSwitches, the nucleic acid construct is in the size range of 40-500 nucleotides, more preferably 50-200 nucleotides.

The choice of ligand to which the aptamer binds and the aptaSwitch therefore is regulated by are vast. In certain instances, the ligand is a small molecule having a molecular weight less than 2500 amu. These can be naturally or non-naturally occurring molecules, including peptides, small organic molecules (including drugs and certain metabolites and intermediates, cofactors, etc), and metal ions merely to illustrate.

In certain embodiments, the ligand is a natural product. This includes signal transduction agents, such as second messenger molecules or post-translationally modified proteins, as well as polypeptides, peptides, nucleic acids, carbohydrates, fatty acids and lipids, non-peptide hormones (such as steroids) and metabolic precursors or products thereof.

In certain embodiments, particularly for regulation of a metabolic pathway in a cell, the ligand can be an enzyme co-factor, an enzyme substrate or a product of an enzyme-mediated reaction.

Particularly for embodiments where it is intended that the aptaSwitch be regulated using an ectopically administered ligand, the ligand is preferably one that is cell permeable.

In certain other embodiments, the aptamer domain of an aptaSwitch is responsive to other environmental changes. Environmental changes include, but are not limited to changes in pH, temperature, osmolarity, or salt concentration.

Certain embodiments provide methods of designing and selecting aptamers or aptamer domains that are responsive to one or more pre-selected or pre-determined ligands. aptaSwitches may also be "tuned" so that their switching behavior is more or less responsive to ligand binding.

aptaSwitches may also be "tuned" so that the binding affinity of the aptamer domain is more or less sensitive to its ligand. For instance, the thermodynamic properties of intramolecular duplex formation and other 2° and 3° structures in the aptaSwitch may be altered so that the aptamer domain is more or less amenable to ligand binding, i.e., such as may be manifest in the dissociation constant ($K_d$) or other kinetic parameters (such as $K_{on}$ and $K_{off}$ rates). Alternatively, allosteric changes in the effector domain may be more or less responsive to ligand binding upon alterations in hybridization and other intramolecular interactions that may effect 2° and 3° structures of the aptaSwitch. Forward engineering strategies for altering the thermodynamic properties of nucleic acid structures are well known in the art. For instance, increased complementary nucleic acid pairing may increase the stability of an effector or aptamer domain. It is anticipated that the absolute and relative stabilities of the effector stem and the aptamer stem will be important design parameters in tuning the switch behavior of an aptaSwitch.

In another embodiment, an aptaSwitch of the invention is employed to target the effector domain to certain environments, e.g., a particular cell type or tissue, or a particular intracellular location or cell membrane. The tissue or cell type-targeting may be conferred by the tissue or cell type-specificity of the ligand. In other embodiments, the activity of the aptaSwitch of the invention is modulated in an environmental-specific manner, wherein the activity of the aptaSwitch is specific to a particular cell type or tissue, or a particular intracellular location. Environmental-specific activities of aptaSwitches may be conferred by ligands specific to a specific local environment.

In certain embodiments, aptaSwitches comprise multiple modular components, e.g., one or more aptamer domains and/or one or more effector domains. In other embodiments, an aptaSwitch of the invention interacts with and responds to multiple ligands. For instance, aptaSwitches may comprise an aptamer domain that responds to multiple ligands, or may comprise more than one aptamer domain that each respond to a ligand. Optionally, one or more effector domains are modulated by the one or more aptamer domains that respond to multiple ligands. In a specific aspect, a cooperative ligand controlled nucleic acid is provided, wherein multiple ligands sequentially bind to multiple aptamer domains to allosterically regulate one or more effector domains. aptaSwitches comprising multiple modular components are useful for processing multiple biomolecular inputs.

In certain embodiments, aptaSwitches further comprise a functional group or a functional agent, e.g., an intercalator or an alkylating agent.

Still other aspects of the invention provide a library of aptamer-regulated nucleic acids, such as libraries having a variegated population of nucleic acids having different aptamers and/or different effector regions (such as substrate sequences, antisense sequences or targeting sequences as described above). These libraries may have diversity among the aptamers with respect to the types of ligands that can be bound (specificity) and/or the variation in affinity for the same ligand.

Still another aspect of the present invention relates to cells which include one or more aptaSwitches of the present invention, or which have been engineered with one or more expression constructs for producing aptaSwitches in the cell.

For instance, in one embodiment, the cell includes a metabolic pathway of one or more reactions, and one or more aptaSwitches that act as control elements on the metabolic pathway. Each of these aptaSwitches can include (i) an aptamer sequence that selectively binds to a ligand selected from an enzyme co-factor, a reactant, a substrate or a product of a reaction in the metabolic pathway, (ii) a gene silencing sequence for reducing expression of a target gene encoding a protein involved in the metabolic pathway. These may be proteins that act as enzymes in the pathway, or may be proteins that act as regulatory subunits or have other effects on the pathway (such as transcription factors or repressors that control expression of components of the metabolic pathway). In these embodiments, ligand binding to the aptamer causes a change in the trans-acting nucleic acid between two conformation states, in one of which the trans-acting nucleic acid inhibits expression of the target gene in a manner dependent on the gene silencing sequence, and in the other of which the trans-acting nucleic acid does not inhibit expression of the target gene. Thus, the metabolic pathway can be regulated at least in part by the trans-acting nucleic acid. In certain preferred instances, the metabolic pathway includes at least one reaction mediated by an enzyme, and at least one of the trans-acting nucleic acid regulates expression of the enzyme.

It will be evident that there are many potential uses for the subject aptaSwitch. To illustrate another, the present invention contemplates a method for rendering expression of a target gene in a cell dependent on the presence or absence of a ligand. This method involves introducing into the cell an aptaSwitch having, for example, a (i) a targeting sequence that is capable of hybridizing to the target gene and regulate expression of the target gene; and (ii) an aptamer sequence that binds to a ligand. Binding of the ligand to the aptamer induces a conformational change in the trans-acting nucleic acid, and the trans-acting nucleic acid regulates expression of the target gene in a dose-dependent manner dependent on the concentration of the ligand.

In certain embodiments, the ligand can be a molecule produced by the cell. In other embodiments, the ligand can be a cell permeable agent that is contacted with the cell, e.g., either by ectopic addition or by diffusion from a neighboring cell.

There are a variety of embodiments of targeting sequences for accomplishing ligand-mediated regulation of target gene expression. In one instance, the targeting sequence inhibits expression of the target gene through an antisense mechanism of action, and is available for hybridization with the target gene in a manner dependent upon the ligand-induced conformational change. In other embodiments, the targeting sequence inhibits expression of the target gene through an RNA Interference mechanism of action, and becomes a substrate for an RNAse III enzyme in a manner dependent upon the ligand-induced conformational change. In still other embodiments, the targeting sequence inhibits expression of the target gene through homologous recombination with the target gene, and becomes a substrate for recombinase in a manner dependent upon the ligand-induced conformational change.

Another application of the aptaSwitches of the present invention includes a method of determining the amount of an analyte in a cell. For instance, an aptaSwitch can be introduced into the cell (e.g., directly or through transcription from an expression construct), this aptaSwitch may include a targeting sequence that is capable of hybridizing to a reporter gene and regulate expression of the reporter gene, and an aptamer sequence that binds to the analyte. Binding of the analyte to the aptamer induces a conformational change in the trans-acting nucleic acid, and the trans-acting nucleic acid regulates expression of the reporter gene in a manner dependent on the concentration of the analyte. Thus, measuring the amount of expression of the reporter gene and correlating the amount of expression of the reporter gene with the amount of analyte can be used to determine the amount of the ligand in the cell. The reporter gene can be an endogenous gene or can be a heterologous gene.

Another aspect of the invention provides a method of modulating the amount and/or activity of a ligand in a cell. The method may comprise designing and selecting an aptamer responsive to the ligand of interest and providing an aptamer-regulated nucleic acid comprising the selected aptamer domain and an effector domain. An aptamer-regulated nucleic acid may be used to modulate the amount and/or activity of a ligand to which the aptamer-regulated nucleic acid is responsive, such as in a positive or negative feedback loop. The effector RNA domain of an aptamer-regulated nucleic acid is targeted to a molecule or protein, for example, in a signaling or metabolic pathway in the cell that involves the ligand. For example, the effector RNA domain may be targeted to a metabolite, intermediate molecule, or enzyme that affects the production or activity of the ligand of interest. The method may further comprise contacting a cell with the aptamer-regulated nucleic acid in an amount and/or for a time period, when switched on, sufficient for modulating the concentration and/or activity of the ligand in the cell.

In another embodiment, an aptamer-regulated nucleic acid of the invention is an in vivo sensor that indicates the intracellular amount or concentration of a ligand. For example, a ligand that interacts with the aptamer domain of an aptamer-regulated nucleic acid modulates the effector domain of the aptamer-regulated nucleic acid, wherein the effector domain modulates the amount and/or activity of a "reporter" molecule. The reporter molecule is activated or repressed by its interaction with the effector domain. The amount or activity of the reporter molecule, therefore, correlates with the amount or concentration of the ligand of interest. Exemplary reporter molecules include, without limitation, fluorescent or luminescent reporter proteins such as green fluorescent protein (GFP) or luciferase, enzymatic reporters such as alkaline phosphatase, or colorimetric reporters such as lacZ.

In another embodiment, the invention provides a method of modulating a biological or biochemical response of a cell in response to the presence or absence of an amount or activity of a ligand. For example, a ligand that interacts with the aptamer domain of an aptamer-regulated nucleic acid modulates the effector domain of the aptamer-regulated nucleic acid, wherein the effector domain is targeted to a gene that modulates a biological or biochemical response of a cell. The method may comprise designing and selecting an aptamer responsive to a ligand and providing an aptamer-regulated nucleic acid that comprises the selected aptamer domain and an effector domain that targets a gene that modulates a biological or biochemical response of a cell The method may further comprise contacting a cell with the aptamer-regulated nucleic acid in an amount and/or for a time period, when switched on, sufficient for modulating the biological or biochemical response of the cell.

Certain embodiments are also directed to a method of establishing a conditional genetic network. The method may comprise providing an aptamer-regulated nucleic acid that comprises an aptamer domain and an effector domain, wherein the aptamer domain is responsive to a ligand and the effector domain is targeted to a molecule that is unassociated with a signaling, metabolic, enzymatic, or any biochemical pathway that produces the ligand or modulates the activity of the ligand. The method further comprises contacting the cell with the aptamer-regulated nucleic acid in an effective amount and/or for a sufficient time period, when switched on, that modulates expression of the target molecule, thereby establishing a conditional genetic network. A conditional genetic network may be useful, for example, in engineering an intracellular signaling network.

Further provided is a method of attenuating or modulating expression of an endogenous or heterologous target gene in a cell, comprising contacting the cell with an aptamer-regulated nucleic acid in an amount sufficient to attenuate or modulate expression of the target gene. The effector domain is specific to the target gene and the aptamer domain is responsive to a ligand. In response to ligand binding to the aptamer domain, an allosteric change occurs in the effector domain which makes the effector domain available to regulate the target gene. The aptamer-regulated nucleic acid of the invention, therefore, acts as a switch whose activity is turned "on" and "off" in response to ligand binding. Such methods are useful for altering the growth, division, survival, or differentiation of cells that are treated with an aptamer-regulated nucleic acid of the invention. In certain embodiments, the method is employed for treatment of cells in vivo or in vitro. In certain embodiments, the method is employed for treatment of cells in vivo or in vitro.

Certain embodiments provide a method of tissue or cell type-specific modulation of the concentration and/or activity of a ligand or the expression of a target gene. The tissue or cell type-specific modulation may be achieved by the tissue or cell type-specific presence of the ligand. For example, the aptamer domain of an aptamer-regulated nucleic acid is responsive to a tissue or cell type-specific ligand and the effector domain targets a ligand to modulate the concentration and/or activity of the ligand. In another aspect, the aptamer domain of an aptamer-regulated nucleic acid is responsive to a tissue or cell type-specific ligand and the effector domain targets a target gene to modulate the expression of the target gene.

Yet another example of a use of the present invention relates to a method for treating or preventing infection by a pathogenic agent. Such methods would include administering to a patient a sufficient amount of an aptaSwitch that regulated genes expressed by the pathogen or by the host patient that effect, for example, the infectivity or virulence of the pathogen. For instance, the trans-acting nucleic acid can include (i) a targeting sequence that is capable of hybridizing to a target gene of the pathogen or patient and regulate expression of the target gene, i.e., a target gene is essential for maintenance, integration, replication, virulence or spread of infection by the pathogen; and (ii) an aptamer sequence that binds to a ligand, the concentration of which is dependent on the presence of the pathogen. Binding of the ligand to the aptamer induces a conformational change in the nucleic acid, and the nucleic acid regulates expression of the target gene in a manner dependent on the ligand-induced conformational change and reduces or inhibits infection by the pathogen.

Still another example of an application of the present invention is for a method to cause phenotypic regulation of cell growth, differentiation or viability in cells of a patient. Such a method can include introducing into cells in the patient a trans-acting nucleic acid comprising: (i) a targeting sequence that is capable of hybridizing to a target gene in the cells of the patient and regulate expression of the target gene, wherein expression of the target gene alters cell growth, differentiation or viability; and (ii) an aptamer sequence that binds to a ligand, the concentration of which is dependent on cellular phenotype. In this instance, binding of the ligand to the aptamer induces a conformational change in the nucleic acid, and the nucleic acid regulates expression of the target gene in a manner dependent on the ligand-induced conformational change so as to alter cell growth, differentiation or viability relative to the absence of the ligand. The aptaSwitch(s) can be selected to either induce or prevent cell death, induce or inhibit differentiation, or induce or inhibit proliferation of the cells in a manner dependent on the presence of the ligand.

Merely for illustration, the method can be used prevent the growth of hyperplastic or tumor cells, or even the unwanted proliferation of normal cells. It can be used to induce the death of fat cells. It can also be used to regulate growth and differentiation of stem cells, or to regulate activation of an immune response.

In certain embodiments, the aptaSwitch or expression construct encoding an aptaSwitch can be introduced into cells ex vivo, and the cells transplanted into a patient. In other embodiments, the aptaSwitch or expression construct is delivered to the cells in vivo.

Another aspect of the invention provides for a pharmaceutical preparation composition including a trans-acting nucleic acid of the present invention along with a pharmaceutically acceptable carrier, such that the formulation is suitable for administration to a human or non-human patient. Optionally, the pharmaceutically acceptable carrier is selected from pharmaceutically acceptable salts, ester, and salts of such esters. In certain preferred embodiments, the present invention provides a pharmaceutical package or kit comprising the pharmaceutical preparation which includes at least one aptamer-regulated nucleic acid and a pharmaceutically acceptable carrier, in association with instructions (written and/or pictorial) for administering the preparation to a human patient.

A further aspect of the invention provides a composition comprising an aptamer-regulated nucleic acid in an amount sufficient to modulate expression of a target gene in treated cells and a pharmaceutically acceptable carrier, wherein the aptamer-regulated nucleic acid comprises an aptamer domain and an effector RNA domain, wherein the aptamer domain is responsive to a ligand. Upon ligand binding to the aptamer domain, an allosteric change occurs in the effector domain, thereby modulating the activity of the effector domain. The composition may be employed for treatment of cells in vitro or in vivo.

In certain embodiments, the aptamer-regulated nucleic acid is introduced to cells, in vivo, by contacting the cells with an expression vector having a nucleic acid coding sequence that is transcribed to produce one or more products that produce the aptamer-regulated nucleic acid in the treated cells. In other embodiments, the aptamer-regulated nucleic acid is introduced to cells ex vivo. For example, the aptamer-regulated nucleic acid may be introduced to cells outside of a subject by contacting the cells with an expression vector having a nucleic acid coding sequence that is transcribed to produce one or more products that produce the aptamer-regulated nucleic acid in the treated cells. The cells that are transfected with the aptamer-regulated nucleic acid can then be introduced into a subject for treatment. The cells used in ex vivo treatment strategies may be derived from the subject to be treated, from a donor, or from a previously generated stock of maintained cells. Cells that may be used in ex vivo treatment strategies include, but are not limited to, stem cells, somatic cells, and immune cells (e.g., T cells). In a specific embodiment, the invention provides a method for modulating the differentiation of a stem cell, comprising transfecting a stem cell with an aptamer-regulated nucleic acid of the invention, wherein the aptamer-regulated nucleic acid comprises an aptamer domain and an effector RNA domain. The aptamer domain is responsive to the binding of a ligand and the effector domain is targeted to a molecule or gene that is sufficient to modulate the differentiation of a stem cell. Stem cells may be differentiated into any cell type (e.g., a dermal cell, hepatocytes, retinal cells, etc.).

The methods described herein may employ an expression vector having a coding sequence that is transcribed to produce one or more transcriptional products that produce an aptamer-regulated nucleic acid in the treated cells. For example, the expression vector is selected from an episomal expression vector, an integrative expression vector, and a viral expression vector. In another preferred embodiment, the aptamer-regulated nucleic acid comprises a hairpin RNA which is processed to a siRNA in the treated cells.

Still another aspect of the present invention provides a method for inhibiting cell growth or proliferation in vivo, comprising administering to an animal an aptamer-regulated nucleic acid of sufficient amount to reduce expression of a target gene essential to mitosis of a cell. In another aspect, the aptamer-regulated nucleic acid is administered to an animal in a sufficient amount to reduce expression of a target gene that is essential to preventing apoptosis of a cell. In a preferred embodiment, the animal is a human patient.

In certain preferred embodiments, the effector domain of an aptamer-regulated nucleic acid targets an oncogene. Exemplary oncogenes include, without limitation, c-myc, c-myb, mdm2, PKA-I, Abl-1, Bcl2, Ras, c-Raf kinase, CDC25 phosphatases, cyclins, cyclin dependent kinases, telomerase, PDGF/sis, erb-B, fos, jun, mos, src or the Bcr/Abl fusion gene. In certain embodiments, the cell is a transformed cell so that the aptamer-regulated nucleic acid is used for the treatment of hyperplastic cell growth, including treatment of a cancer. In other embodiments, the aptamer-regulated nucleic acid is used for inhibiting activation of lymphocytes, including treatment or prophylaxis of immune-mediated inflammatory disorders. In still other embodiments, the aptamer-regulated nucleic acid is used for inhibiting proliferation of smooth muscle cells, including treatment or prophylaxis of restenosis. In yet other embodiments, the aptamer-regulated nucleic acid is used for inhibiting proliferation of epithelial cells (e.g., as a component of cosmetic preparations).

In another embodiment, the invention provides a method for treating an infectious disease, comprising administering to an animal an aptamer-regulated nucleic acid comprising an effector domain that inhibits the expression of a target pathogen and/or host gene that is essential for the maintenance, replication, or spread of pathogenic infection and an aptamer domain that binds to a ligand. Binding of the ligand to the aptamer domain causes a conformational change in the nucleic acid that alters the ability of the effector domain to inhibit the expression of the target gene. The nucleic acid is administered in a sufficient amount to inhibit the expression of pathogen and/or host genes that are important for the maintenance, replication, or spread of pathogenic infection. For example, the aptamer domain of an aptamer-regulated nucleic acid can bind and respond to infection products (e.g., HIV gag, p24, p6, p7, p17, gp120, gp41, pol, env, tat, rev, nef, vif, vpr, vpu, and tev proteins) that are generated upon pathogen infection. Ligand binding to the aptamer domain causes a conformational change in the nucleic acid so that the effector domain is available to target pathogen and/or host genes that are important for the maintenance or spread of pathogenic infection. Pathogens include, viral, eukaryotic and prokaryotic organisms, including pathogenic viruses, bacteria, and fungi.

Still another aspect of the present invention provides a method of conducting a pharmaceutical business comprising: (a) identifying an aptamer-regulated nucleic acid which, when switched "on," inhibits proliferation of target cells in vivo and reduces the effects of a disorder involving unwanted proliferation of the target cells; (b) conducting therapeutic profiling of the an aptamer-regulated nucleic acid identified in step (a) for efficacy and toxicity in animals; and (c) formulating a pharmaceutical preparation including one or more of the aptamer-regulated nucleic acids identified in step (b) as having an acceptable therapeutic profile.

The method of conducting a pharmaceutical business may further comprise an additional step of establishing a distribution system for distributing the pharmaceutical preparation for sale, and optionally, establishing a sales group for marketing the pharmaceutical preparation.

Yet still another aspect of the present invention provides a method of conducting a pharmaceutical business comprising: (a) identifying an aptamer-regulated nucleic acid which, when switched "on," inhibits proliferation of target cells in vivo and reduces the effects of a disorder involving unwanted proliferation of the target cells; (b) (optionally) conducting therapeutic profiling of aptamer-regulated nucleic acid identified in step (a) for efficacy and toxicity in animals; and (c) licensing, to a third party, the rights for further development of the aptamer-regulated nucleic acid.

The skilled artisan recognizes that an aptamer-regulated nucleic acid that is useful for treating any disorder, including, but not limited to inhibiting pathogenic replication and/or infection, regulation of the immune response, or modulation of the cellular state of a cell, may be used in the methods of conducting a pharmaceutical business as described herein.

Further aspects of invention relate to applications of a ligand controlled nucleic acid molecule in different fields. For example, an aptamer-regulated nucleic acid can be employed as an in vivo sensor to detect the presence, absence, or amount of a molecule in a sample. For example, an aptamer-regulated nucleic acid may comprise an aptamer domain that binds to a ligand molecule of interest and an effector domain that modulates a reporter molecule to indicate the presence, absence, or amount of the ligand molecule. A ligand molecule may be any of the ligands as described herein, such as small molecules, proteins, and natural or synthetic polymers. Alternatively, the aptamer-regulated nucleic acid may respond to environmental changes such as temperature, pH, or salt concentration. The reporter molecule may be measured by fluorescent, chemical, or enzymatic means. An aptamer-regulated nucleic acid can similarly be employed for imaging purposes.

The ligand controlled nucleic acid may comprise an aptamer domain that is responsive to the target molecule (such a target molecule is also termed a ligand for the aptamer domain), and the aptamer domain may be designed and selected according to the identity of the target molecule. Target molecules may include natural and synthetic polymers, including proteins, peptides, nucleic acids, polysaccharides, glycoproteins, receptors and cell surfaces. Alternatively target molecules may also include small molecules such as drugs, hormones, metabolites, intermediates, cofactors, transition state analogs, ions, metals, nucleic acids, and toxins.

BRIEF DESCRIPTION OF THE DRAWINGS

FIG. 1a is a general illustration of the mechanism by which an antiswitch molecule acts to regulate gene expression in vivo. 1, antisense sequence; 2, switching "aptamer stem". In the absence of effector, the antisense domain is bound in a double-stranded region of the RNA referred to as the "antisense stem" and the antiswitch is in the "off" state. In this state the antiswitch is unable to bind to its target transcript, which encodes a gfp coding region, and as a result, GFP production is on. In the presence of effector, the antiswitch binds the molecule, forcing the aptamer stem to form, switching its confirmation to the "on" state. In this state the antisense domain of the antiswitch will bind to its target transcript and through an antisense mechanism turn the production of GFP off. FIG. 1b shows the sequence and predicted structural switching of a theophylline-responsive antiswitch, s1 (SEQ ID NO: 1), and its target Mrna (SEQ ID NO: 17). 3, antisense sequence; 4, switching aptamer stem sequence; 5, start codon on the target mRNA. The stability of each switching stem is indicated. FIG. 1c shows in vivo GFP regulation activity of s1 and controls across different effector concentrations: aptamer construct (negative control) in the presence of theophylline; antisense construct (positive control) in the presence of theophylline; s1 in the presence of caffeine (negative control); s1 in the presence of theophylline. Data is presented as relative, normalized GFP expression in cells harboring these constructs against expression levels from induced and uninduced cells harboring only the GFP expression construct. FIG. 1d shows in vivo temporal response of s1 inhibiting GFP expression upon addition of effector to cells that have accumulated steady-state levels of GFP and antiswitch s1: no theophylline (−); 2 mM theophylline (+). FIG. 1e shows in vitro affinity assays of s1 to target and effector molecules. The mobility of radiolabeled s1 was monitored in the presence of equimolar concentrations of target transcript and varying concentrations of theophylline as indicated.

FIG. 2a shows the predicted structures of tuned antiswitches (s2-s4) (SEQ ID NOs: 2-4, respectively), based on s1 (SEQ ID NO: 1), in the absence of theophylline binding. 6, antisense sequences; 7, switching aptamer stem sequences; 8, modified sequences. The stability of each switching stem is indicated. FIG. 2b shows in vivo GFP regulation activity of s1-s4 across different theophylline concentrations: s1—initial antiswitch construct; s2—destabilized antiswitch construct; s3—stabilized antiswitch construct; s4—destabilized antiswitch construct.

FIG. 3a shows in vivo GFP regulation activity of modified aptamer-antiswitch constructs (s5-s6) across different theophylline concentrations: s1—initial antiswitch construct; s5—antiswitch construct with an aptamer domain having 10-fold lower affinity to theophylline than that used in s1; s6—destabilized modified aptamer-antiswitch construct, based on s5. FIG. 3b shows in vivo GFP regulation activity of antiswitch constructs responsive to different small molecule effectors (s1, s7) across different effector concentrations: s1—initial antiswitch construct responsive to theophylline; s7—antiswitch construct modified with a tetracycline aptamer domain, based on s1, responsive to tetracycline.

FIG. 4a shows the sequence and structural switching of an "on" antiswitch regulator (s8) (SEQ ID NO: 8) responsive to theophylline. 9, antisense sequence; 10, switching aptamer stem sequence; 11, start codon on the target mRNA. The stability of each switching stem is indicated. s8 is designed such that in the absence of theophylline the antiswitch is "on" or the antisense domain is free to bind to its target (SEQ ID NO: 17). In the presence of theophylline, the antiswitch undergoes a conformational change to the "off" state such that the antisense domain is bound in a double-stranded RNA stem that is part of the aptamer stem. FIG. 4b shows in vivo GFP regulation activity of "on" and "off" antiswitch constructs across different theophylline concentrations: s1—initial "off" antiswitch construct; s8—redesigned "on" antiswitch construct, based on s1.

FIG. 5a illustrates the mechanism by which two independent antiswitch molecules act to regulate the expression of multiple target genes in vivo. In the absence of their respective effectors, the antiswitches are in the "off" state and are unable to bind to their target transcripts. In this state, both GFP and YFP production is on. In the presence of theophylline, one antiswitch switches its conformation to the "on" state and turns off GFP production. In the presence of tetracycline, the second antiswitch switches its conformation to the "on" state and turns off YFP production. These antiswitches act independently of each other to provide combinatorial control over genetic circuits. FIG. 5b shows in vivo regulation activity of two antiswitch constructs (s1, s9) against their respective targets (GFP, YFP) in the presence or absence of their respective effector molecules (theophylline, tetracycline).

FIG. 8 shows the sequences and predicted structures of antiswitches s5 (SEQ ID NO: 5), s6 (SEQ ID NO: 6), and s7 (SEQ ID NO: 7) in the absence of ligand binding. 13, antisense sequences; 14, switching aptamer stem sequences; 15, modified sequences. The stability of each stem section is indicated. s1—modified theophylline aptamer antiswitch based on s1; s6—destabilized modified theophylline aptamer antiswitch; s7—tetracycline aptamer antiswitch based on s1.

FIG. 11 shows relative RNA levels of target mRNA and antiswitch s1. Relative levels are normalized to GFP mRNA levels in the absence of theophylline.

FIG. 12 shows a list of plasmids that may be used in the invention.

FIG. 13 shows exemplary sequences of antiswitch constructs, controls, and qRT-PCR primers that may be used in the invention. Sequences are shown 5' to 3' and represented in their RNA form (SEQ ID NOs: 1-16, respectively).

In FIG. 17a, the switch is "on" in the absence of ligand and "off" with ligand binding. In FIG. 17b, the switch is "off" in the absence of ligand and activated to the "on" conformation with ligand binding. In both cases, the activated state presents the effector domain and sense strand in a configuration that makes the domain available for cleavage by Dicer. The cleaved product functions in RNAi mechanisms for regulating target activity In FIG. 18a, the switch is "on" in the absence of ligand and "off" with ligand binding. In FIG. 18b, the switch is "off" in the absence of ligand and activated to the "on" conformation with ligand binding.

FIG. 19a shows that theophylline concentration affects binding of the switch and sense strand. Theophylline binding to the switch results in decreased binding of the switch and sense strand. FIG. 19b shows Dicer-dependent cleavage of the switch and sense strand. The 5' end radiolabeled microswitch and sense strand were incubated either in the presence or absence of recombinant Dicer for 16 hours in varying concentrations of theophylline and then separated on a 12% nondenaturing polyacrylamide gel. FIG. 19c shows a schematic of the Dicer-dependent switch mechanism. The switch is "on" in the absence of ligand.

FIG. 20a is a graph showing data that reflects transfection of 10 nM microswitch and sense strand into HeLa cells growing in varying concentrations of theophylline. Theophylline binding causes an "off" switch. The switch is "on" in lower theophylline concentrations, which causes RNAi mediated attenutation of GFP expression. Error bars represent two independent measurements. FIG. 20b shows a schematic of the Dicer-dependent switch mechanism, where the switch is "on" in the absence of ligand.

In FIG. 21a, the switch is "on" in the absence of ligand and "off" with ligand binding. In FIG. 21b, the switch is "off" in the absence of ligand and activated to the "on" conformation with ligand binding. In both cases, the activated state presents the effector domain and sense strand in a configuration that makes the domain available for cleavage by Dicer. The cleaved product functions in RNAi mechanisms for regulating target activity.

DETAILED DESCRIPTION OF THE INVENTION

1. Overview

Figure 1A:
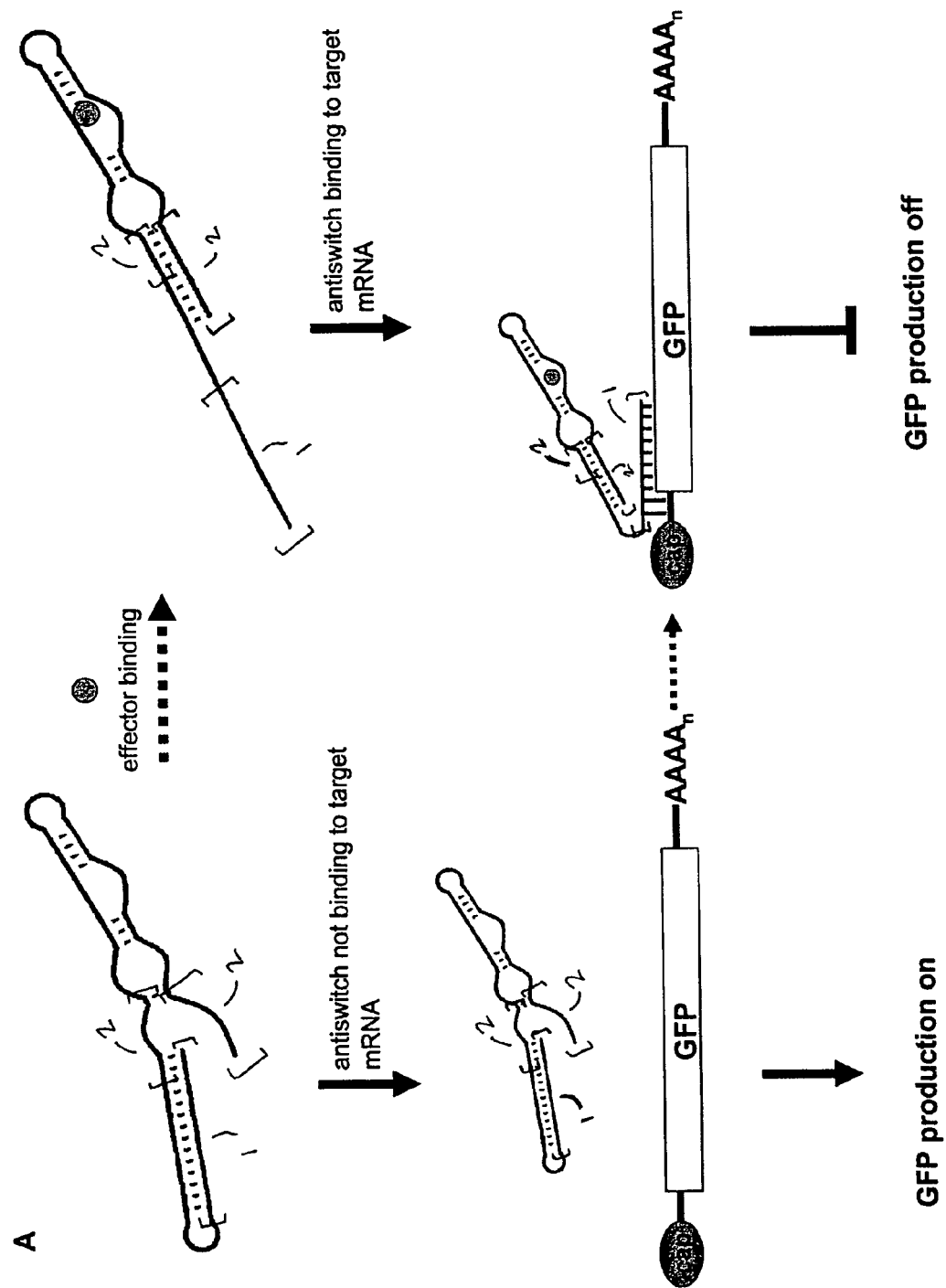
FIGS. 1a-1e illustrate the design and functional activity of a novel antiswitch regulator.

The present invention provides trans-acting aptamer-regulated nucleic acids, or "aptaSwitches," that respond to ligand binding. One aspect relates to aptamer-regulated nucleic acids and methods and compositions comprising these aptamer-regulated nucleic acids for modulating (e.g., attenuating) gene expression in a cell. Another aspect relates to aptamer-regulated nucleic acids that may be employed as in vivo sensors to detect the presence, absence, or amount of a molecule in a sample. By trans-acting, it is meant that the aptaSwitches of the present inventions exert their ligand-dependent activity on a molecule, e.g. another nucleic acid, that is different from the aptaSwitch, e.g. not linker through a phosophodiester (or equivalent) backbone linker, and even more preferably not covalently linked to the aptaSwitch at all.

Thus, one aspect of the present invention provides engineered, aptamer-regulated nucleic acids that are powerful, allosteric regulators of gene expression. A general design of an aptamer-regulated nucleic acid is based on conformational dynamics of nucleic acid folding to create a dual stem molecule comprised of an effector stem and an aptamer stem. These stems are preferably designed such that in the absence of ligand, the free energy of the effector stem is lower than that of the aptamer stem. Ligand and target act cooperatively to alter the conformational dynamics of these molecules and stabilize the formation of the aptamer stem and the binding of the effector RNA domain to its target transcript. The aptamer-regulated nucleic acid platform is flexible, enabling both positive and negative regulation. The "on" switch is designed using the same energetics on an altered platform such that in the absence or low levels of ligand the effector RNA domain is free to bind to the target; however ligand binding changes the conformational dynamics of these molecules so that the effector RNA domain is bound in the aptamer stem.

The switching dynamics of aptamer-regulated nucleic acids are amenable to tuning by forward engineering design strategies based on thermodynamic properties of nucleic acids. Altering the free energy of the effector domain alters the conformational dynamics of these molecules in a predictable fashion. Specifically, decreasing the stability of the effector stem decreases the ligand concentration necessary to induce a conformational change in an aptamer-regulated nucleic acid and increasing the stability of the effector stem increases the ligand concentration necessary to induce the conformational change. Decreasing the stability of the effector stem also shifts the dynamics to favor the "off" state at low ligand levels.

In addition, the aptamer-regulated nucleic acid platform is fully modular, enabling ligand response and transcript targeting to be engineered by swapping domains within the aptamer-regulated nucleic acid. This provides a platform for the construction of tailor-made aptamer-regulated nucleic acids for a variety of different ligands. Ligand binding of the aptamer domain in aptamer-regulated nucleic acids is designed separately from the targeting capability of the effector domain by swapping only the aptamer domain. Likewise, the targeting capability of the effector domain can be designed separately from the ligand binding of the aptamer domain by swapping the effector domain so that a different gene or molecule is targeted without affecting the aptamer domain. Aptamer-regulated nucleic acids present a powerful, flexible method of tailoring spatial and temporal gene expression in both natural and engineered contexts.

In certain embodiments, aptamer-regulated nucleic acids comprise multiple modular components, e.g., one or more aptamer domains and/or one or more effector domains. In other embodiments, an aptamer-regulated nucleic acid of the invention interacts with and responds to multiple ligands. For instance, aptamer-regulated nucleic acids may comprise an aptamer domain that responds to multiple ligands, or may comprise more than one aptamer domain that each respond to a ligand. Optionally, one or more effector domains are modulated by the one or more aptamer domains that respond to multiple ligands. In a specific aspect, a cooperative ligand controlled nucleic acid is provided, wherein multiple ligands sequentially bind to multiple aptamer domains to allosterically regulate one or more effector domains. Aptamer-regulated nucleic acids comprising multiple modular components are useful for processing multiple biomolecular inputs and the generation of cooperative aptamer-regulated nucleic acids. For instance, an aptamer-regulated nucleic acid may bind to two or more different ligands. Aptamer-regulated nucleic acid may be configured so that it only modulates a target gene (e.g., a gene of interest or a reporter gene such as green fluorescent protein or beta-galactosidase) in response to the binding of both ligands, or to neither of the two ligands. In aptamer-regulated nucleic acids that bind to two or more ligands, the binding of a first ligand may increase the capacity for the aptamer to bind the second ligand.

Aptamer-regulated nucleic acids are novel, allosteric regulators of gene expression that can potentially function across a diverse range of organisms, from prokaryotes to humans, making them extremely useful in many different applications. Aptamer-regulated nucleic acids presents a powerful tool for gene therapy applications, where one would like to target specific transcripts in response to specific cellular environments that are indicative of a diseased state (Watkins et al., *Curr Opin Mol Ther* 4, 224-8 (2002)). As emerging technologies enable the metabolic profiling of disease states (Koch, *J Biol Chem* 219, 181-8 (1956)), aptamer-regulated nucleic acids can be designed to respond to various metabolic markers. For instance, aptamer-regulated nucleic acids can be constructed to inhibit genes necessary for cell growth and division in response to oncogenic proteins or isoforms. One can also anticipate an exogenously delivered aptamer-regulated nucleic acid comprising an effector domain that is an antisense construct acting as a therapeutic molecule, similar to exogenously delivered antisense oligonucleotides, thereby extending the functionality of current antisense therapies by introducing ligand-specific or cell type-specific action to an already highly targeted therapy. Similar extensions of the current RNAi technologies can also be anticipated with the aptamer-regulated nucleic acids described herein.

Aptamer-regulated nucleic acids can further be used to engineer novel regulatory pathways and control loops for applications in metabolic engineering (Khosla et al., *Nat Rev Drug Discov* 2, 1019-25 (2003)) and synthetic circuit design (Kobayashi et al., *Proc Natl Acad Sci USA* 101, 8414-9 (2004)) by enabling the cell to sense and respond to intracellular metabolite levels and environmental signals. Because aptamer-regulated nucleic acids activity is tunable over a range of ligand concentrations, switches can be designed to inhibit or activate genes only when certain metabolites exceed or go below certain concentrations. Balancing heterologous gene expression in biosynthetic pathways (Berens et al., *Bioorg Med Chem* 9, 2549-56 (2001)) to maximize product yield can be achieved with aptamer-regulated nucleic acids that regulate expression of biosynthetic genes in response to pathway intermediate levels. Synthetic gene circuits have recently been used to understand and model cellular networks (Nagai et al., *Nat Biotechnol* 20, 87-90 (2002)) and to achieve cellular control as a step towards "programmable" cell behavior (Watkins et al., *Curr Opin Mol Ther* 4, 224-8 (2002)). Gene circuits can be built using combinations of aptamer-regulated nucleic acids as regulators for precise control schemes. Aptamer-regulated nucleic acids will be useful tools in building and characterizing circuits that accurately model natural regulatory pathways and yield further insight into these prevalent regulation schemes.

Finally, aptamer-regulated nucleic acids present new tools for cellular imaging, measuring, and detection strategies enabling programmable concentration-specific detection of intracellular molecules. Aptamer-regulated nucleic acids offer a unique platform to create tailor-made cellular sensors and "smart" regulators that potentially can target any gene in response to any target ligand, creating new avenues for cellular control and engineering.

2. Aptamer-Regulated Nucleic Acids

In one embodiment, an aptamer-regulated nucleic acid of the invention comprises an aptamer domain and an effector nucleic acid domain. An aptamer-regulated nucleic acid of the invention may comprise DNA or RNA and may be single-stranded or double-stranded. An aptamer-regulated nucleic acid may comprise multiple modular components, e.g., one or more aptamer domains and/or one or more effector domains. Aptamer-regulated nucleic acids may further comprise a functional group or a functional agent, e.g., an intercalator or an alkylating agent. Aptamer-regulated nucleic acids may comprise synthetic or non-natural nucleotides and analogs (e.g., 6-mercaptopurine, 5-fluorouracil, 5-iodo-2'-deoxyuridine and 6-thioguanine) or may include modified nucleic acids. Exemplary modifications include cytosine exocyclic amines, substitution of 5-bromo-uracil, backbone modifications, methylations, and unusual base-pairing combinations. Aptamer-regulated nucleic acids may include labels, such as fluorescent, radioactive, chemical, or enzymatic labels. An aptamer domain responds to ligand binding to induce an allosteric change in the effector domain, and alters the ability of the effector domain to interact with its target molecule. Ligand binding, therefore, switches the effector domain from "off" to "on," or vice versa. Aptamer-regulated nucleic acids, therefore, act as a switch whose activity is turned "off" and "on" in response to ligand binding. The response of the aptamer domain to the ligand may also depend on the ligand identity and/or the amount or concentration of ligand exposed to the aptamer domain. For example, an aptamer may bind small molecules, such as drugs, metabolites, intermediates, cofactors, transition state analogs, ions, metals, nucleic acids, and toxins. Alternatively, an aptamer may bind natural and synthetic polymers, including proteins, peptides, nucleic acids, polysaccharides, glycoproteins, hormones, receptors and cell surfaces such as cell walls and cell membranes. In certain other embodiments, the aptamer domain of a ligand controlled nucleic acid is responsive to environmental changes. Environmental changes include, but are not limited to changes in pH, temperature, osmolarity, or salt concentration. An effector nucleic acid domain may comprise an antisense nucleic acid or a DNA. An effector nucleic acid domain may also comprise a sequence that can be used as an RNAi sequence, such as a siRNA or miRNA. In preferred embodiments, ligand binding at the aptamer domain mediates a change in the conformational dynamics of these molecules that allows the effector nucleic acid domain to interact with a target nucleic acid, for example, an mRNA.

In one embodiment, the effector domain of an aptamer-regulated nucleic acid interacts with a target gene by nucleic acid hybridization. For instance, an aptamer-regulated nucleic acid may comprise an effector domain that comprises a hybridization sequence that hybridizes to a target sequence of a gene and an aptamer domain that binds to a ligand. The binding of the ligand to the aptamer domain causes a conformational change in the aptamer-regulated nucleic acid that alters the ability (such as availability and/or Tm) of the hybridization sequence of the effector domain to hybridize to a target sequence. Furthermore, an effector domain may modulate the expression or activity of its target by any method known in the art. In one embodiment, the effector domain of an aptamer-regulated nucleic acid comprises an effector domain that comprises an antisense sequence and acts through an antisense mechanism in modulating expression of a target gene. For instance, an aptamer-regulated nucleic acid may comprise an effector domain that comprises an antisense sequence for inhibiting expression of a target gene and an aptamer domain that binds to a ligand. The binding of the ligand to the aptamer domain causes a conformational change in the aptamer-regulated nucleic acid that alters the ability of the antisense sequence of the effector domain to inhibit expression of the target sequence.

In another embodiment, the effector domain of an aptamer-regulated nucleic acid comprises an effector domain that comprises an RNAi sequence and acts through an RNAi or miRNA mechanism in modulating expression of a target gene. For instance, an aptamer-regulated nucleic acid may comprise an effector domain that comprises a miRNA or siRNA sequence for inhibiting expression of a target gene and an aptamer domain that binds to a ligand. The binding of the ligand to the aptamer domain causes a conformational change in the aptamer-regulated nucleic acid that alters the ability of the miRNA or siRNA sequence of the effector domain to inhibit expression of the target sequence. In one embodiment, an effector domain comprises a miRNA or siRNA sequence that is between about 19 nucleotides and about 35 nucleotides in length, or preferably between about 25 nucleotides and about 35 nucleotides. In certain embodiments, the effector domain is a hairpin loop that may be processed by RNAse enzymes (e.g., Drosha and Dicer). As used herein, the term "RNAi" means an RNA-mediated mechanism for attenuating gene expression and includes small RNA-mediated silencing mechanisms. RNA-mediated silencing mechanisms include inhibition of mRNA translation and directed cleavage of targeted mRNAs. Recent evidence has suggested that certain RNAi constructs may also act through chromosomal silencing, i.e. at the genomic level, rather than, or in addition to, the MRNA level. Thus, the sequence targeted by the Effector domain can also be selected from untranscribed sequences that regulate transcription of a target gene of the genomic level.

The methods described herein may employ an expression vector having a coding sequence that is transcribed to produce one or more transcriptional products that produce an aptamer-regulated nucleic acid in the treated cells. Expression vectors appropriate for producing an aptamer-regulated nucleic acid are well-known in the art. For example, the expression vector is selected from an episomal expression vector, an integrative expression vector, and a viral expression vector. In another preferred embodiment, the aptamer-regulated nucleic acid comprises a hairpin RNA which is processed to an siRNA in the treated cells.

The invention further provides a class of in vivo nucleic acid sensors, for example, aptamer-regulated nucleic acids that directly sense the presence or amount an intracellular molecule through changes in nucleic acid conformation upon ligand binding to the aptamer domain of an aptamer-regulated nucleic acid. For example, a ligand that interacts with the aptamer domain of an aptamer-regulated nucleic acid switches "on" the effector domain of the aptamer-regulated nucleic acid. The activated effector domain then targets a "reporter" molecule. The reporter molecule is activated or repressed by its interaction with the effector domain. The amount or activity of the reporter molecule, therefore, correlates with the amount or concentration of the ligand of interest. Exemplary reporter molecules include, without limitation, fluorescent reporter proteins such as green fluorescent protein (GFP) or luciferase, enzymatic reporters such as alkaline phosphatase, or colorimetric reporters such as lacZ.

Aptamers

An "aptamer" may be a nucleic acid molecule, such as RNA or DNA that is capable of binding to a specific molecule with high affinity and specificity (Ellington et al., *Nature* 346, 818-22 (1990); and Tuerk et al., *Science* 249, 505-10 (1990)). Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes. The binding of a ligand to an aptamer, which is typically RNA, causes a conformational change in the effector domain and alters its ability to interact with its target molecule. Therefore, ligand binding affects the effector domain's ability to mediate gene inactivation, transcription, translation, or otherwise interfere with the normal activity of the target gene or mRNA, for example. An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants (Kd) of the aptamer for its ligand as compared to the dissociation constant of the aptamer for other materials in the environment or unrelated molecules in general. A ligand is one which binds to the aptamer with greater affinity than to unrelated material. Typically, the Kd for the aptamer with respect to its ligand will be at least about 10-fold less than the Kd for the aptamer with unrelated material or accompanying material in the environment. Even more preferably, the Kd will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all)

codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

Aptamers are readily made that bind to a wide variety of molecules. Each of these molecules can be used as a modulator of gene expression using the methods of the invention. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands in vitro aptamer selections (Werstuck and Green, *Science* 282:296-298 (1998)). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok, *Science* 9:324-9 (1999).

In certain embodiments, the ligand of the aptamer of an aptamer-regulated nucleic acid of the invention is a cell-permeable, small organic molecule. Small organic molecules which do not have a general inhibitory effect on translation are preferred as ligands. The small molecule preferably also exhibits in vivo persistence sufficient for achieving the desired level of inhibition of translation. The molecules also can be screened to identify those that are bioavailable after, for example, oral administration. In certain embodiments of the invention, the ligand is nontoxic. The ligand may optionally be a drug, including, for example, a steroid. However, in some of the methods of controlling gene expression, it is preferable that the ligand be pharmacologically inert. In some embodiments, the ligand is a polypeptide whose presence in the cell is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand may be a metal ion. In a specific embodiment, the aptamer domain of an aptamer-regulated nucleic acid responds to binding to caffeine.

The aptamer-regulated nucleic acid of the invention can be comprised entirely of RNA. In other embodiments of the invention, however, the aptamer-regulated nucleic acid can instead be comprised entirely of DNA, or partially of DNA, or partially of other nucleotide analogs. To specifically inhibit translation in vivo, aptamer-regulated RNAs are preferred. Such aptamer-regulated RNAs are preferably introduced into a cell as a DNA that encodes the aptamer-regulated nucleic acid sequence such that transcription results in the aptamer-regulated RNA. Alternatively, an aptamer-regulated RNA itself can be introduced into a cell.

Aptamers are typically developed to bind particular ligands by employing known in vivo or in vitro (most typically, in vitro) selection techniques known as SELEX (Ellington et al., *Nature* 346, 818-22 (1990); and Tuerk et al., *Science* 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present invention, the binding affinity of the aptamer for the ligand must be sufficiently strong and the structure formed by the aptamer when bound to its ligand must be significant enough so as to switch an aptamer-regulated nucleic acid of the invention between "on" and "off" states or tune the function level of an aptamer-regulated nucleic acid.

The association constant for the aptamer and associated ligand is preferably such that the ligand functions to bind to the aptamer and have the desired effect at the concentration of ligand obtained upon administration of the ligand. For in vivo use, for example, the association constant should be such that binding occurs well below the concentration of ligand that can be achieved in the serum or other tissue. Preferably, the required ligand concentration for in vivo use is also below that which could have undesired effects on the organism.

Antiswiches

An aptamer-regulated nucleic acid of the invention may comprise an effector domain that comprises an antisense sequence and acts through an antisense mechanism for inhibiting expression of a target gene. As used herein, such aptamer-regulated nucleic acids are also referred to as "antiswitches." Antisense technologies have been widely utilized to regulate gene expression (Buskirk et al., Chem Biol 11, 1157-63 (2004); and Weiss et al., Cell Mol Life Sci 55, 334-58 (1999)). As used herein, "antisense" technology refers to administration or in situ generation of molecules or their derivatives which specifically hybridize (e.g., bind) under cellular conditions, with the target nucleic acid of interest (mRNA and/or genomic DNA) encoding one or more of the target proteins so as to inhibit expression of that protein, e.g., by inhibiting transcription and/or translation, such as by steric hinderance, altering splicing, or inducing cleavage or other enzymatic inactivation of the transcript. The binding may be by conventional base pair complementarity, or, for example, in the case of binding to DNA duplexes, through specific interactions in the major groove of the double helix. In general, "antisense" technology refers to the range of techniques generally employed in the art, and includes any therapy that relies on specific binding to nucleic acid sequences.

An aptamer-regulated nucleic acid that comprises an antisense effector domain of the present invention can be delivered, for example, as a component of an expression plasmid which, when transcribed in the cell, produces an effector domain which is complementary to at least a unique portion of the target nucleic acid. Alternatively, the aptamer-regulated nucleic acid that comprises an antisense effector domain can be generated outside of the target cell, and which, when introduced into the target cell causes inhibition of expression by hybridizing with the target nucleic acid. Aptamer-regulated nucleic acids may be modified so that they are resistant to endogenous nucleases, e.g. exonucleases and/or endonucleases, and are therefore stable in vivo. Exemplary nucleic acid molecules for use in aptamer-regulated nucleic acids are phosphoramidate, phosphothioate and methylphosphonate analogs of DNA (see also U.S. Pat. Nos. 5,176,996; 5,264,564; and 5,256,775). General approaches to constructing oligomers useful in antisense technology have been reviewed, for example, by van der krol et al. (1988) Biotechniques 6:958-976; and Stein et al. (1988) Cancer Res 48:2659-2668.

Several considerations may be taken into account when constructing antisense effector domains for use in the compositions and methods of the invention: (1) antisense effector domains should have a GC content of 50% or more; (2) avoid sequences with stretches of 3 or more Gs; and (3) antisense effector domains should not be longer than 25-26 mers when in their "on" state and modulating a target gene. When testing an antisense effector domain, a mismatched control can be constructed. The controls can be generated by reversing the sequence order of the corresponding antisense oligonucleotide in order to conserve the same ratio of bases.

Antisense approaches involve the design of effector domains (either DNA or RNA) that are complementary to a target nucleic acid encoding a protein of interest. The antisense effector domain may bind to an mRNA transcript and prevent translation of a protein of interest. Absolute complementarity, although preferred, is not required. In the case of double-stranded antisense effector domains, a single strand of the duplex DNA may thus be tested, or triplex formation may be assayed. The ability to hybridize will depend on both the degree of complementarity and the length of the antisense sequence. Generally, the longer the hybridizing nucleic acid, the more base mismatches with a target nucleic acid it may contain and still form a stable duplex (or triplex, as the case may be). One skilled in the art can ascertain a tolerable degree of mismatch by use of standard procedures to determine the melting point of the hybridized complex.

Antisense effector domains that are complementary to the 5' end of an mRNA target, e.g., the 5' untranslated sequence up to and including the AUG initiation codon, should work most efficiently at inhibiting translation of the mRNA. However, sequences complementary to the 3' untranslated sequences of mRNAs have recently been shown to be effective at inhibiting translation of mRNAs as well (Wagner, R. 1994. Nature 372:333). Therefore, antisense effector domains complementary to either the 5' or 3' untranslated, non-coding regions of a target gene could be used in an antisense approach to inhibit translation of a target mRNA. Antisense effector domains complementary to the 5' untranslated region of an mRNA should include the complement of the AUG start codon. Antisense oligonucleotides complementary to mRNA coding regions are less efficient inhibitors of translation but could also be used in accordance with the invention. Whether designed to hybridize to the 5', 3', or coding region of mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antiswitch to inhibit expression of a target gene. It is preferred that these studies utilize controls that distinguish between antisense gene inhibition and nonspecific biological effects of antiswitches. It is also preferred that these studies compare levels of the target RNA or protein with that of an internal control RNA or protein. Additionally, it is envisioned that results obtained using the antiswitch are compared with those obtained using a control antiswitch. It is preferred that the control antiswitch is of approximately the same length as the test antiswitch and that the nucleotide sequence of the control antiswitch differs from the antisense sequence of interest no more than is necessary to prevent specific hybridization to the target sequence.

Antiswitches can be DNA or RNA or chimeric mixtures or derivatives or modified versions thereof, single-stranded or double-stranded. Antiswitches can be modified at the base moiety, sugar moiety, or phosphate backbone, for example, to improve stability of the molecule, hybridization, etc. Antiswitches may include other appended groups such as peptides (e.g., for targeting host cell receptors), or agents facilitating transport across the cell membrane (see, e.g., Letsinger et al., 1989, Proc Natl Acad Sci. USA 86:6553-6556; Lemaitre et al., 1987, Proc Natl Acad Sci. USA 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958-976) or intercalating agents. (See, e.g., Zon, Pharm. Res. 5:539-549 (1988)). To this end, an antiswitch may be conjugated to another molecule, e.g., a peptide, hybridization triggered cross-linking agent, transport agent, hybridization-triggered cleavage agent, etc.

An antiswitch may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl- 2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

An antiswitch may also comprise at least one modified sugar moiety selected from the group including but not limited to arabinose, 2-fluoroarabinose, xylulose, and hexose.

An antiswitch can also contain a neutral peptide-like backbone. Such molecules are termed peptide nucleic acid (PNA)-oligomers and are described, e.g., in Perry-O'Keefe et al. (1996) *Proc. Natl. Acad. Sci. USA* 93:14670 and in Eglom et al. (1993) *Nature* 365:566. One advantage of PNA oligomers is their capability to bind to complementary DNA essentially independently from the ionic strength of the medium due to the neutral backbone of the DNA. In yet another embodiment, an antiswitch comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, an antiswitch is an-anomeric oligonucleotide. An-anomeric oligonucleotide forms specific double-stranded hybrids with complementary RNA in which, contrary to the usual-units, the strands run parallel to each other (Gautier et al., 1987, *Nucl. Acids Res.* 15:6625-6641). The oligonucleotide is a 2'-O-methylribonucleotide (Inoue et al., 1987, *Nucl. Acids Res.* 15:6131-6148), or a chimeric RNA-DNA analogue (Inoue et al., 1987, *FEBS Lett.* 215:327-330).

Aptamer-regulated nucleic acids of the invention, including antiswitches, may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. *Nucl. Acids Res.* 16:3209 (1988)), methylphosphonate oligonucleotides can be prepared by use of controlled pore glass polymer supports (Sarin et al., *Proc. Natl. Acad. Sci. USA* 85:7448-7451 (1988)), etc.

While antisense sequences complementary to the coding region of an mRNA sequence can be used, those complementary to the transcribed untranslated region and to the region comprising the initiating methionine are most preferred.

Antiswitch nucleic acid molecules can be delivered to cells that express target genes in vivo. A number of methods have been developed for delivering nucleic acids into cells; e.g., they can be injected directly into the tissue site, or modified nucleic acids, designed to target the desired cells (e.g., antiswitches linked to peptides or antibodies that specifically bind receptors or antigens expressed on the target cell surface) can be administered systematically.

However, it may be difficult to achieve intracellular concentrations of the antiswitch sufficient to attenuate the activity of a target gene or mRNA or interest in certain instances. Therefore, another approach utilizes a recombinant DNA construct in which the antiswitch or other aptamer-regulated nucleic acid is placed under the control of a strong pol III or pol II promoter. The use of such a construct to transfect target cells in the patient will result in the transcription of sufficient amounts of antiswitches that will form complementary base pairs with the target gene or mRNA and thereby attenuate the activity of the protein of interest. For example, a vector can be introduced in vivo such that it is taken up by a cell and directs the transcription of an antiswitch. Such a vector can remain episomal or become chromosomally integrated, as long as it can be transcribed to produce the desired antiswitch. Such vectors can be constructed by recombinant DNA technology methods standard in the art. Vectors can be plasmid, viral, or others known in the art, used for replication and expression in mammalian cells. A promoter may be operably linked to the sequence encoding the antiswitch. Expression of the sequence encoding the antiswitch can be by any promoter known in the art to act in mammalian, preferably human cells. Such promoters can be inducible or constitutive. Such promoters include but are not limited to: the SV40 early promoter region (Bernoist and Chambon, *Nature* 290:304-310 (1981)), the promoter contained in the 3' long terminal repeat of Rous sarcoma virus (Yamamoto et al., *Cell* 22:787-797 (1980)), the herpes thymidine kinase promoter (Wagner et al., *Proc. Natl. Acad. Sci. USA* 78:1441-1445 (1981)), the regulatory sequences of the metallothionine gene (Brinster et al, *Nature* 296:3942 (1982)), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

RNAi Constructs—siRNAs and miRNAs

RNA interference (RNAi) is a phenomenon describing double-stranded (ds)RNA-dependent gene specific posttranscriptional silencing. Initial attempts to harness this phenomenon for experimental manipulation of mammalian cells were foiled by a robust and nonspecific antiviral defense mechanism activated in response to long dsRNA molecules. Gil et al. Apoptosis 2000, 5:107-114. The field was significantly advanced upon the demonstration that synthetic duplexes of 21 nucleotide RNAs could mediate gene specific RNAi in mammalian cells, without invoking generic antiviral defense mechanisms. Elbashir et al. Nature 2001, 411:494-498; Caplen et al. Proc Natl Acad Sci 2001, 98:9742-9747. As a result, small-interfering RNAs (siRNAs) and micro RNAs (miRNAs) have become powerful tools to dissect gene function. The chemical synthesis of small RNAs is one avenue that has produced promising results. Numerous groups have also sought the development of DNA-based vectors capable of generating such siRNA within cells. Several groups have recently attained this goal and published similar strategies that, in general, involve transcription of short hairpin (sh) RNAs that are efficiently processed to form siRNAs within cells. Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296: 550-553. These reports describe methods to generate siRNAs capable of specifically targeting numerous endogenously and exogenously expressed genes.

Accordingly, the present invention provides an aptamer-regulated nucleic acid comprising an effector RNA domain that comprises an RNAi sequence and acts through an RNAi or miRNA mechanism to attenuate expression of a target gene. For instance, an aptamer-regulated nucleic acid may comprise an effector domain that comprises a miRNA or siRNA sequence. In one embodiment, an effector domain comprises a miRNA or siRNA sequence that is between about 19 nucleotides and about 75 nucleotides in length, or preferably, between about 25 base pairs and about 35 base pairs in length. In certain embodiments, the effector domain is a hairpin loop that may be processed by RNAse enzymes (e.g., Drosha and Dicer).

An RNAi construct contains a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of aptamer-regulated nucleic acids that comprise an effector domain comprising RNAi sequences can be carried out by any of the methods for producing aptamer-regulated nucleic acids described herein. For example, an aptamer-regulated nucleic acid can be produced by chemical synthetic methods or by recombinant nucleic acid techniques. Endogenous RNA polymerase of the treated cell may mediate transcription in vivo, or cloned RNA polymerase can be used for transcription in vitro. Aptamer-regulated nucleic acids, including antiswitches or those that modulate target gene activity by RNAi mechanisms may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. Aptamer-regulated nucleic acids may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "siRNAs." These nucleic acids are between about 19-35 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex or translation is inhibited. In a particular embodiment, the 21-23 nucleotides siRNA molecules comprise a 3' hydroxyl group.

In other embodiments, the subject RNAi constructs are "miRNAs." microRNAs (miRNAs) are small non-coding RNAs that direct post transcriptional regulation of gene expression through interaction with homologous mRNAs. miRNAs control the expression of genes by binding to complementary sites in target mRNAs from protein coding genes. miRNAs are similar to siRNAs. miRNAs are processed by nucleolytic cleavage from larger double-stranded precursor molecules. These precursor molecules are often hairpin structures of about 70 nucleotides in length, with 25 or more nucleotides that are base-paired in the hairpin. The RNAse III-like enzymes Drosha and Dicer (which may also be used in siRNA processing) cleave the miRNA precursor to produce an miRNA. The processed miRNA is single-stranded and incorporates into a protein complex, termed RISC or miRNP. This RNA-protein complex targets a complementary mRNA. miRNAs inhibit translation or direct cleavage of target mRNAs. (Brennecke et al., Genome Biology 4:228 (2003); Kim et al., Mol. Cells 19:1-15 (2005).

In certain embodiments, miRNA and siRNA constructs can be generated by processing of longer double-stranded RNAs, for example, in the presence of the enzymes Dicer or Drosha. Dicer and Drosha are RNAse III-like nucleases that specifically cleave dsRNA. Dicer has a distinctive structure which includes a helicase domain and dual RNAse III motifs. Dicer also contains a region of homology to the RDE1/QDE2/ARGONAUTE family, which have been genetically linked to RNAi in lower eukaryotes. Indeed, activation of, or overexpression of Dicer may be sufficient in many cases to permit RNA interference in otherwise non-receptive cells, such as cultured eukaryotic cells, or mammalian (non-oocytic) cells in culture or in whole organisms. Methods and compositions employing Dicer, as well as other RNAi enzymes, are described in U.S. Pat. App. Publication No. 20040086884.

In one embodiment, the Drosophila in vitro system is used. In this embodiment, an aptamer-regulated nucleic acid is combined with a soluble extract derived from Drosophila embryo, thereby producing a combination. The combination is maintained under conditions in which the dsRNA is processed to RNA molecules of about 21 to about 23 nucleotides.

The miRNA and siRNA molecules can be purified using a number of techniques known to those of skill in the art. For example, gel electrophoresis can be used to purify such molecules. Alternatively, non-denaturing methods, such as non-denaturing column chromatography, can be used to purify the siRNA and miRNA molecules. In addition, chromatography (e.g., size exclusion chromatography), glycerol gradient centrifugation, affinity purification with antibody can be used to purify siRNAs and miRNAs.

In certain preferred embodiments, at least one strand of the siRNA sequence of an effector domain has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA sequence, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In certain embodiments, an aptamer-regulated nucleic acid is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that miRNAs and siRNAs can be produced by processing a hairpin RNA in the cell.

In yet other embodiments, a plasmid is used to deliver the double-stranded RNA, e.g., as a transcriptional product. After the coding sequence is transcribed, the complementary RNA transcripts base-pair to form the double-stranded RNA.

Other Applications

A further aspect of invention relates to applications of a ligand controlled nucleic acid molecule in different fields. For example, an aptamer-regulated nucleic acid can be employed to detect the presence or absence or the amount of a target molecule in a sample. The target molecule may be a metabolite, an ion, a peptide, a nucleic acid, etc. An aptamer-regulated nucleic acid can similarly be employed for imaging purposes. Further, an aptamer-regulated nucleic acid can be employed to target the effector nucleic acid domain to certain environments, e.g., a particular intracellular location or cell membrane.

Metabolic Engineering and Programming

An aptamer-regulated nucleic acid of the invention can function as a tool to sense and detect metabolite levels in a cell, which can be noninvasive. The imaging or detection can be used for quantification of one or more metabolites of interest. Alternatively, it can be used to regulate certain enzymes in a signaling pathway for control over flux through a pathway and product formation or to alter that metabolic state by targeting levels of proteins or enzymes in a cell.

In one embodiment, the invention provides a method of modulating the concentration and/or activity of a ligand in a cell. The method may comprise designing and selecting an aptamer responsive to the ligand and providing an aptamer-regulated nucleic acid comprising the selected aptamer and an effector RNA, wherein the effector RNA is targeted to a molecule, a signaling pathway, or a metabolic pathway in a cell that involves the ligand (e.g., a metabolite or an intermediate molecule). The methods of the invention may be used, for example, to respond to the accumulation of a toxic intermediate, to attenuate the activity of a signaling or metabolic pathway, or to alter the growth, survival, or differentiation of treated cells.

In another embodiment, a method is provided for modulating the concentration and/or activity of a target gene that is in a different signaling and/or metabolic pathway than that of the ligand. According to this method, aptamer-regulated nucleic acids may be used to establish conditional genetic networks. The method may comprise designing and selecting an aptamer responsive to a ligand and providing an aptamer-regulated nucleic acid comprising the selected aptamer and an effector RNA that is targeted to a molecule, a signaling pathway, or a metabolic pathway in a cell that is independent of the ligand-associated signaling pathway. Accordingly, aptamer-regulated nucleic acids may be used to engineer intracellular gene networks by sensing endogenously generated signals (e.g., ligands) and responding to these signals by affecting the expression of a gene in signaling pathways independent of the ligand. Aptamer-regulated nucleic acids may be used to allow cells to appropriately respond to the buildup of toxic intermediates and compounds, or to alter the physiology of a cell (e.g., growth, survival, or differentiation).

In a related embodiment, the methods and compositions of the invention may be adapted to monitor the concentration of metabolites. The method may comprise a sensor aptamer-regulated nucleic acid wherein the aptamer domain of the switch is responsive to the metabolite. By measuring changes in metabolite concentrations, aptamer-regulated nucleic acids may be used to determine the full range of biochemical effects induced, for example, by a therapeutic intervention. Aptamer-regulated nucleic acids can further be used to diagnose or predict disease by monitoring metabolite concentrations.

In other embodiments, aptamer-regulated nucleic acids can serve as tools for interfacing with the environment including both intracellular environment and extracellular environment. For example, an aptamer-regulated nucleic acid can be used to "transport" a target RNA to cell membrane or other cellular locations, potentially by the aptamer domain that recognizes a signal peptide, and alternatively, a particular target.

Aptamer-regulated nucleic acids can also be employed in a multiplex fashion. For example, multiple constructs may be introduced into a cell to read multiple inputs, which can provide different outputs depending on the combination of inputs. In particular, two or more different aptamer-regulated nucleic acids can be combined as concentration sensors to form, e.g., band-pass filters.

Exemplary Formulations

The aptamer-regulated nucleic acids of the invention may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject aptamer-regulated nucleic acids can be provided in formulations also including penetration enhancers, carrier compounds and/or transfection agents.

Representative United States patents that teach the preparation of such uptake, distribution and/or absorption assisting formulations which can be adapted for delivery of aptaSwitch molecules include, but are not limited to, U.S. Pat. Nos. 5,108,921; 5,354,844; 5,416,016; 5,459,127; 5,521,291; 51,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

Aptamer-regulated nucleic acids of the invention also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to aptamer-regulated nucleic acids and pharmaceutically acceptable salts, and other bioequivalents.

Pharmaceutically acceptable base addition salts are formed with metals or amines, such as alkali and alkaline earth metals or organic amines. Examples of metals used as cations are sodium potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids. Preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

Other formulations, delivery methods, and routes of administration are also provided, such as those described in U.S. Pat. App. Publication No. 20040063654.

Exemplary Uses

One aspect of the invention provides a method of modulating the amount and/or activity of a ligand in a cell. The method may comprise designing and selecting an aptamer responsive to the ligand and providing an aptamer-regulated nucleic acid comprising the selected aptamer and an effector RNA, and the effector RNA is targeted to a molecule, a signaling and/or metabolic pathway in the cell that involves the ligand, for example, as a metabolite or an intermediate molecule (or the ligand-associated signaling and/or metabolic pathway). The method may further comprise contacting a cell with the aptamer-regulated nucleic acid in an amount and/or for a time period sufficient for modulating the concentration and/or activity of the ligand in the cell when switched on.

Also provided is a method of modulating a biological or biochemical response of a cell to the presence, amount and/or activity of a ligand in a cell. The method may comprise designing and selecting an aptamer responsive to the ligand and providing an aptamer-regulated nucleic acid comprising the selected aptamer and an effector RNA, and the effector RNA is targeted to a gene that modulates a biological or biochemical response of the cell to the presence, amount and/or activity of the ligand in the cell. The method may further comprise contacting a cell with the aptamer-regulated nucleic acid in an amount and/or for a time period sufficient for modulating the biological or biochemical response of the cell when switched on.

Certain embodiments are also directed to a method of establishing a conditional genetic network, as described herein. The method may comprise providing an aptamer-regulated nucleic acid that comprises an aptamer domain and an effector domain; the aptamer domain is responsive to a ligand, while the effector domain is targeted to a molecule that is independent of the ligand-associated signaling pathway. The method further comprises contacting the cell with the aptamer-regulated nucleic acid in an effective amount and/or for a sufficient time period, is when switched on, that modulates expression of the target molecule, thereby establishing a conditional genetic network.

In a further aspect, a method of the invention is used to inhibit, or at least reduce, unwanted growth of cells in vivo, and particularly the growth of transformed cells. In certain embodiments, the subject method utilizes one or more aptamer-regulated nucleic acids of the invention to selectively inhibit the expression of genes encoding proliferation-regulating proteins. For instance, the subject method can be used to inhibit expression of a gene product that is essential to mitosis in the target cell, and/or which is essential to preventing apoptosis of the target cell. The aptamer-regulated nucleic acids of the present invention, in particular, the effector domains, can be designed to correspond to the coding sequence or other portions of mRNAs encoding the targeted proliferation-regulating protein. When treated with the aptamer-regulated nucleic acid, the loss-of-expression phenotype which results in the target cell causes the cell to become quiescent or to undergo apoptosis.

In certain embodiments, the subject aptamer-regulated nucleic acids are selected to inhibit expression of gene products which stimulate cell growth and mitosis. One class of genes which can be targeted by the method of the present invention are those known as oncogenes. As used herein, the term "oncogene" refers to a gene which stimulates cell growth and, when its level of expression in the cell is reduced, the rate of cell growth is reduced or the cell becomes quiescent. In the context of the present invention, oncogenes include intracellular proteins, as well as extracellular growth factors which may stimulate cell proliferation through autocrine or paracrine function. Examples of human oncogenes against which aptaSwitch molecules can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

In certain preferred embodiments, the subject aptamer-regulated nucleic acids are selected by their ability to inhibit expression of a gene(s) essential for proliferation of a transformed cell, and particularly of a tumor cell. Such the aptamer-regulated nucleic acids can be used as part of the treatment or prophylaxis for neoplastic, anaplastic and/or hyperplastic cell growth in vivo, including as part of a treatment of a tumor. The c-myc protein is deregulated in many forms of cancer, resulting in increased expression. Reduction of c-myc RNA levels in vitro results in induction of apoptosis. An antisense, siRNA, miRNA, or RNAi effector domain complementary to c-myc can therefore potentially be used as therapeutic for anti-cancer treatment. Preferably, the subject aptamer-regulated nucleic acids can be used in the therapeutic treatment of chronic lymphatic leukemia. Chronic lymphatic leukemia is often caused by a translocation of chromosomes 9 and 12 resulting in a Bcr/Abl fusion product. The resulting fusion protein acts as an oncogene; therefore, specific elimination of Bcr/Abl fusion mRNA may result in cell death in the leukemia cells. Indeed, transfection of siRNA molecules specific for the Bcr/Abl fusion mRNA into cultured leukemic cells, not only reduced the fusion mRNA and corresponding oncoprotein, but also induced apoptosis of these cells (see, for example, Wilda et al., Oncogene, 2002, 21:5716-5724).

In other embodiments, the subject aptamer-regulated nucleic acids are selected by their ability to inhibit expression of a gene(s) essential for activation of lymphocytes, e.g., proliferation of B-cells or T-cells, and particularly of antigen-mediated activation of lymphocytes. Such aptamer-regulated nucleic acids can be used as immunosuppressant agents, e.g., as part of the treatment or prophylaxis for immune-mediated inflammatory disorders.

In certain embodiments, the methods described herein can be employed for the treatment of autoimmune disorders. For example, the subject aptamer-regulated nucleic acids are selected for their ability to inhibit expression of a gene(s) which encode or regulate the expression of cytokines. Accordingly, constructs that cause inhibited or decreased expression of cytokines such as TNF-alpha, IL-1 alpha, IL-6 or IL-12, or a combination thereof, can be used as part of a treatment or prophylaxis for rheumatoid arthritis. Similarly, constructs that cause inhibited or decreased expression of cytokines involved in inflammation can be used in the treatment or prophylaxis of inflammation and inflammation-related diseases, such as multiple sclerosis.

In other embodiments, the subject aptamer-regulated nucleic acids are selected for their ability to inhibit expression of a gene(s) implicated in the onset or progression of diabetes. For example, experimental diabetes mellitus was found to be related to an increase in expression of p21WAF1/CIP1 (p21), and TGF-beta 1 has been implicated in glomerular hypertrophy (see, for example, Al-Douahji, et al. Kidney Int. 56:1691-1699). Accordingly, constructs that cause inhibited or decreased expression of these proteins can be used in the treatment or prophylaxis of diabetes.

In other embodiments, the subject aptamer-regulated nucleic acids are selected for their ability to inhibit expression of ICAM-1 (intracellular adhesion molecule). An antisense nucleic acid that inhibits expression of ICAM-1 is being developed by Isis pharmaceutics for psoriasis. Additionally, an antisense nucleic acid against the ICAM-1 gene is suggested for preventing acute renal failure and reperfusion injury and for prolonging renal isograft survival (see, for example, Halier et al. (1996) Kidney Int. 50:473-80; Dragun et al. (1998) Kidney Int. 54:590-602; Dragun et al. (1998) Kidney Int. 54:2113-22). Accordingly, the present invention contemplates the use of aptamer-regulated nucleic acids comprising similar antisense effector RNA domains, siRNA, miRNA, or RNAi effector domains targeting ICAM-1 gene in the above-described diseases.

In other embodiments, the subject aptamer-regulated nucleic acids are selected by their ability to inhibit expression of a gene(s) essential for proliferation of smooth muscle cells or other cells of endothelium of blood vessels, such as proliferating cells involved in neointima formation. In such embodiments, the subject method can be used as part of a treatment or prophylaxis for restenosis.

Merely to illustrate, aptamer-regulated nucleic acids applied to the blood vessel endothelial cells after angioplasty can reduce proliferation of these cells after the procedure. Merely to illustrate, a specific example is an siRNA complementary to c-myc (an oncogene). Down-regulation of c-myc inhibits cell growth. Therefore, an effector domain comprising an siRNA sequence can be prepared by including the following sequence in an effector domain:

```
5'-UCCCGCGACGAUGCCCCUCATT-3'    (SEQ ID NO: 21)

3'-TTAGGGCGCUGCUACGGGGAGU-5'    (SEQ ID NO: 22)
```

All bases are ribonucleic acids except the thymidines shown in bold, which are deoxyribose nucleic acids (for more stability). Double-stranded RNA can be prepared by mixing the oligonucleotides at equimolar concentrations in 10 mM Tris-Cl (pH 7.0) and 20 mM NaCl, heating to 95° C., and then slowly cooling to 37° C. Alternatively, the sequence can be included in a hairpin structure. The resulting nucleic acid can then be purified by agarose gel electrophoresis and delivered to cells either free or complexed to a delivery system such as a cyclodextrin-based polymer. For in vitro experiments, the effect of the aptamer-regulated nucleic acid can be monitored by growth curve analysis, RT-PCR or western blot analysis for the c-myc protein.

It is demonstrated that antisense oligodeoxynucleotides directed against the c-myc gene inhibit restenosis when given by local delivery immediately after coronary stent implantation (see, for example, Kutryk et al. (2002) J Am Coll Cardiol. 39:281-287; Kipshidze et al. (2002) J Am Coll Cardiol. 39:1686-1691). Therefore, the present invention contemplates delivering an aptamer-regulated nucleic acid against the c-Myc gene (i.e., c-Myc antisense or RNAi construct) to the stent implantation site with an infiltrator delivery system (Interventional Technologies, San Diego, Calif.). Preferably, the c-Myc-targeting aptamer-regulated nucleic acid is directly coated on stents for inhibiting restenosis. Similarly, the c-Myc-targeting aptamer-regulated nucleic acid can be delivered locally for inhibiting myointimal hyperplasia after percutaneous transluminal coronary angioplasty (PTCA) and exemplary methods of such local delivery can be found, for example, Kipshidze et al. (2001) Catheter Cardiovasc Interv. 54:247-56. In certain embodiments, the aptamer-regulated nucleic acids are chemically modified with, for example, phosphorothioates or phosphoramidate.

Early growth response factor-1 (i.e., Egr-1) is a transcription factor that is activated during mechanical injury and regulates transcription of many genes involved with cell proliferation and migration. Therefore, down-regulation of this protein may also be an approach for prevention of restenosis. An effector domain of an aptamer-regulated nucleic acid directed against the Egr-1 gene can be prepared by including the following sequence in the effector domain:

```
5'-UCGUCCAGGAUGGCCGCGGTT-3'     (SEQ ID NO: 23)

3'-TTAGCAGGUCCUACCGGCGCC-5'     (SEQ ID NO: 24)
```

Again, all bases are ribonucleic acids except the thymidines shown in bold, which are deoxyribose nucleic acids. The effector domains and thereby the aptamer-regulated nucleic acids can be prepared from these sequences and introduced into cells as described herein.

EXAMPLES

The invention now being generally described, it will be more readily understood by reference to the following examples, which are included merely for purposes of illustration of certain aspects and embodiments of the present invention, and are not intended to limit the invention.

Plasmid Construction, Cell Strains, Reagents

Figure 10:
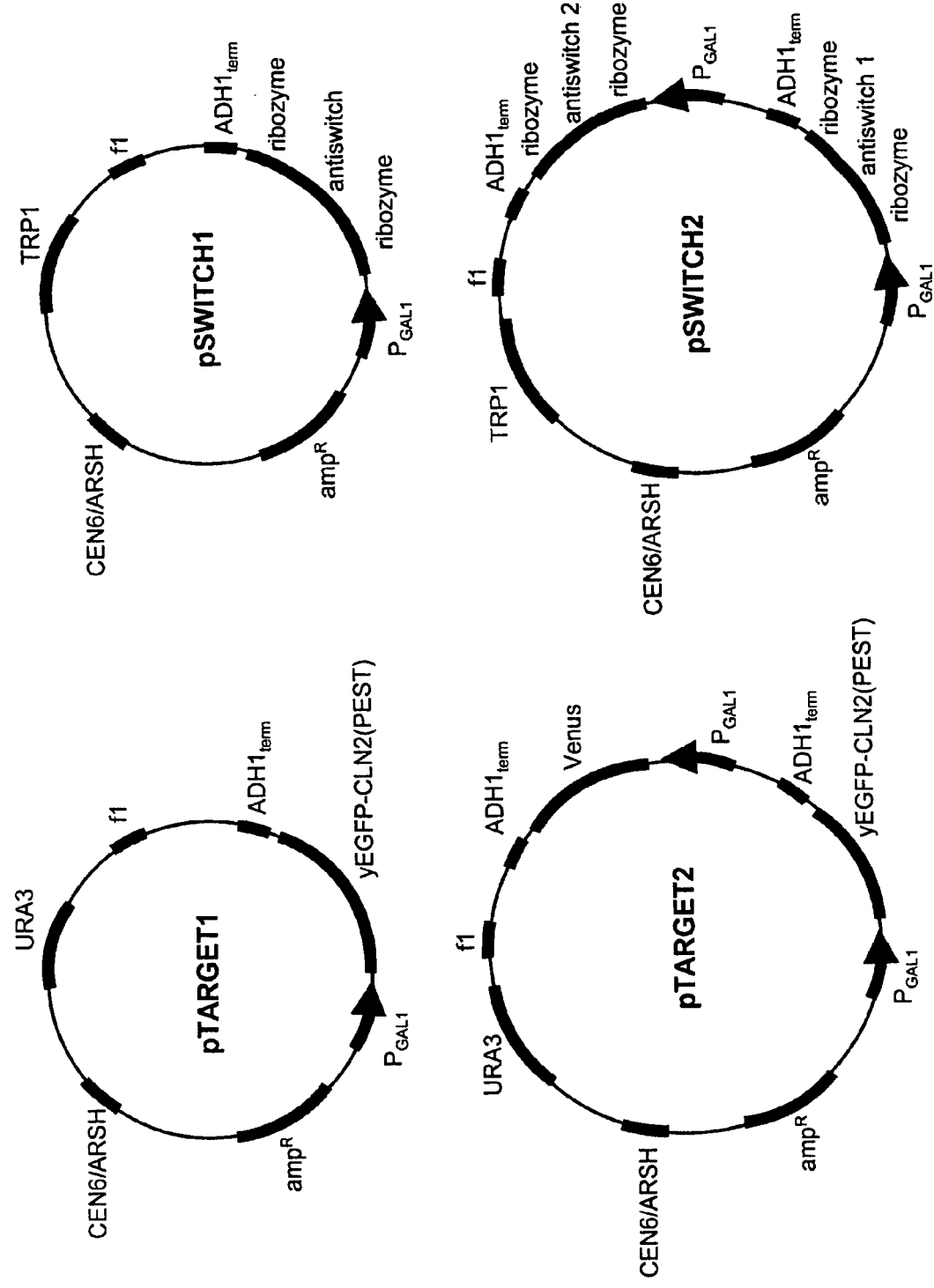
FIG. 10 shows a set of plasmids used in the in vivo antiswitch characterization studies. pTARGET1 and pSWITCH1 were used in single antiswitch-single target studies and pTARGET2 and pSWITCH2 were used in multiple antiswitch-multiple target studies. All constructs are under the control of an inducible galactose promoter, contain a yeast nutrient-based selection marker, a yeast centromeric origin of replication, an E. coli f1 origin of replication, and an E. coli ampicillin resistance marker.
Figure 14:
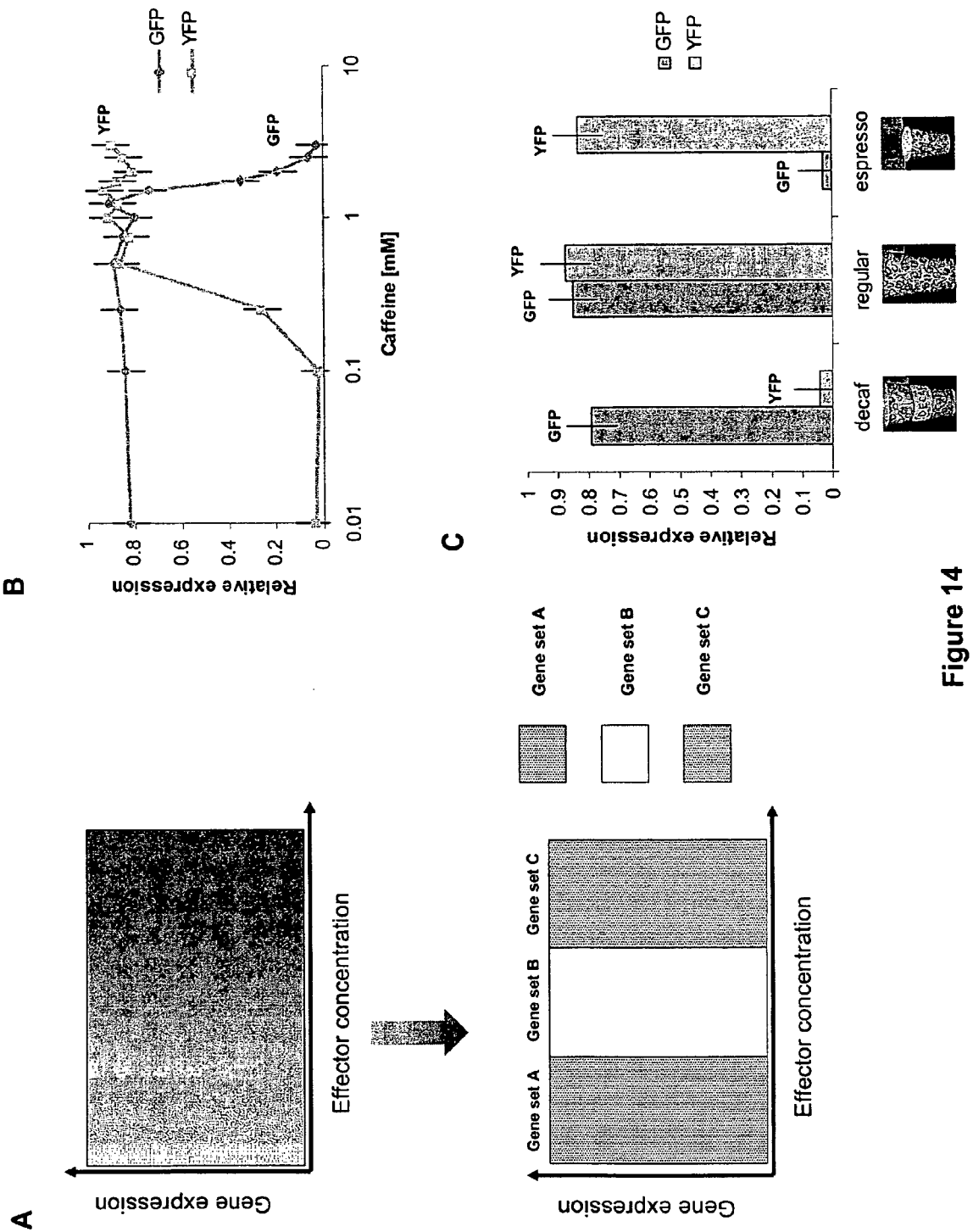
FIGS. 14a-c are graphs showing an antiswitch-based caffeine sensor/gradient filter.
Figure 15:
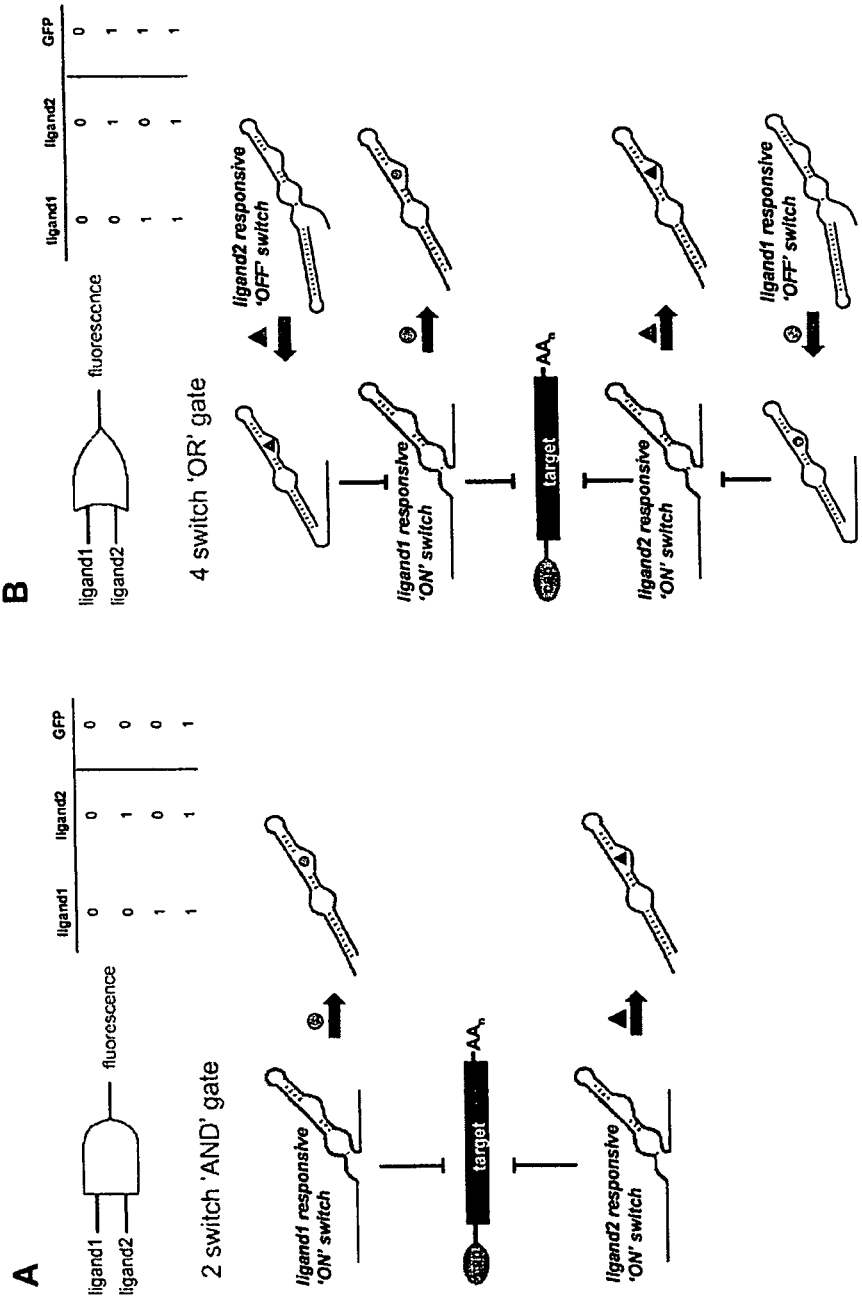
FIGS. 15a-b show aptamer-regulated nucleic acids that bind and respond to multiple ligands, allowing for logical signal integration of multiple molecular ligand inputs.
Figure 16:
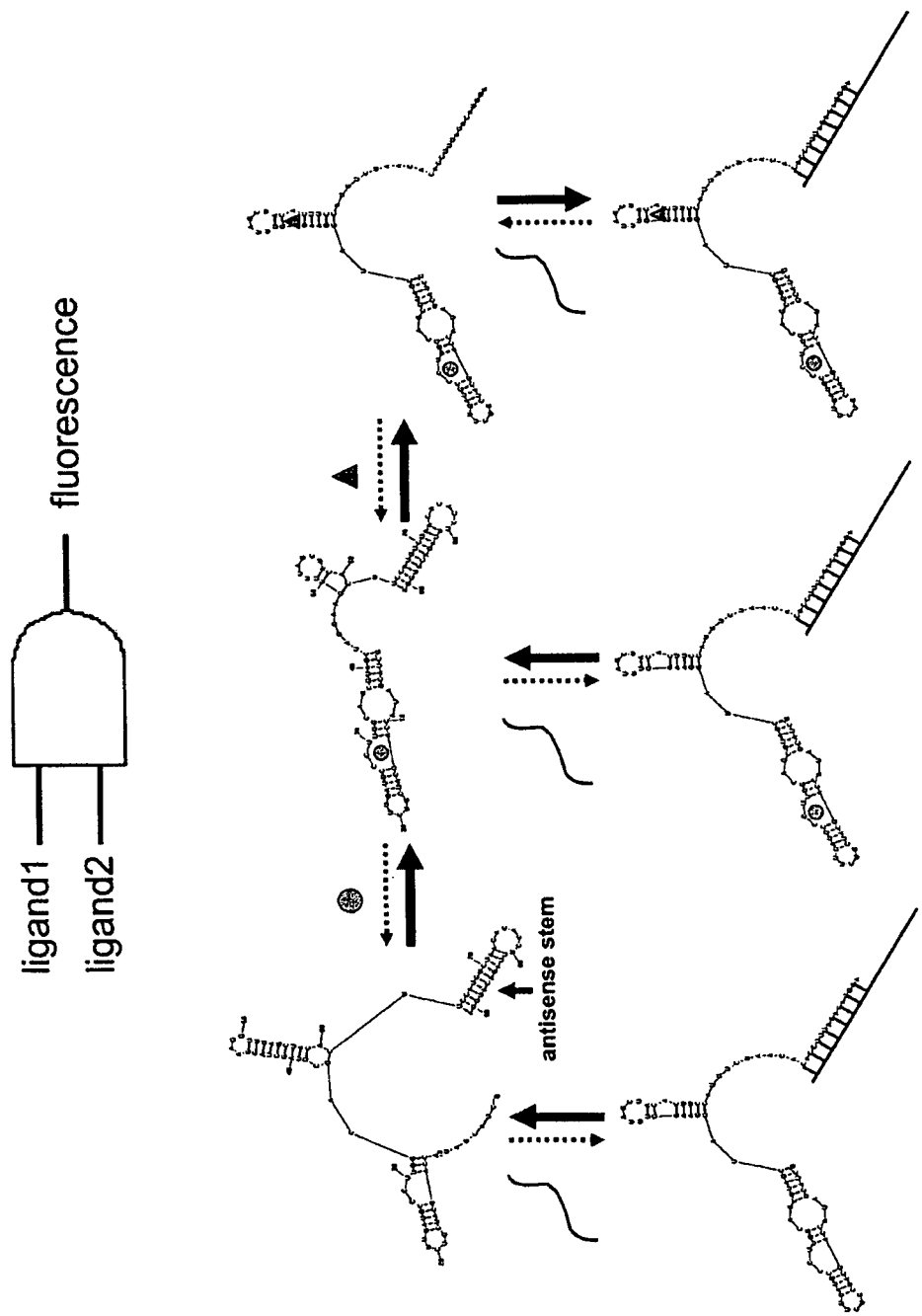
FIG. 16 shows a schematic diagram of cooperative aptamer-regulated nucleic acids (SEQ ID NO: 20) that bind and respond to multiple ligands.
Figure 17:
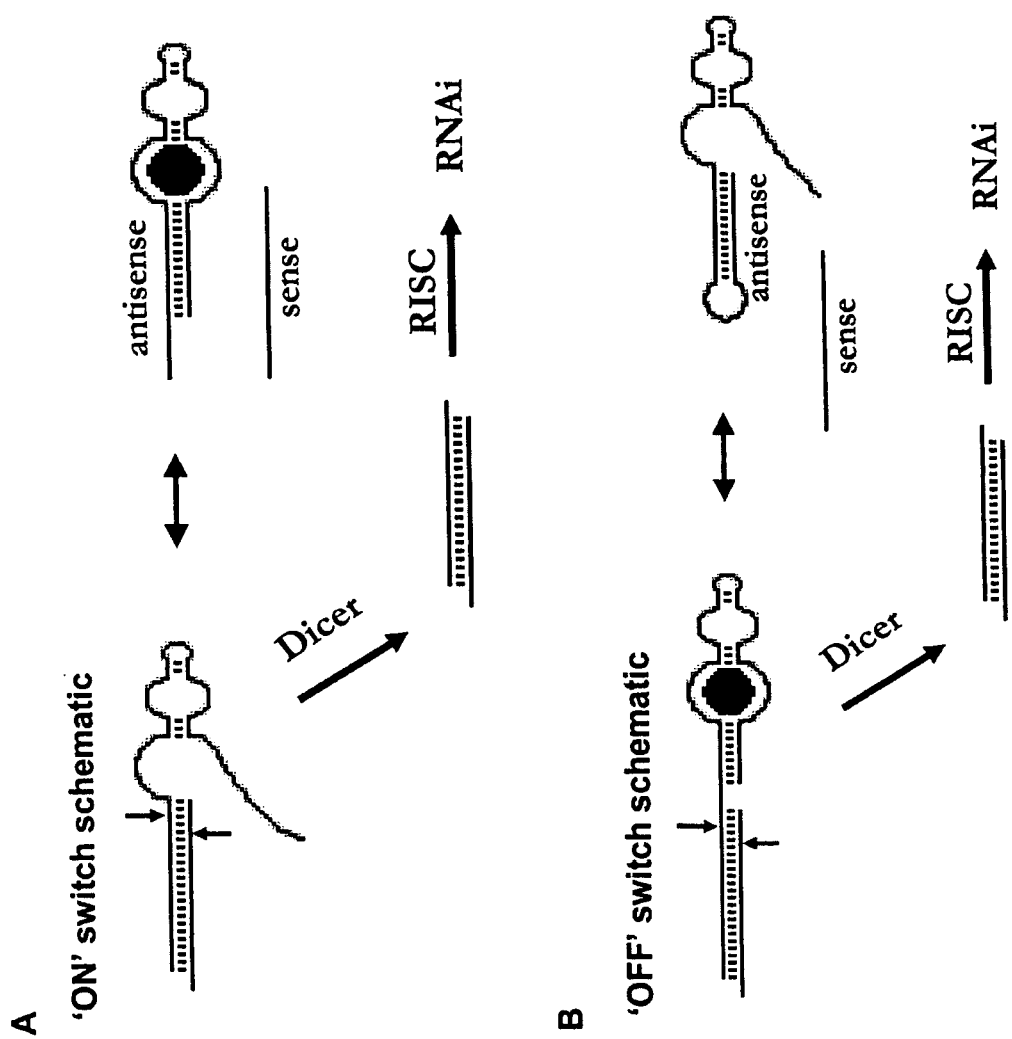
FIG. 17 shows Dicer substrate switches for ligand controlled regulation of targets using RNA interference.
Figure 18:
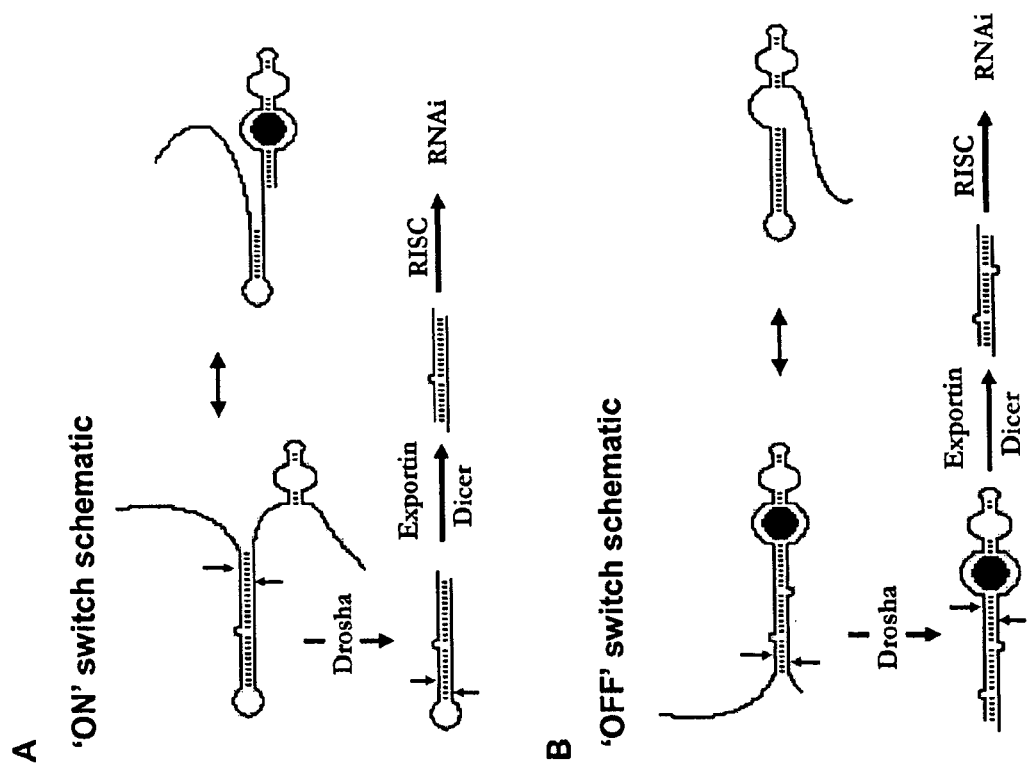
FIG. 18 shows Drosha substrate switches for ligand controlled regulation of targets using RNA interference.
Figure 19:
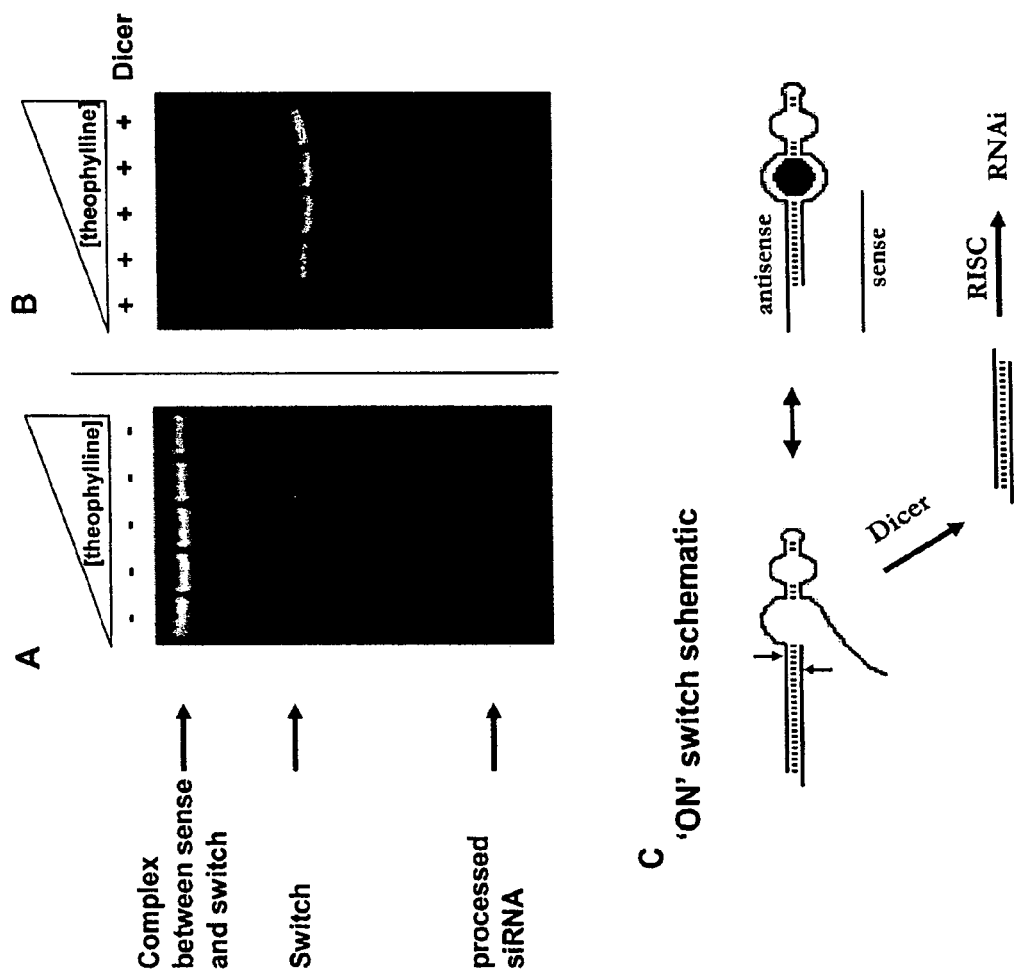
FIGS. 19a-c show Dicer-dependent switches in response to binding of the ligand theophylline.
Figure 20:
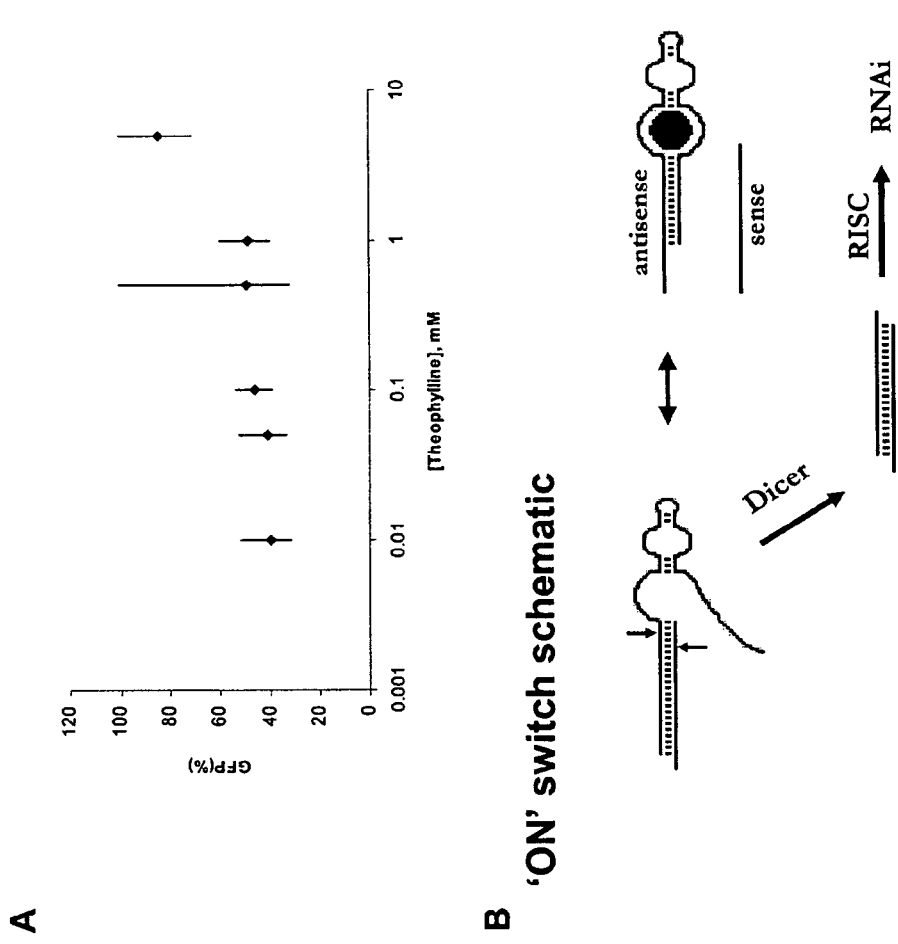
FIGS. 20a and 20b show a decrease in GFP expression in response to Dicer-dependent switches that respond to in vivo theophylline concentrations.
Figure 21:
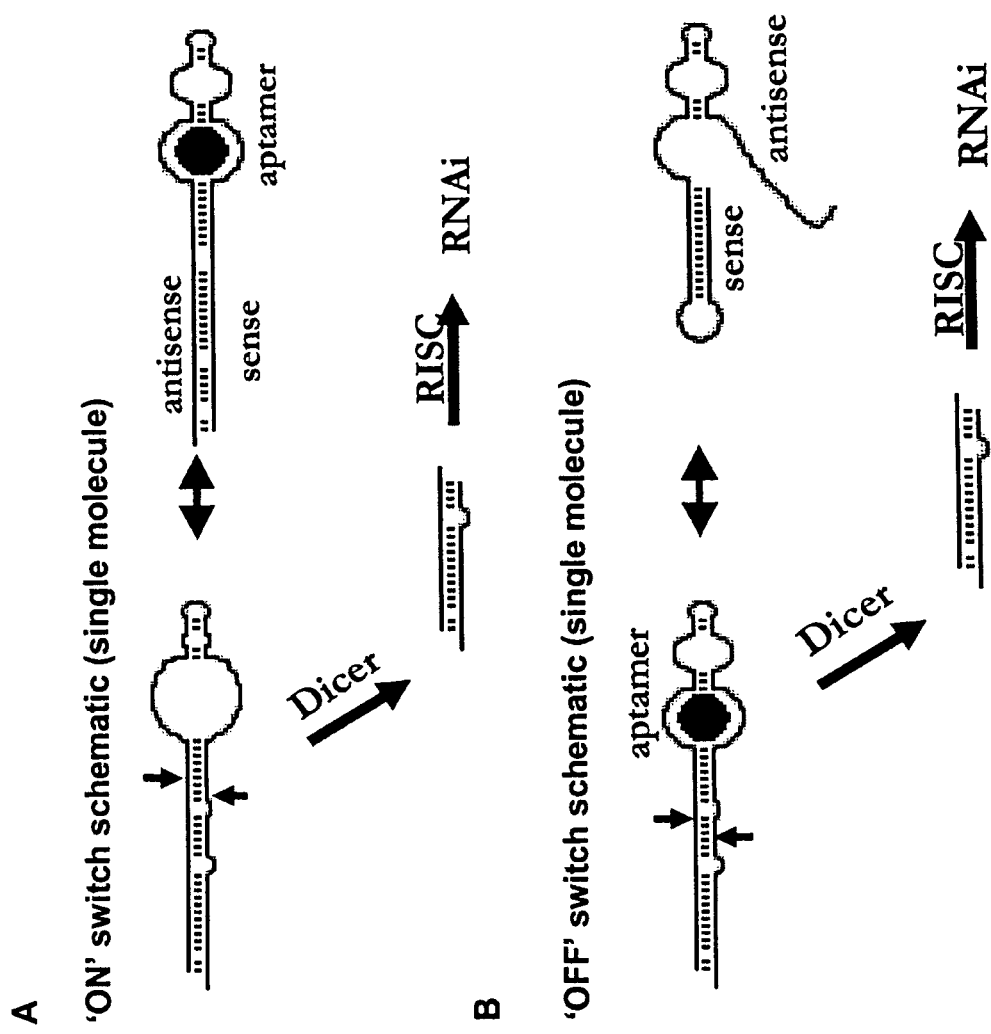
FIGS. 21a-b show single-molecule Dicer-dependent switches for ligand controlled regulation of targets using RNAi.

Standard molecular biology techniques were employed to construct all plasmids (Sambrook et al., Molecular cloning: A laboratory manual (Cold Spring Harbor Laboratory Press, Cold Spring Harbor, N.Y., 2001)). Four different plasmid constructs were generated by cloning into the pRS314-Gal and pRS316-Gal shuttle plasmids (Sikorski et al., *Genetics* 122, 19-27 (1989)). Genes and antiswitch constructs were cloned into multi-cloning sites, downstream of a GAL1 promoter. These plasmids (see FIGS. 10 and 12) contain an *E. coli* origin of replication (f1) and selection marker for ampicillin resistance, as well as an *S. cerevisiae* origin of replication (CEN6-ARSH4) and selection markers for tryptophan (TRP1-pRS314) and uracil (URA3-pRS316) biosynthetic genes in order to select cells harboring these plasmids in synthetic complete media supplemented with the appropriate amino acid dropout solution (Sambrook et al., Molecular cloning: A laboratory manual (Cold Spring Harbor Laboratory Press, Cold Spring Harbor, N.Y., 2001)). In the first plasmid system, pTARGET1, yEGFP was cloned into the multi-cloning site and is located between a GAL1 promoter and ADH1 terminator. In the second plasmid system, pSWITCH1, various antiswitches were cloned between two hammerhead ribozymes which are located between a GAL1 promoter and ADH1 terminator. In the third plasmid system, pTARGET2, a PGAL-Venus-ADH1 term construct was cloned downstream of the PGAL-yEGFP-ADH1 term construct in pTARGET1. Therefore, pTARGET2 produces two target transcripts when induced with galactose. In the fourth system, pSWITCH2, a PGAL-antiswitch-ADH1 term construct was cloned downstream of the PGAL-antiswitch-ADH1 term construct in pSWITCH1. Therefore, pSWITCH2 produces two antiswitch constructs when induced by the presence of galactose. Two sets of plasmids, pTARGET1 and pSWITCH1 or pTARGET2 and pSWITCH2, were transformed into *S. cerevisiae* simultaneously and maintained with the appropriate nutrient selection pressure. In these two plasmid sets, expression of antiswitch constructs and their targets was induced upon the addition of galactose to the media. Oligonucleotide primers were purchased from Integrated DNA Technologies. All genes and antiswitches were PCR amplified in a Dyad PCR machine (MJ Research) with Taq DNA polymerase (Roche). The yegfp gene was obtained from pSVA1535 and the venus gene was obtained from pCS2/Venus (Nagai et al., *Nat Biotechnol* 20, 87-90 (2002)). All antiswitch sequences were obtained using custom oligonucleotide design (see FIG. 12).

All plasmids were constructed using restriction endonucleases and T4 DNA ligase from New England Biolabs. Plasmids were screened by transforming into an electrocompetent *E. coli* strain, DH10B (Invitrogen; F-mcrA Δ(mrr-hsdRMS-mcrBC) φ80dlacZΔM15 ΔlacX74 deoR recA1 endA1 araD139 Δ(ara, leu) 7697 galU galK λ-rpsL nupG), using a Gene Pulser Xcell System (BioRAD) according to manufacturer's instructions. Subcloning was confirmed by restriction analysis. Confirmed plasmids were then transformed into the wild-type W303 *S. cerevisiae* strain (MATα his3-11,15 trp1-1 leu2-3 ura3-1 ade2-1) using standard lithium acetate procedures (Gietz et al., Guide to Yeast Genetics and Molecular and Cell Biology, Part B (eds. Guthrie, C. & Fink, G.) 87-96 (Academic Press, San Diego, 2002)). *E. coli* cells were grown on Luria-Bertani media (DIFCO) with 100 μg/ml ampicillin (EMD Chemicals) for plasmid selection, and *S. cerevisiae* cells were grown in synthetic complete media (DIFCO) supplemented with the appropriate dropout solution (Calbiochem). Plasmid isolation was done using Perfectprep Plasmid Isolation Kits (Eppendorf).

Protein Expression Assays

Yeast cells were inoculated into synthetic complete media supplemented with the appropriate drop out solution and sugar source (2% raffinose, 1% sucrose) and grown overnight at 30° C. Cells were back diluted into fresh media to an $OD_{600}$ of 0.1 and grown at 30° C. For assaying antiswitch activity, this fresh media contained appropriate concentrations of theophylline (Sigma), caffeine (Sigma), tetracycline (Sigma), or water (negative control) and expression was induced to a final concentration of 2% galactose, or an equivalent volume of water was added (noninduced control). After growing for three hours, the GFP and Venus levels were assayed on a Safire (Tecan) fluorescent plate reader set to the appropriate excitation (GFP-485 nm; Venus-515 nm) and emission (GFP-515 nm; Venus-508) wavelengths. For assaying the antiswitch temporal response, cells were back diluted into fresh media containing 2% galactose. After growing in inducing media for three hours, theophylline or water was added and fluorescence was monitored over time. Fluorescence was normalized for cell number by dividing relative fluorescence units (RFUs) by the $OD_{600}$ of the culture.

RNA Quantification

Yeast cells were grown according to methods detailed in protein expression assays. Total RNA was extracted using standard acid phenol extraction procedures (Caponigro et al., *Mol Cell Biol* 13, 5141-8 (1993)). Briefly, cells were pelleted and frozen in liquid nitrogen. Pellets were resuspended in a 50 mM NaOAc (pH 5.2) and 10 mM EDTA buffer. Cells were lysed by the addition of SDS to a final concentration of 1.6% and equal volume of acid phenol. Solutions were kept at 65° C. with intermittent vortexing for 10 minutes. Following cooling on ice, the aqueous phase was extracted and further extraction was carried out with an equal volume of chloroform. RNA samples were ethanol precipitated and resuspended in water. Total RNA was quantified by $OD_{260}$ readings. RNA samples were DNased (Invitrogen) according to manufacturer's instructions. cDNA was synthesized using gene-specific primers (see FIG. 13) and Superscript III reverse transciptase (Invitrogen) according to the manufacturer's instructions. qRT-PCR was performed on this cDNA using an iCycler iQ system (BioRAD). Samples were prepared using the iQ SYBR green supermix and primer pairs specific for different templates (see FIG. 13) on dilution series of the cDNA, according to the manufacturer's instructions. Data was analyzed using the iCycler iQ software.

In vitro Antiswitch Affinity Experiments

Antiswitch and target sequences were PCR amplified with primers containing a T7 polymerase promoter. RNA was transcribed using Ampliscribe T7 transcription kits (Epicentre) according to manufacture's instructions, except that transcription was carried out at 42° C. and for gel-shift assays antiswitches were radiolabeled by the addition of [$\alpha$-$^{32}$P]-UTP to the transcription mix. The RNA was purified on a 15% denaturing gel, eluted, ethanol precipitated, and resuspended in water. RNA was quantified by $OD_{260}$ readings. For nuclease mapping, antiswitches were 5' end labeled with fluorescein (Molecular Probes) by incubating 25 µg of RNA with phosphate reactive label, dissolved in DMSO (Sigma), in labeling buffer (0.12 M methylimidazole pH 9.0, 0.16 M EDAC) for four hours, according to manufacturer's instructions. Labeled RNA was purified by ethanol precipitation and run on a 12% denaturing gel. Fluorescent bands were excised from the gel, eluted into water for three hours at 37° C., and ethanol precipitated.

For gel shift assays, equimolar amounts (5 nM) of radiolabeled antiswitches and target RNA were incubated in varying concentrations of theophylline at room temperature for 30 minutes in 15 µL buffer (50 mM Tris-HCl pH 8.0, 100 mM NaCl, 5 mM MgCl2). Following the incubation, 10% glycerol was added to the RNA-target-ligand mixtures and RNA complexes were separated from free RNA by electrophoresis at 125 V on an 8% polyacrylamide gel in 1×Tris-borate buffer at room temperature for several hours. Gels were dried and antiswitch mobility was imaged on a FX phosphorimager (BioRAD).

For nuclease mapping, fluorescein-labeled antiswitch RNA was resuspended in buffer (50 mM Tris-HCl pH 8.0, 100 mM NaCl, 5 mM MgCl2), denatured at 65° C. for three minutes, and allowed to slow cool to room temperature. Antiswitch RNA was incubated with varying concentrations of theophylline at room temperature for 15 minutes. RNase T1 (Ambion) was added to the antiswitch-ligand mixture and incubated at room temperature for 15 minutes. Cleavage products were visualized using laser-induced fluorescence capillary electrophoresis on a P/ACE MDQ machine (Beckman) using a single-stranded nucleic acid analysis kit (Beckman) according to manufacturer's instructions.

RNA Free Energy Calculations

RNA free energy was calculated with RNAstructure version 3.71 (Mathews et al., *Proc Natl Acad Sci USA* 101, 7287-92 (2004)).

Antiswitch Design

Antisense technologies have been widely utilized to regulate gene expression (Weiss et al., *Cell Mol Life Sci* 55, 334-58 (1999); and Scherer et al., *Nat Biotechnol* 21, 1457-65 (2003)). Allosteric regulatory functionality has been engineered by designing a platform on which ligand binding structures were appended to the antisense molecule. In this platform, the antisense domain is sequestered in an "antisense stem" or "antisense effector domain" in the absence of ligand. Ligand binding to the aptamer domain mediates a change in the conformational dynamics of the antisense stem that results in the antisense domain being in a more single-stranded form (FIG. 1a). Such mechanisms have been described in the construction of signaling aptamers and other allosterically controlled RNAs (Nutiu et al., *J Am Chem Soc* 125, 4771-8 (2003)).

Figure 1B:
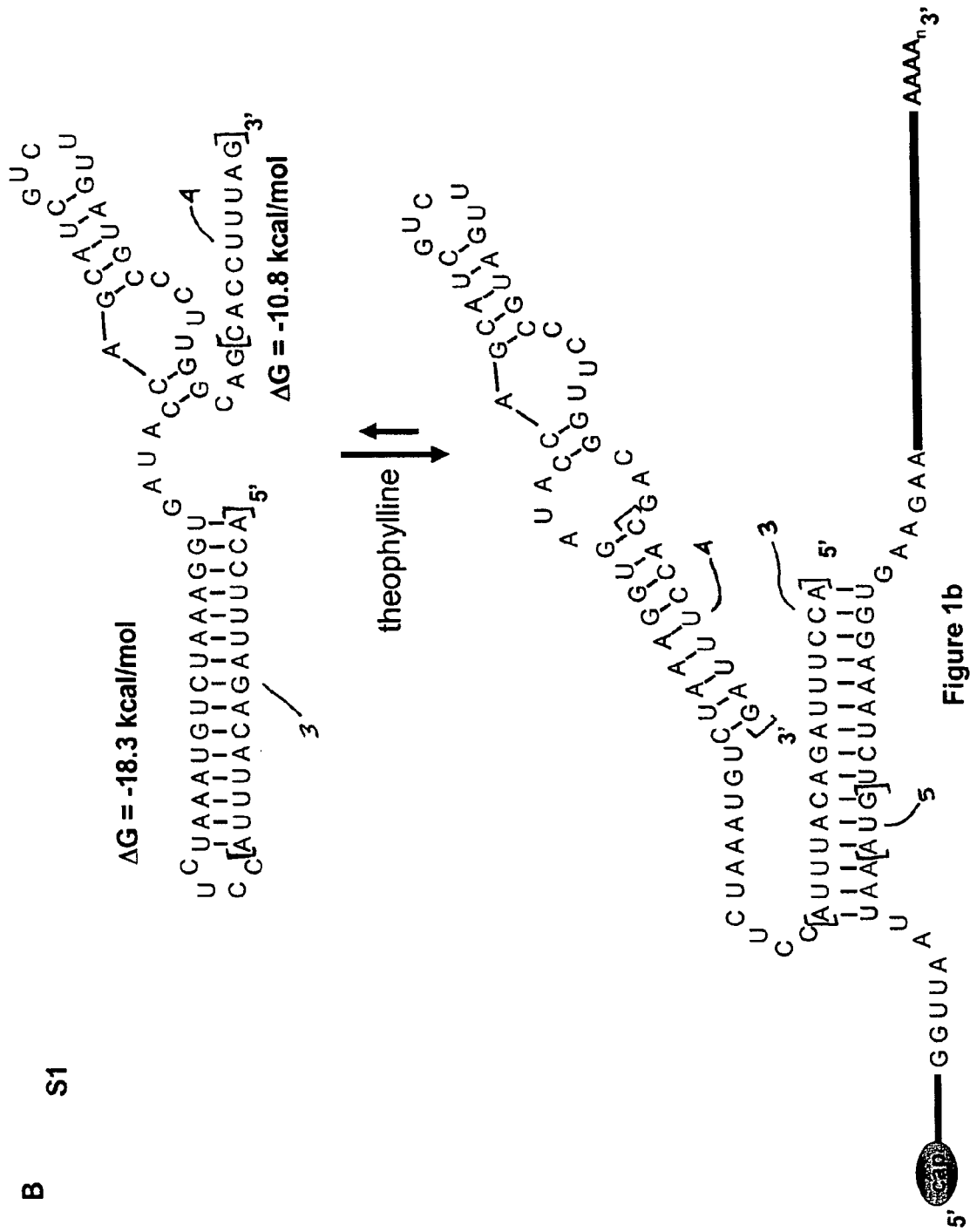

An initial antiswitch, s1, was constructed using a previously selected aptamer that binds the xanthine derivative theophylline with high affinity (Kd=0.29 µM) and specificity (Zimmermann et al., *RNA* 6, 659-67 (2000)). The antisense effector RNA domain is designed to base pair with a 15 nucleotide region around the start codon of a target mRNA encoding green fluorescent protein (GFP). The stem of the theophylline aptamer is redesigned so that the antisense portion base pairs in a stable stem, the antisense stem, in the absence of ligand, but so that another, overlapping stem forms upon ligand binding, the "aptamer stem," or the "aptamer domain," forcing the antisense portion into a more single-stranded state (FIGS. 1a and 1b). The aptamer stem and antisense stem are designed such that the antisense stem is slightly more stable than the aptamer stem. Previous work has demonstrated that the sequence of the lower theophylline aptamer stem is not critical for ligand binding (Zimmermann et al., *Nat Struct Biol* 4, 644-9 (1997)) and this sequence was altered to interact with the antisense stem upon ligand binding. It is anticipated that these molecules will function through alterations in conformational dynamics, such that in the absence of ligand and presence of target transcript, the stem sequestering the antisense is more likely to form; whereas in the presence of both ligand and target transcript, the free energy associated with binding of theophylline (approximately 8.9 kcal/mol) (Gouda et al., *Biopolymers* 68, 16-34 (2003)), and RNA stabilization in the aptamer structure enables the aptamer stem to form, freeing the antisense domain to bind its target transcript. RNAstructure (Mathews et al., *Proc Natl Acad Sci USA* 101, 7287-92 (2004)) was used to predict the stability of the RNA secondary structures formed. Due to the dual-stem design of the antiswitch, it is anticipated that the free energies of the aptamer binding to its ligand and the antisense binding to its target mRNA will contribute in a cooperative manner to the structural switching of the antiswitch molecule.

In vivo Genetic Regulation

Figure 6:
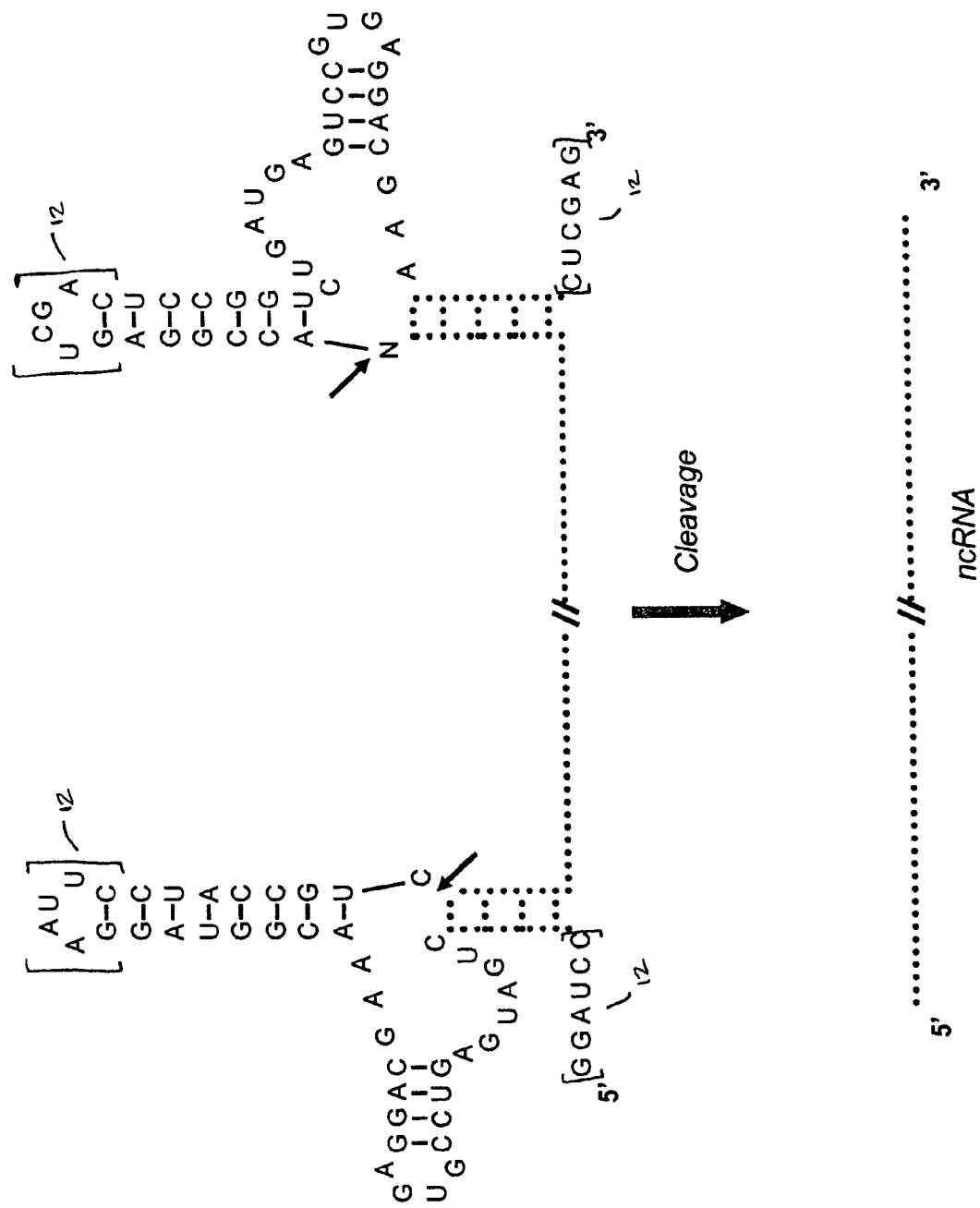
FIG. 6 shows the sequence (SEQ ID NO: 18) and cleavage mechanism of ncRNA expression construct. The expression construct enables cloning of general sequences in between two hammerhead ribozyme sequences through unique restriction sites BamHI, EcoRI, SalI, and XhoI (12). Predicted cleavage sites are indicated by arrows, general ncRNA insert is indicated by a dotted line. Following cleavage the resulting ncRNA has defined 3' and 5' ends.

The expression of antiswitches in *S. cerevisiae* was accomplished using a novel non-coding RNA (ncRNA) expression construct similar to a previously described system (Taira et al., *Nucleic Acids Res* 19, 5125-30 (1991)) (see FIG. 6). Briefly, the RNA to be expressed is cloned between two hammerhead ribozymes known to self-cleave in vivo (Samarsky et al., *Proc Natl Acad Sci USA* 96, 6609-14 (1999)). This dual hammerhead construct can be placed under the control of Pol II promoters, and when transcribed the flanking hammerhead ribozymes cleave out from the desired RNA at an efficiency greater than 99% (see FIG. 11). The construct enables creation of ncRNAs with defined 5' and 3' ends that are free of potentially interfering flanking sequences. Antiswitch s1 was expressed in this construct under control of a galactose-inducible (GAL1) promoter in yeast cells. A plasmid containing a yeast enhanced GFP (yEGFP) (Mateus et al., *Yeast* 16, 1313-23 (2000)) under the control of a GAL1 promoter was transformed into the same cells (FIG. 1a).

Figure 1C:
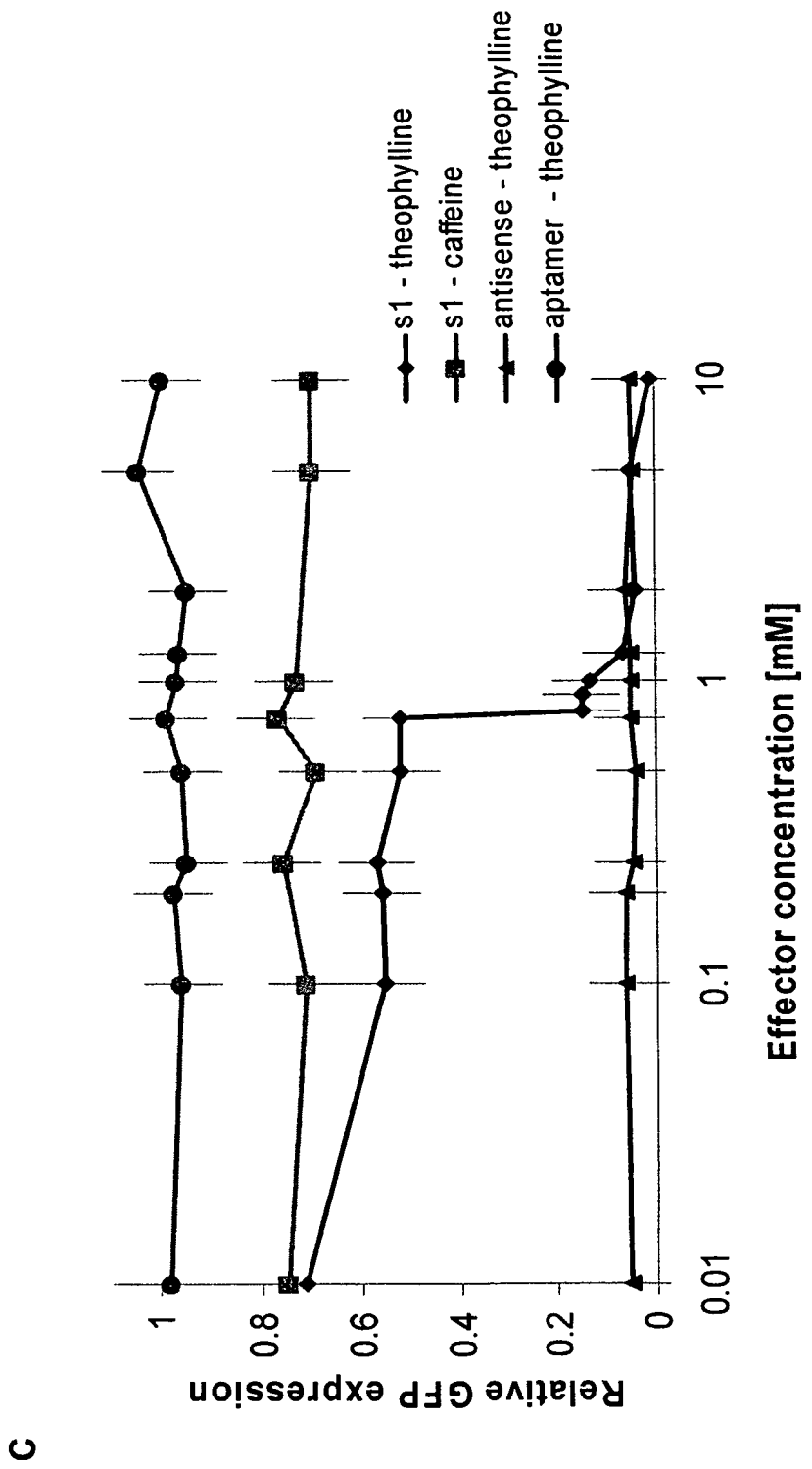

Results from protein expression assays demonstrate ligand specific in vivo activity of s1 (FIG. 1c). Expression of antiswitch s1 in the absence of theophylline decreases GFP expression from control levels by approximately 30%, where addition of greater than 0.8 mM theophylline decreases expression to background levels. The antisense and aptamer domains were expressed separately as controls and had expected effects on GFP expression levels. It is interesting to note the rapid change in expression levels between 0.75 mM and 0.8 mM theophylline. The antiswitch s1 displays binary, on/off behavior rather than linearly modulating expression over a range of theophylline concentrations. This response supports the anticipated cooperative mechanism of structural switching dependent on both ligand and target mRNA. It has been previously demonstrated that the aptamer used in this antiswitch does not bind caffeine (Zimmermann et al., *RNA* 6, 659-67 (2000)), which differs from theophylline by a single methyl group. The addition of caffeine does not change expression levels from those of an inactive switch, demonstrating that specific ligand-aptamer interactions are necessary to activate the antiswitch and free the antisense domain to decrease gene expression of GFP.

Mechanism of Antiswitch Regulation

Figure 1D:
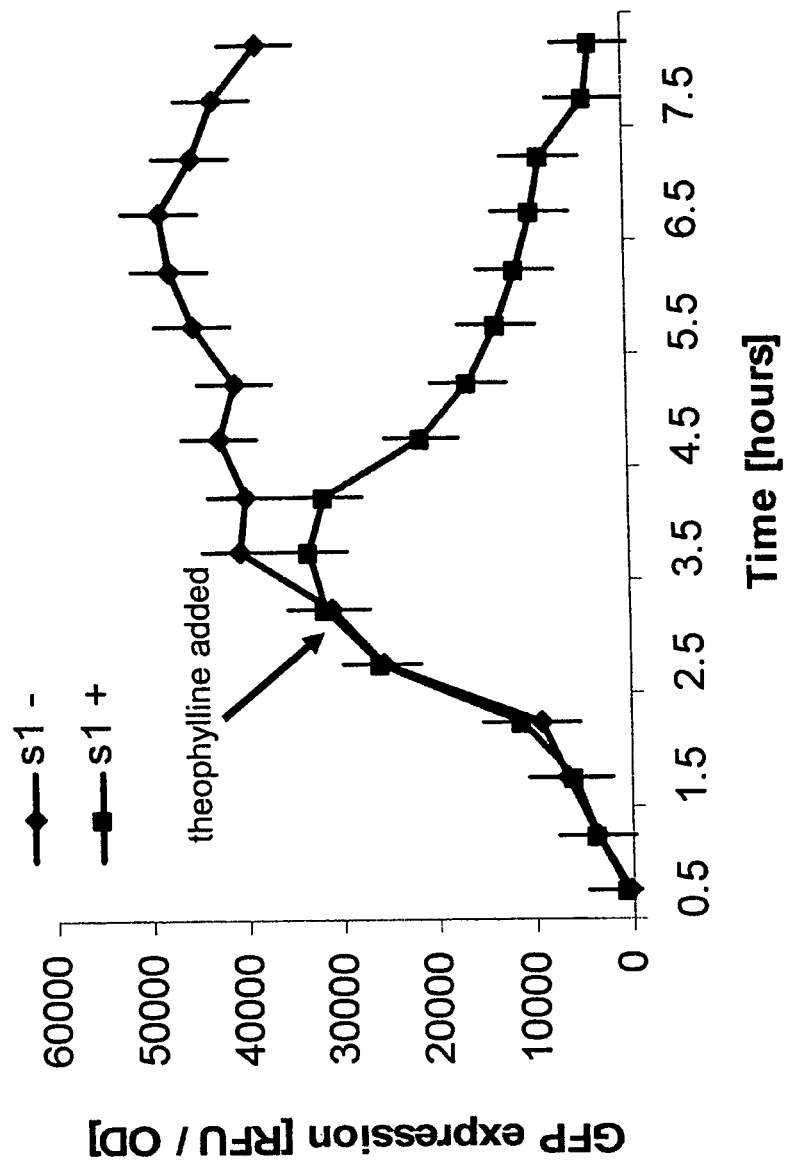

Quantitative real-time PCR (qRT-PCR) was performed on antiswitch s1 and target mRNA extracted from cells grown under different conditions to determine relative RNA levels (see FIG. 11). Relative levels of target transcript did not change significantly between cells harboring s1 grown in the absence and high levels of theophylline indicating that antiswitches function through translational inhibition rather than affecting target RNA levels. In addition, the steady-state relative level of s1 was approximately 1,000-fold that of target levels although both antiswitch and target were expressed from the same promoter. This indicates that antiswitch molecules may have higher intracellular stabilities than mRNA potentially due to stabilizing secondary structures or are synthesized more efficiently. The temporal response of antiswitch regulation was determined by inducing antiswitch activation by the addition of theophylline to cells expressing steady-state levels of GFP and s1 in the 'off' state (FIG. 1d). GFP levels began decreasing shortly after the addition of theophylline at a rate corresponding to a half-life of approximately 0.5 to 1 hour, which is consistent with the half-life of the GFP variant used in these experiments (Mateus et al., *Yeast* 16, 1313-23 (2000)). This data supports that antiswitch molecules act rapidly to inhibit translation from their target mRNAs in the presence of activating levels of effector and that the time required for target protein levels to decrease is determined by the protein's half-life.

Figure 1E:
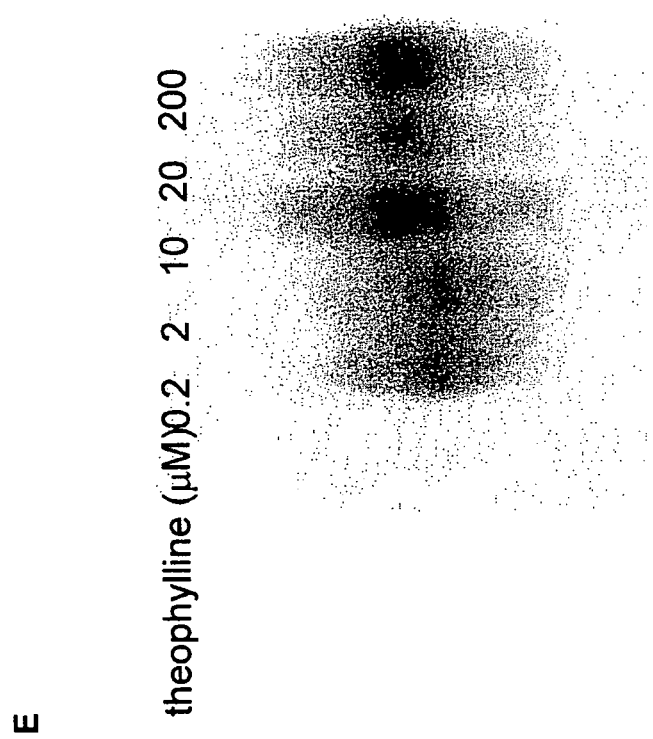
Figure 7:
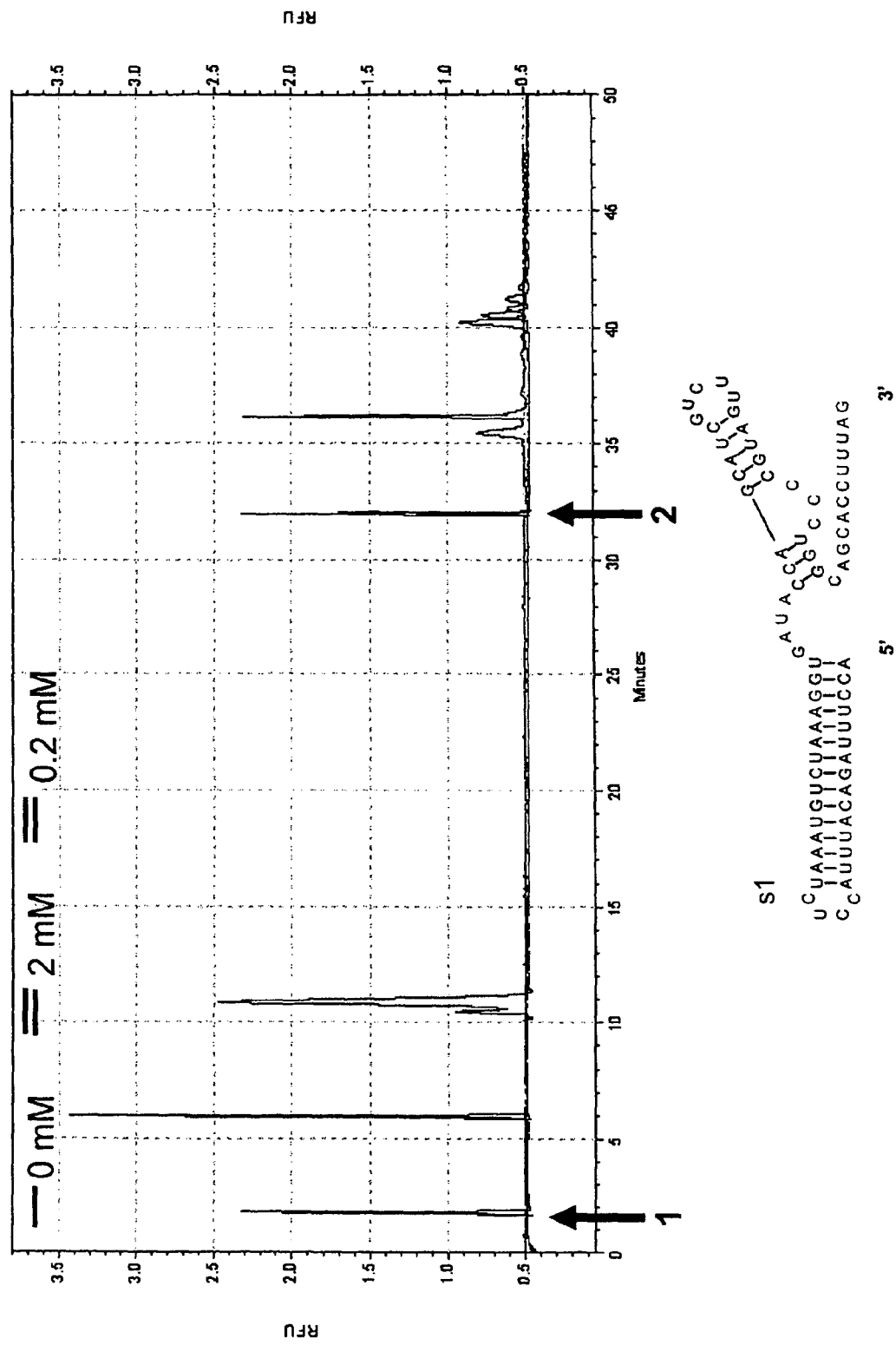
FIG. 7 shows structural probing of antiswitch s1 (SEQ ID NO: 1) through nuclease mapping. Samples correspond to s1 incubated in the presence of varying concentrations of theophylline and RNase T1. RNase T1 cleaves 3' of single-stranded G's. Peak 1 corresponds to the antisense domain and peak 2 corresponds to the switching aptamer stem. In both the absence of theophylline and 200 μM theophylline, the switching aptamer stem is cleaved (peak 2) indicating that this domain is in a single-stranded form, accessible to the nuclease. In 2 mM theophylline this peak is absent indicating that the aptamer stem is protected in a double-stranded stem. Furthermore, in 2 mM theophylline the disappearance of peak 2 occurs simultaneously with the appearance of peak 1 indicating that the antisense domain is in a single-stranded form accessible to the nuclease. This peak is not present in lower levels of theophylline supporting a change in accessibility of this region of the antiswitch under these concentrations.

In vitro characterization studies were conducted to examine antiswitch ligand affinity and conformational changes associated with antiswitch response. Gel shift experiments were conducted in the presence of equimolar amounts of a short target transcript (200 nucleotides), containing regions upstream and downstream of the start codon, and labeled s1 and varying concentrations of theophylline to examine antiswitch ligand affinity (FIG. 1e). A sharp shift in antiswitch mobility is detected between 2 and 10 µM theophylline, presumably due to binding of both theophylline and target. Nuclease mapping in the presence of ligand alone was also conducted to investigate antiswitch conformational changes (see FIG. 7). This data supports that antiswitch molecules exhibit conformational changes at much higher concentrations of ligand than in the presence of ligand and target (between 200 µM and 2 mM versus 2 µM and 10 µM), supporting the cooperative effects of ligand and target on antiswitch conformational dynamics. The in vivo data report the concentration of effector molecule in the media and it is anticipated that the intracellular concentration of these molecules will be much lower due to transport limitations across the membrane. One study reported over a 1,000-fold drop in theophylline concentration across the *E. coli* membrane (Koch, *J Biol Chem* 219, 181-8 (1956)). The in vitro experiments indicate that ligand binding and structural switching occur over narrow concentration ranges, much lower than the extracellular concentrations reported in the in vivo studies. This data indicates that in the presence of target in vitro antiswitch conformational changes display a sharp binary response to ligand concentrations in the low micromolar range which is probably indicative of the intracellular concentrations of theophylline in these studies.

Forward Engineering for Tuning Switching Dynamics

Figure 2A:
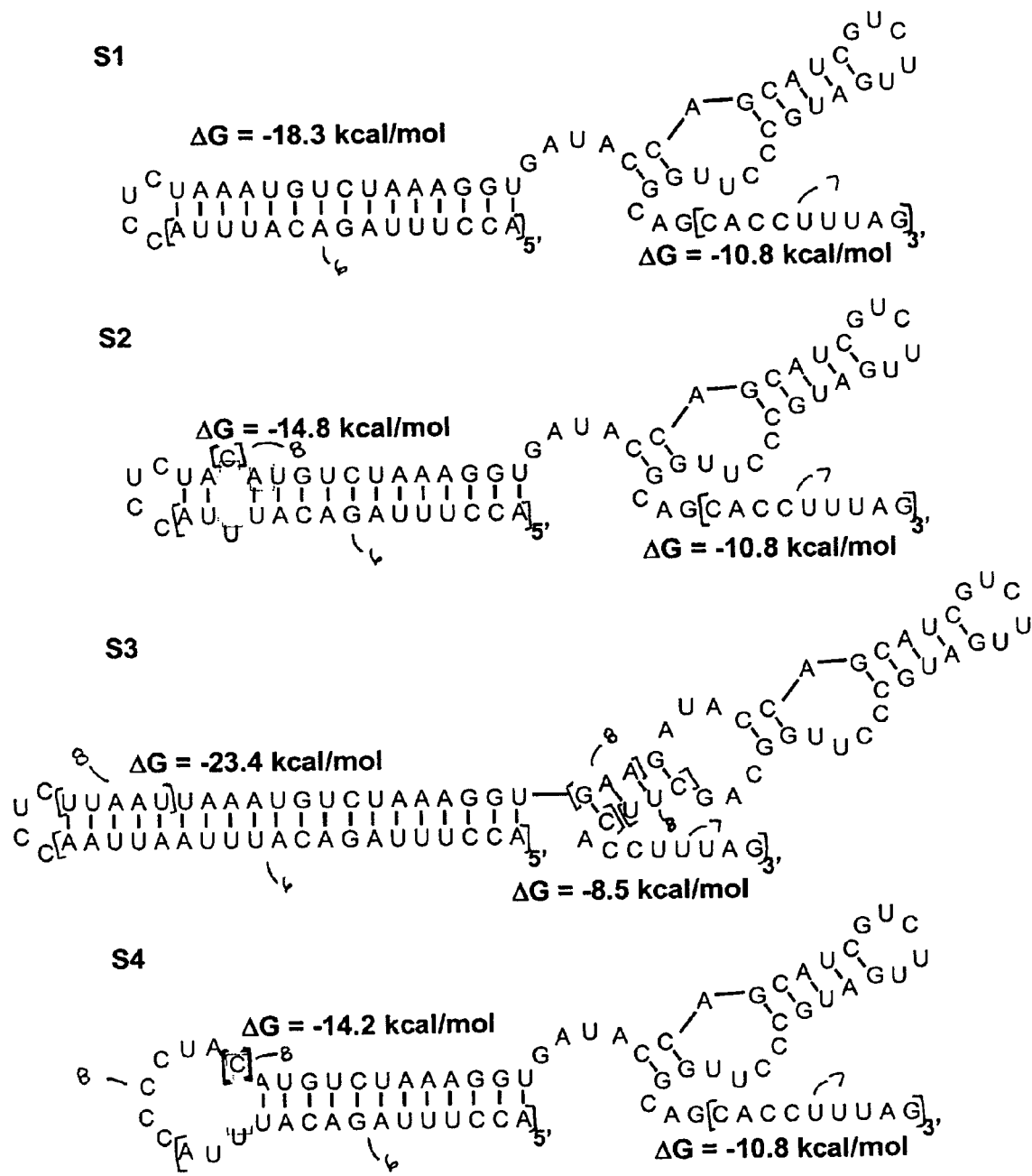
FIGS. 2a and 2b show tuning of the switch response of an antiswitch regulator.

The switching behavior of the antiswitch platform is dependent on conformational dynamics of the RNA structures; therefore it is possible to tune switching behavior in a straightforward manner by altering thermodynamic properties of the antiswitch. It is anticipated that the absolute and relative stabilities of the antisense stem and the aptamer stem will be important design parameters in tuning the switch behavior of an antiswitch. To explore the dynamic range of switch behavior, we created several antiswitches (s2-s4) with varying antisense and aptamer stem stabilities (FIG. 2a). It was anticipated that these altered antiswitches would expand the concentration range over which the switch in gene expression was observed and increase the dynamic range of GFP expression.

Figure 2B:
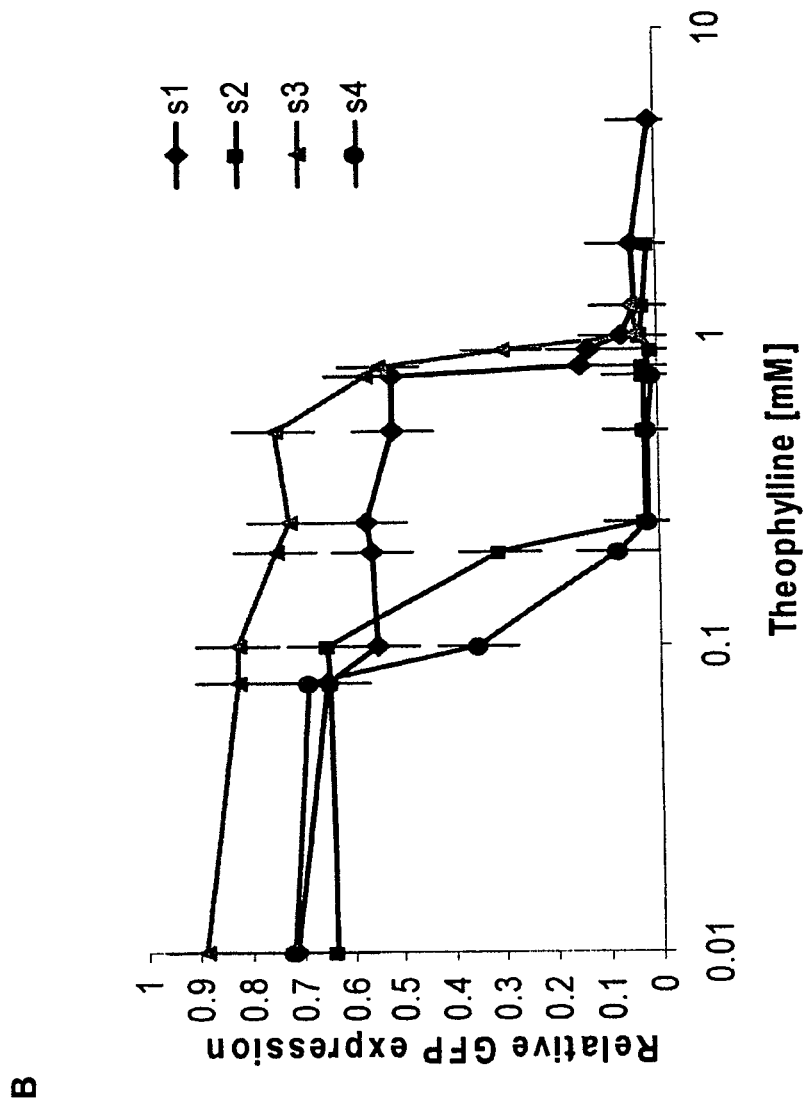

In general, it was observed that increasing antisense stem stability by the addition of base pairs created switches that required higher concentrations of theophylline to affect a switch, whereas decreasing stem stabilities created switches that inhibit GFP expression at lower theophylline concentrations. For example, antiswitch s2 differs from antiswitch s1 by a single nucleotide (A21 to C) (FIG. 2a). This mutation introduces a mismatched pair in the antisense stem so that in the absence of ligand the construct is less thermodynamically stable. As a result, s2 exhibits altered switching dynamics, theophylline concentrations greater than 0.2 mM inhibit gene expression, compared to 0.8 mM for construct s1 (FIG. 2b). Alternately, increasing the stability of the antisense stem creates a switch that requires higher concentrations of theophylline to inhibit expression. Antiswitch s3 is designed with an antisense stem five nucleotides longer than s1 and an aptamer stem with three base pairs of the lower stem formed, increasing the absolute stem stabilities. As a result of this increased stability, s3 switches from GFP expression to inhibition of GFP at approximately 1.25 mM theophylline (FIG. 2b), roughly 1.5-fold the concentration required to switch s1 and 6-fold that required to switch s2. Furthermore, s3 exhibits higher levels of GFP expression in the "off" state, 10% versus 30% inhibition from full expression. Antiswitch s4 was constructed to examine the effects of further destabilizing the antisense stem. This antiswitch includes an altered loop sequence (U18 to C) which further destabilizes the antisense stem from s2. Assays indicate that s4 further expands the dynamic switching behavior of the antiswitch construct, exhibiting switching at 0.1 mM theophylline (FIG. 2b).

Modular Platform Enables Distinct Domain Assembly.

Figure 3A:
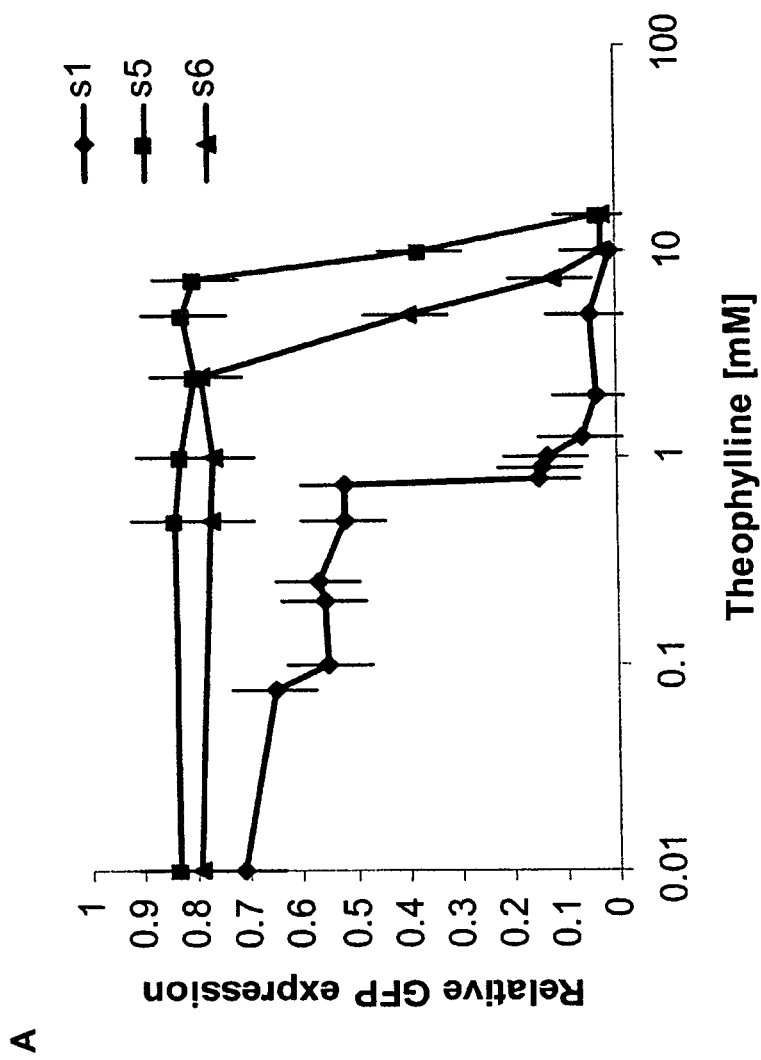
FIGS. 3a and 3b show the expanding of antiswitch properties by swapping modular domains into the design platform.
Figure 3B:
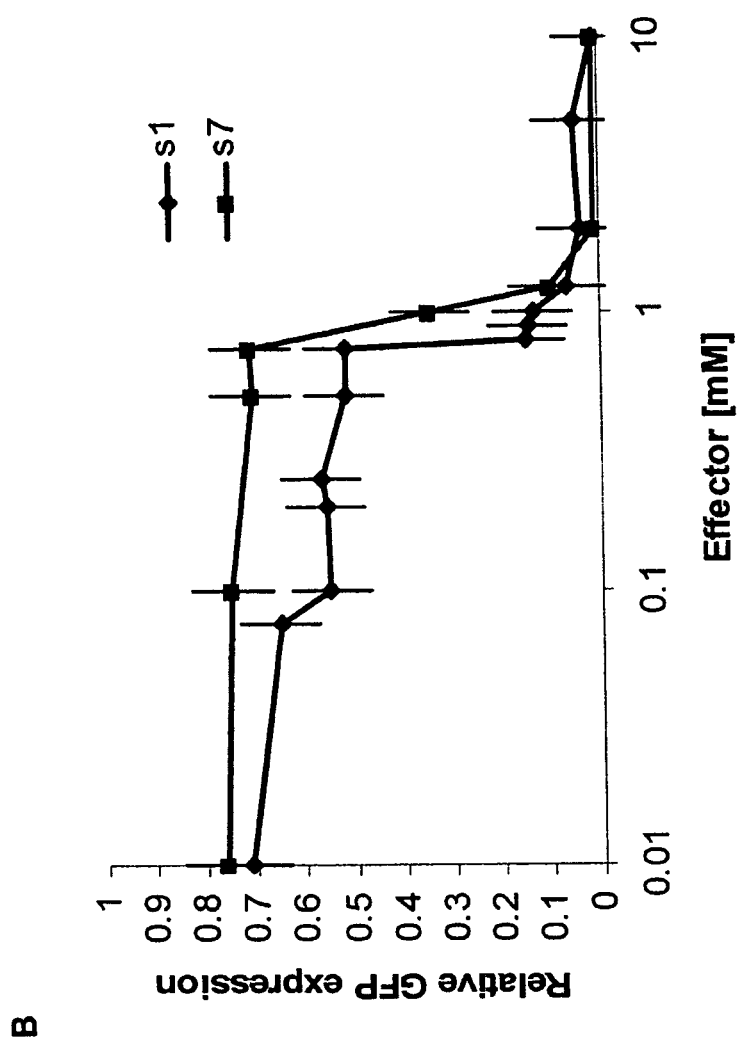

To demonstrate the modularity of the antiswitch design platform, several different antiswitch molecules were constructed and characterized by swapping in different aptamer domains (see FIG. 8). These changes in the aptamer domain were designed to keep the antisense stem and the switching aptamer stem identical to previous designs since the target transcript was kept the same, while swapping out the remainder of the aptamer module. To further explore the range of ligand responsiveness in designed antiswitches, we constructed a switch s5 employing a previously characterized aptamer exhibiting lower affinity to theophylline (Zimmermann et al., *RNA* 6, 659-67 (2000)). This aptamer has a $K_d$ approximately ten-fold higher than the aptamer used in s1-s4. In addition, the response of this antiswitch was tuned by destabilizing the antisense stem in a manner identical to s2, creating s6. To further test the modularity of this platform, an antiswitch was also constructed with a previously characterized aptamer to tetracycline (Berens et al., *Bioorg Med Chem* 9, 2549-56 (2001)). This aptamer has an affinity to tetracycline similar to that of the theophylline aptamer used in s1-4 ($K_d$=1 µM). The data in FIGS. 3a-3b support the modularity of the antiswitch platform to different aptamer domains. The modified theophylline aptamers exhibit an altered response to ligand concentrations from s1-4. As expected, the switching for s5 and s6 occurs at higher theophylline concentrations (FIG. 3a). Significantly, s5, which contains an aptamer domain with a 10-fold higher Kd than the aptamer domain in s1, switches at approximately a 10-fold higher theophylline concentration. In addition, the tetracycline antiswitch s7 shows similar switch dynamics as s1-4, suggesting that the response curve observed is a general feature of designed antiswitches (FIG. 3b).

Design and Characterization of an "on" Switch

Figure 4A:
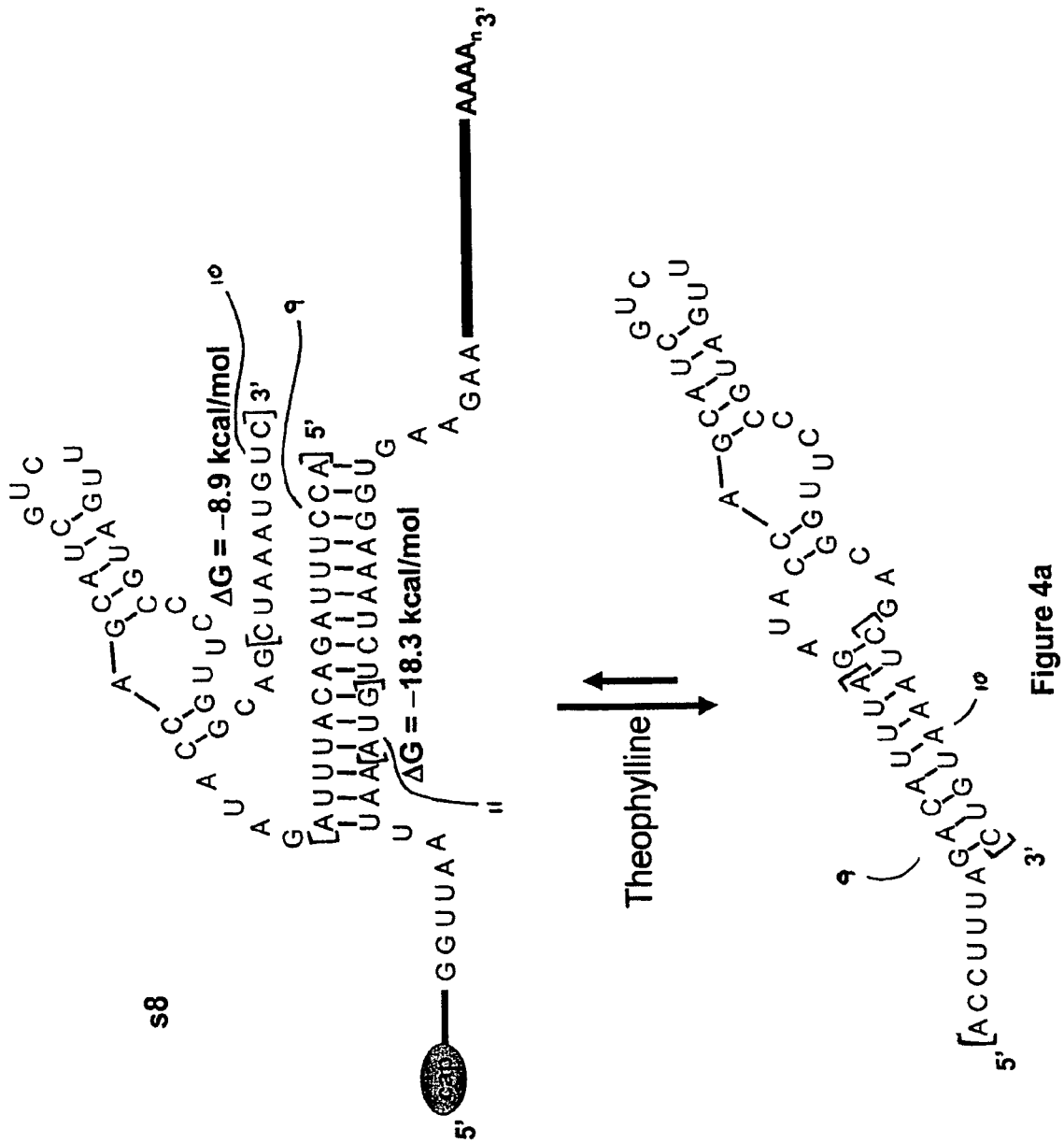
FIGS. 4a and 4b show the redesign and characterization of a novel "on" antiswitch regulator.
Figure 4B:
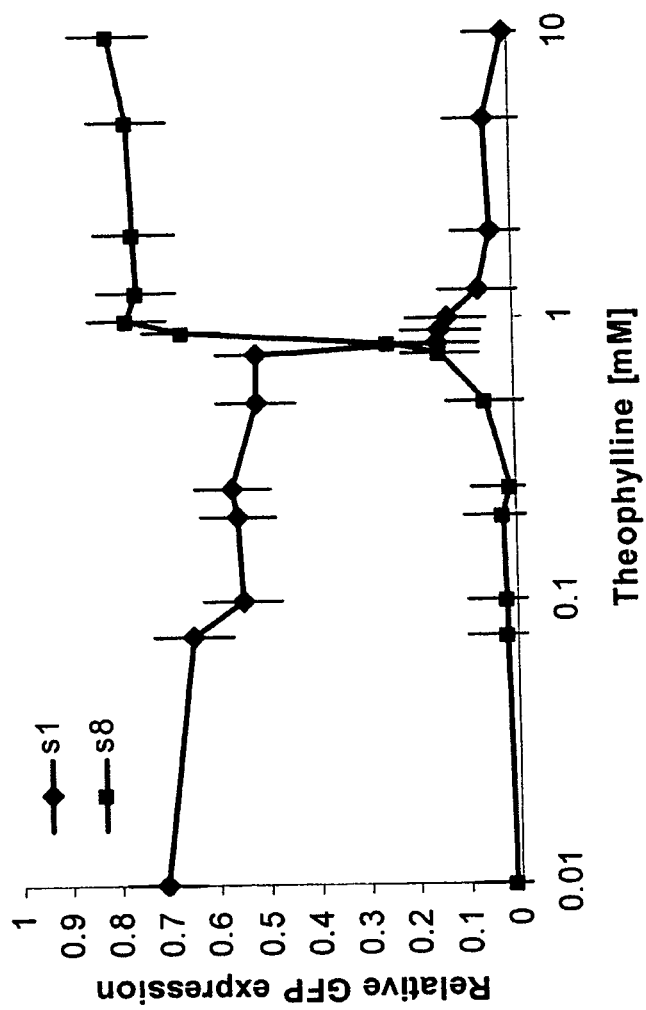

To further examine the flexibility of the antiswitch platform we redesigned the platform in an attempt to construct an "on" antiswitch from the aptamer and antisense domains used in the design of s1. An antiswitch s8 that inhibits expression in the absence of theophylline, but allows expression in the presence of theophylline was constructed using similar design principles. This switch displays its antisense domain in the absence of ligand, leaving it free to interact with the target mRNA, while sequestering the antisense in the aptamer stem when ligand is present (FIG. 4a). s8 displays similar dynamic behavior to s1 (switching around 1 mM theophylline), as is expected due to similar base pairing energetics (FIG. 4b). This functional "on" switch demonstrates the flexibility of the antiswitch platform and the generality of the design themes.

Simultaneous, Combinatorial Gene Regulation

Figure 5A:
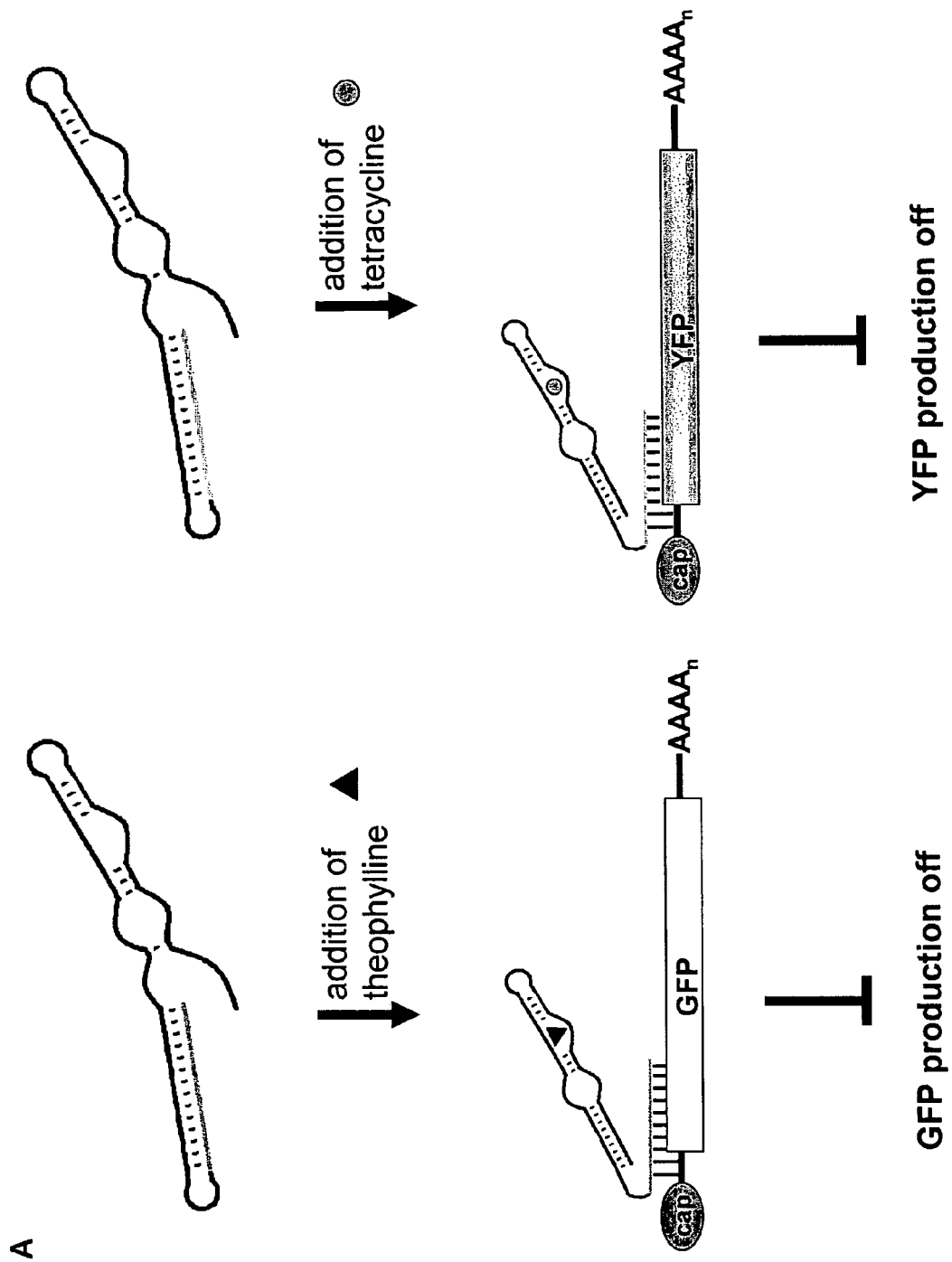
FIGS. 5a and 5b show simultaneous regulation of multiple genes through multiple antiswitch regulators.
Figure 5B:
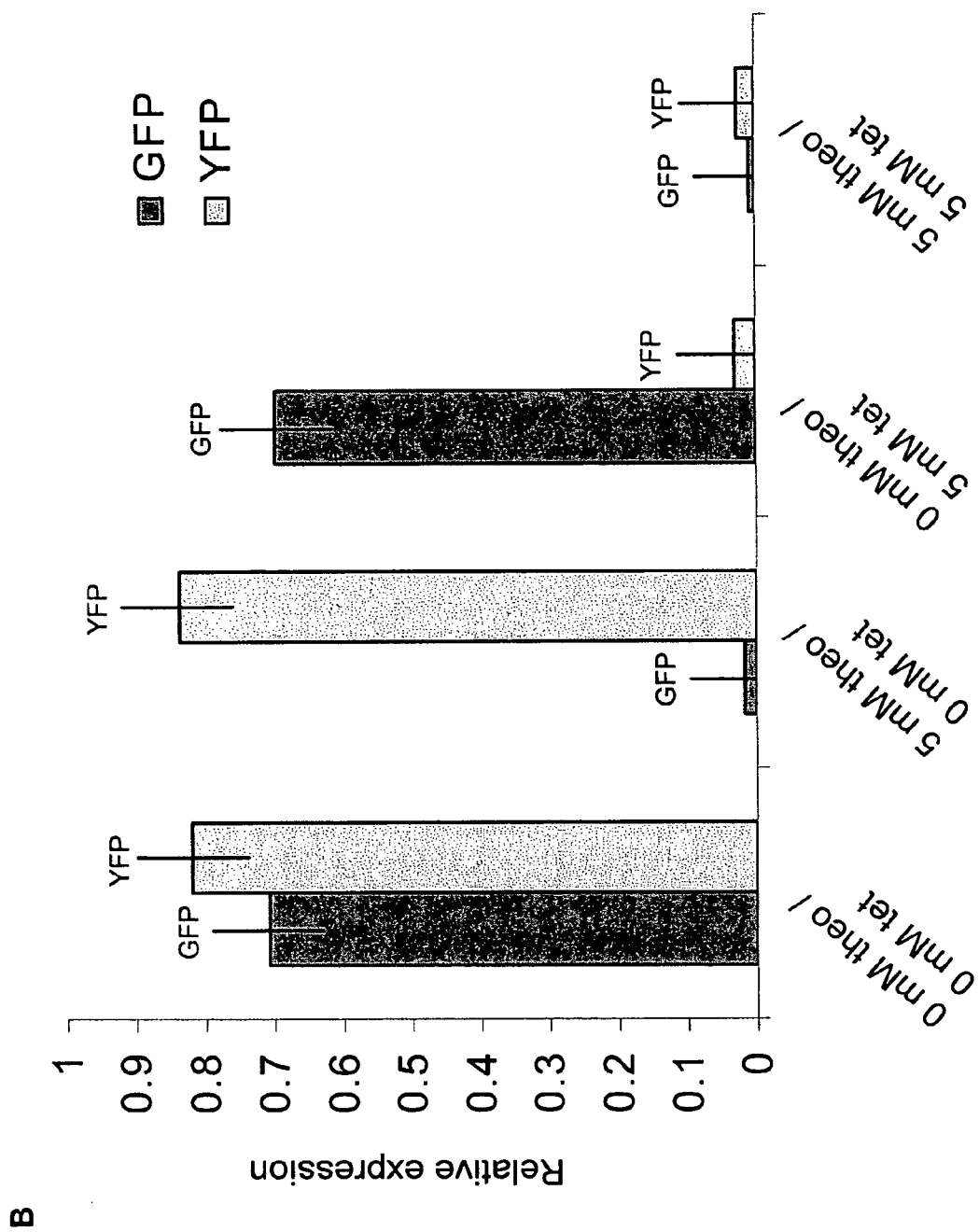
Figure 9:
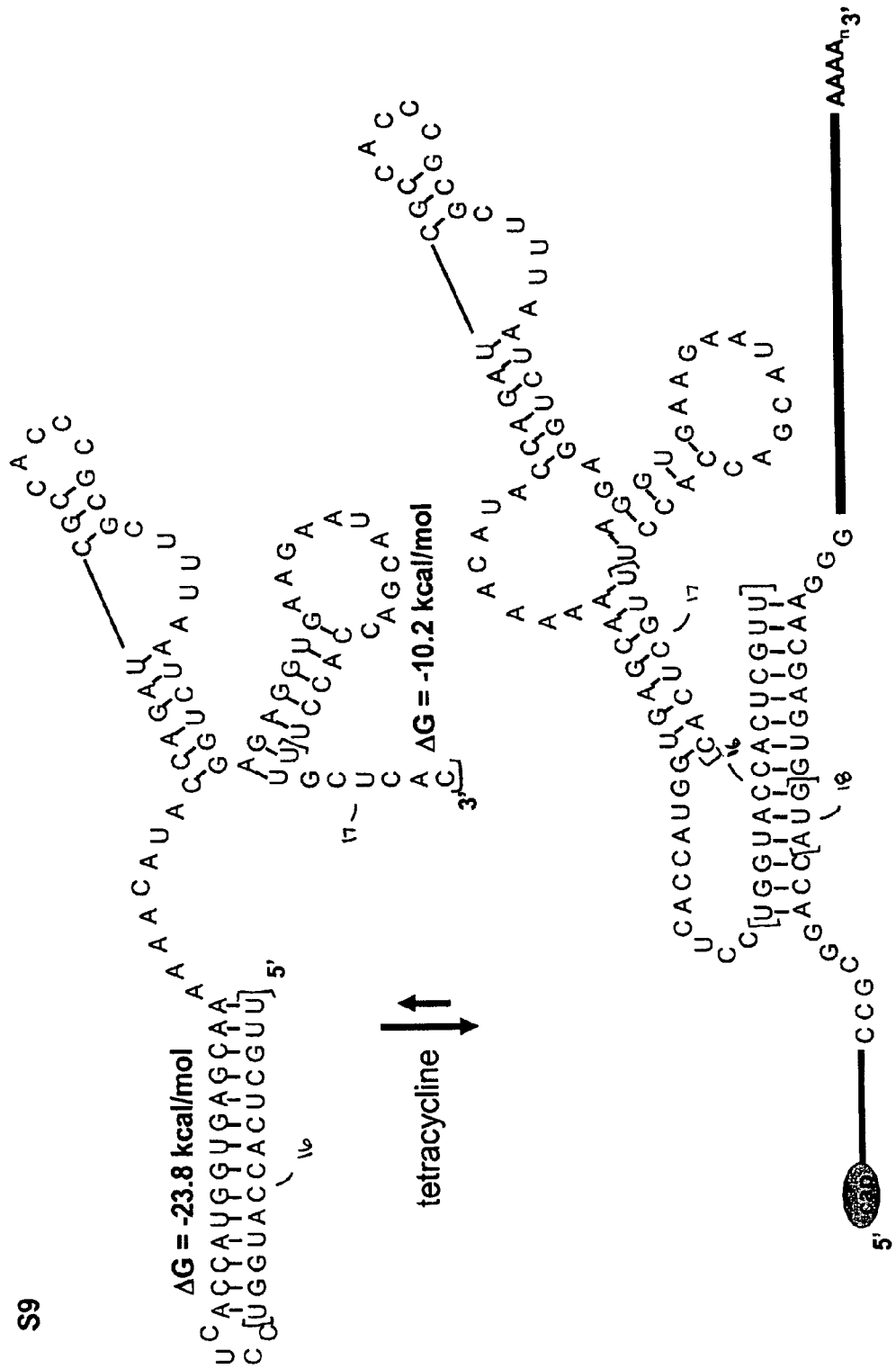
FIG. 9 shows the sequence and structural switching of a tetracycline-responsive Venus (YFP) regulator, s9 (SEQ ID NO: 9), and its target mRNA (SEQ ID NO: 19). 16, antisense sequence; 17, switching aptamer stem sequence; 18, the start codon on the target mRNA. The stability of each stem is indicated.

The modular nature of the antiswitch platform allows for systems exhibiting combinatorial control over gene expression. To illustrate this we introduced into cells two switches each responsive to a different effector molecule and each regulating the protein expression of a different mRNA target: s1, a theophylline responsive GFP regulator, and s9 (see FIG. 9), a tetracycline responsive yellow fluorescent variant protein (Venus) (Nagai et al., Nat Biotechnol 20, 87-90 (2002)) regulator (FIG. 5a). Changes in the targeting capabilities of these molecules were made by swapping out the antisense stem and switching aptamer stem while keeping the remainder of the aptamer module the same. Concurrent expression of these two antiswitches with a plasmid carrying both GFP and Venus allowed for an assay of the simultaneous regulation of gene expression by modular antiswitch design. As shown in FIG. 5b, addition of theophylline decreased expression of GFP while Venus expression remained unaffected, and addition of tetracycline decreased Venus while not affecting GFP. Furthermore, the addition of both ligands decreased expression of both GFP and Venus. This simple system illustrates the potential of building more complex genetic circuits that are precisely regulated by multiple antiswitch constructs.

REFERENCES

1. Banerjee, D. & Slack, F. Control of developmental timing by small temporal RNAs: a paradigm for RNA-mediated regulation of gene expression. Bioessays 24, 119-29 (2002).
2. Kramer, C., Loros, J. J., Dunlap, J. C. & Crosthwaite, S. K. Role for antisense RNA in regulating circadian clock function in Neurospora crassa. Nature 421, 948-52 (2003).
3. Good, L. Diverse antisense mechanisms and applications. Cell Mol Life Sci 60, 823-4 (2003).
4. Good, L. Translation repression by antisense sequences. Cell Mol Life Sci 60, 854-61 (2003).
5. Vacek, M., Sazani, P. & Kole, R. Antisense-mediated redirection of mRNA splicing. Cell Mol Life Sci 60, 825-33 (2003).
6. Bartel, D. P. MicroRNAs: genomics, biogenesis, mechanism, and function. Cell 116, 281-97 (2004).
7. Scherer, L. & Rossi, J. J. Recent applications of RNAi in mammalian systems. Curr Pharm Biotechnol 5, 355-60 (2004).
8. Lilley, D. M. The origins of RNA catalysis in ribozymes. Trends Biochem Sci 28, 495-501 (2003).
9. Mandal, M. & Breaker, R. R. Adenine riboswitches and gene activation by disruption of a transcription terminator. Nat Struct Mol Biol 11, 29-35 (2004).
10. Winkler, W., Nahvi, A. & Breaker, R. R. Thiamine derivatives bind messenger RNAs directly to regulate bacterial gene expression. Nature 419, 952-6 (2002).
11. Winkler, W. C., Nahvi, A., Roth, A., Collins, J. A. & Breaker, R. R. Control of gene expression by a natural metabolite-responsive ribozyme. Nature 428, 281-6 (2004).
12. Barrick, J. E. et al. New RNA motifs suggest an expanded scope for riboswitches in bacterial genetic control. Proc Natl Acad Sci USA 101, 6421-6 (2004).
13. Yelin, R. et al. Widespread occurrence of antisense transcription in the human genome. Nat Biotechnol 21, 379-86 (2003).
14. Lavorgna, G. et al. In search of antisense. Trends Biochem Sci 29, 88-94 (2004).
15. Ellington, A. D. & Szostak, J. W. In vitro selection of RNA molecules that bind specific ligands. Nature 346, 818-22 (1990).
16. Tuerk, C. & Gold, L. Systematic evolution of ligands by exponential enrichment: RNA ligands to bacteriophage T4 DNA polymerase. Science 249, 505-10 (1990).
17. Hermann, T. & Patel, D. J. Adaptive recognition by nucleic acid aptamers. Science 287, 820-5 (2000).
18. Cox, J. C. et al. Automated selection of aptamers against protein targets translated in vitro: from gene to aptamer. Nucleic Acids Res 30, e108 (2002).
19. Jhaveri, S., Rajendran, M. & Ellington, A. D. In vitro selection of signaling aptamers. Nat Biotechnol 18, 1293-7 (2000).
20. Roth, A. & Breaker, R. R. Selection in vitro of allosteric ribozymes. Methods Mol Biol 252, 145-64 (2004).
21. Stojanovic, M. N. & Kolpashchikov, D. M. Modular aptameric sensors. J Am Chem Soc 126, 9266-70 (2004).
22. Smolke, C. D., Carrier, T. A. & Keasling, J. D. Coordinated, differential expression of two genes through directed mRNA cleavage and stabilization by secondary structures. Appl Environ Microbiol 66, 5399-405 (2000).
23. Isaacs, F. J. et al. Engineered riboregulators enable post-transcriptional control of gene expression. Nat Biotechnol 22, 841-7 (2004).
24. Yen, L. et al. Exogenous control of mammalian gene expression through modulation of RNA self-cleavage. Nature 431, 471-6 (2004).
25. Buskirk, A. R., Landrigan, A. & Liu, D. R. Engineering a ligand-dependent RNA transcriptional activator. Chem Biol 11, 1157-63 (2004).
26. Weiss, B., Davidkova, G. & Zhou, L. W. Antisense RNA gene therapy for studying and modulating biological processes. Cell Mol Life Sci 55, 334-58 (1999).
27. Scherer, L. J. & Rossi, J. J. Approaches for the sequence-specific knockdown of mRNA. Nat Biotechnol 21, 1457-65 (2003).
28. Nutiu, R. & Li, Y. Structure-switching signaling aptamers. J Am Chem Soc 125, 4771-8 (2003).

29. Zimmermann, G. R., Wick, C. L., Shields, T. P., Jenison, R. D. & Pardi, A. Molecular interactions and metal binding in the theophylline-binding core of an RNA aptamer. RNA 6, 659-67 (2000).
30. Zimmermann, G. R., Jenison, R. D., Wick, C. L., Simorre, J. P. & Pardi, A. Interlocking structural motifs mediate molecular discrimination by a theophylline-binding RNA. Nat Struct Biol 4, 644-9 (1997).
31. Gouda, H., Kuntz, I. D., Case, D. A. & Kollman, P. A. Free energy calculations for theophylline binding to an RNA aptamer: Comparison of MM-PBSA and thermodynamic integration methods. Biopolymers 68, 16-34 (2003).
32. Mathews, D. H. et al. Incorporating chemical modification constraints into a dynamic programming algorithm for prediction of RNA secondary structure. Proc Natl Acad Sci USA 101, 7287-92 (2004).
33. Taira, K., Nakagawa, K., Nishikawa, S. & Furukawa, K. Construction of a novel RNA-transcript-trimming plasmid which can be used both in vitro in place of run-off and (G)-free transcriptions and in vivo as multi-sequences transcription vectors. Nucleic Acids Res 19, 5125-30 (1991).
34. Samarsky, D. A. et al. A small nucleolar RNA:ribozyme hybrid cleaves a nucleolar RNA target in vivo with near-perfect efficiency. Proc Natl Acad Sci USA 96, 6609-14 (1999).
35. Mateus, C. & Avery, S. V. Destabilized green fluorescent protein for monitoring dynamic changes in yeast gene expression with flow cytometry. Yeast 16, 1313-23 (2000).
36. Koch, A. L. The metabolism of methylpurines by *Escherichia coli*. I. Tracer studies. J Biol Chem 219, 181-8 (1956).
37. Berens, C., Thain, A. & Schroeder, R. A tetracycline-binding RNA aptamer. Bioorg Med Chem 9, 2549-56 (2001).
38. Nagai, T. et al. A variant of yellow fluorescent protein with fast and efficient maturation for cell-biological applications. Nat Biotechnol 20, 87-90 (2002).
39. Watkins, S. M. & German, J. B. Metabolomics and biochemical profiling in drug discovery and development. Curr Opin Mol Ther 4, 224-8 (2002).
40. Khosla, C. & Keasling, J. D. Metabolic engineering for drug discovery and development. Nat Rev Drug Discov 2, 1019-25 (2003).
41. Kobayashi, H. et al. Programmable cells: interfacing natural and engineered gene networks. Proc Natl Acad Sci USA 101, 8414-9 (2004).
42. Sambrook, J. & Russell, D. W. Molecular cloning: A laboratory manual (Cold Spring Harbor Laboratory Press, Cold Spring Harbor, N.Y., 2001).
43. Sikorski, R. S. & Hieter, P. A system of shuttle vectors and yeast host strains designed for efficient manipulation of DNA in Saccharomyces cerevisiae. Genetics 122, 19-27 (1989).
44. Gietz, R. & Woods, R. in Guide to Yeast Genetics and Molecular and Cell Biology, Part B (eds. Guthrie, C. & Fink, G.) 87-96 (Academic Press, San Diego, 2002).
45. Caponigro, G., Muhlrad, D. & Parker, R. A small segment of the MAT alpha 1 transcript promotes mRNA decay in Saccharomyces cerevisiae: a stimulatory role for rare codons. Mol Cell Biol 13, 5141-8 (1993).

OTHER RELATED REFERENCES INCLUDE

Hesselberth J R et al. 2003. Simultaneous detection of diverse analytes with an aptazyme ligase array. Anal. Biochem. 312:106-112.
Kertsburg A, Soukup G A. 2002. A versatile communication module for controlling RNA folding and catalysis. Nucleic Acids Res. 30:4599-606.
Wang D Y, Lai B H, Sen D. 2002. A general strategy for effector-mediated control of RNA-cleaving ribozymes and DNA enzymes. J. Mol. Biol. 318:33-43.
Wang D Y et al. 2002. A general approach for the use of oligonucleotide effectors to regulate the catalysis of RNA-cleaving ribozymes and DNAzymes. Nucleic Acids Res. 30:1735-42.
Piganeau N et al. 2001. In vitro selection of allosteric ribozymes: theory and experimental validation. J. Mol. Biol. 315:1177-90.
Kuwabara T et al. 2001. Allosterically controlled single-chained maxizymes with extremely high and specific activity. Biomacromolecules. 2:788-99.
Kuwabara T et al. 2001. Allosterically controllable maxizyme-mediated suppression of progression of leukemia in mice. Biomacromolecules. 2:1220-8.
Soukup G A et al. 2001. Generating new ligand-binding RNAs by affinity maturation and disintegration of allosteric ribozymes. RNA. 7:524-36.
Jose A M et al. 2001. Cooperative binding of effectors by an allosteric ribozyme. Nucleic Acids Res. 29:1631-7.
Kuwabara T et al. 2000. Allosterically controllable ribozymes with biosensor functions. Curr. Opin. Chem. Biol. 4:669-77.
Soukup G A et al. 2000. Altering molecular recognition of RNA aptamers by allosteric selection. J. Mol. Biol. 298:623-32.
Robertson M P, Ellington A D. 2000. Design and optimization of effector-activated ribozyme ligases. Nucleic Acids Res. 28:1751-9.
Koizumi M et al. 1999. Allosteric selection of ribozymes that respond to the second messengers cGMP and cAMP. Nat. Struct. Biol. 6:1062-71.
Soukup G A, Breaker R R. 1999. Design of allosteric hammerhead ribozymes activated by ligand-induced structure stabilization. Structure Fold Des. 7:783-91.
Tang J, Breaker R R. 1997. Rational design of allosteric ribozymes. Chem. Biol. 4:453-9.
Bayer T S and Smolke C D. 2005. Programmable ligand-controlled riboregulators of eukaryotic gene expression. 23(3):337-43.

All references cited herein are hereby incorporated by reference in their entirety.

We claim:

1. A nucleic acid comprising (i) a substrate sequence that can form a hairpin RNA stem as a substrate for an RNaseIII family nuclease, and (ii) an aptamer that binds to a ligand, wherein said aptamer comprises a sequence that can form an aptamer stem, the formation of said aptamer stem competes with the formation of said hairpin RNA stem, wherein binding of the ligand to said aptamer causes a conformational change to render the substrate sequence non-functional by destabilizing the hairpin RNA stem, through stabilizing the aptamer stem, and, wherein said RNaseIII family nuclease processes said hairpin RNA through an RNA interference (RNAi) mechanism in attenuating expression of a target gene.

2. The nucleic acid of claim 1, wherein said nucleic acid is a ribonucleic acid (RNA).

3. The nucleic acid of claim 1, wherein said RNaseIII family nuclease processes said hairpin RNA to produce siRNA.

4. The nucleic acid of claim 1, wherein the ligand is a small molecule having a molecular weight less than 2500 amu.

5. The nucleic acid of claim 1, wherein the ligand is a metal ion.

6. The nucleic acid of claim 1, wherein the ligand is a polypeptide, a peptide, a nucleic acid, a carbohydrate, a fatty acid, a lipid, a non-peptide hormone, or a metabolic precursor or product thereof.

7. The nucleic acid of claim 1, wherein the ligand is selected from enzyme co-factors, enzyme substrates and products of enzyme-mediated reactions.

8. An expression construct comprising (i) a coding sequence which, when transcribed, produces the RNA of claim 2, and (ii) one or more transcriptional regulatory sequences that regulate transcription of said RNA in a cell containing said expression construct.

9. A library of aptamer-regulated nucleic acids, each independently comprising the nucleic acid of claim 1, or an expression construction encoding said nucleic acid.

10. A recombinant cell engineered with the expression construct of claim 9.

11. A cell comprising the nucleic acid of claim 1.

12. The nucleic acid of claim 1, wherein said RNaseIII family nuclease is Dicer.

13. The nucleic acid of claim 3, wherein said siRNA is between about 19 and about 30 nucleotides in length.

14. The nucleic acid of claim 3, wherein said siRNA is between about 21 and about 23 nucleotides in length.

15. The nucleic acid of claim 1, wherein said nucleic acid further comprises an intercalator or an alkylating agent.

16. The nucleic acid of claim 1, wherein said aptamer is responsive to pH, temperature, or salt concentration.

17. The nucleic acid of claim 1, wherein said aptamer of said nucleic acid is altered so that the $K_d$ for binding of a ligand to the aptamer is higher or lower than the $K_d$ of an unaltered aptamer.

18. The nucleic acid of claim 1, wherein said nucleic acid comprises one or more said aptamers or one or more said substrate sequences.

19. The nucleic acid of claim 1, wherein said nucleic acid interacts with and responds to multiple ligands.

20. The nucleic acid of claim 1, wherein said nucleic acid is a cooperative ligand controlled nucleic acid wherein multiple ligands sequentially bind to multiple aptamer domains to allosterically regulate an effector domain.

* * * * *

SEQUENCE LISTING

<160> NUMBER OF SEQ ID NOS: 24

<210> SEQ ID NO 1
<211> LENGTH: 74
<212> TYPE: RNA
<213> ORGANISM: Artificial Sequence
<220> FEATURE:
<223> OTHER INFORMATION: Description of Artificial Sequence: Synthetic -continued antiswitch s1 oligonucleotide

<400> SEQUENCE: 1
accuuuagac auuuaccucu aaaugucuaa aggugauacc agcaucgucu ugaugcccuu    60
ggcagcaccu uuag                                                      74

<210> SEQ ID NO 2
<211> LENGTH: 74
<212> TYPE: RNA
<213> ORGANISM: Artificial Sequence
<220> FEATURE:
<223> OTHER INFORMATION: Description of Artificial Sequence: Synthetic
      antiswitch s2 oligonucleotide

<400> SEQUENCE: 2
accuuuagac auuuaccucu acaugucuaa aggugauacc agcaucgucu ugaugcccuu    60
ggcagcaccu uuag                                                      74

<210> SEQ ID NO 3
<211> LENGTH: 90
<212> TYPE: RNA
<213> ORGANISM: Artificial Sequence
<220> FEATURE:
<223> OTHER INFORMATION: Description of Artificial Sequence: Synthetic
      antiswitch s3 oligonucleotide

<400> SEQUENCE: 3
accuuuagac auuaauuaa ccucuuaauu aaaugucuaa aggugaagau accagcaucg     60
ucuugaugcc cuuggcagcu ucaccuuuag                                     90

<210> SEQ ID NO 4
<211> LENGTH: 74
<212> TYPE: RNA
<213> ORGANISM: Artificial Sequence
<220> FEATURE:
<223> OTHER INFORMATION: Description of Artificial Sequence: Synthetic
      antiswitch s4 oligonucleotide

<400> SEQUENCE: 4
accuuuagac auuuacccu acaugucuaa aggugauacc agcaucgucu ugaugcccuu     60
ggcagcaccu uuag                                                      74

<210> SEQ ID NO 5
<211> LENGTH: 69
<212> TYPE: RNA
<213> ORGANISM: Artificial Sequence
<220> FEATURE:
<223> OTHER INFORMATION: Description of Artificial Sequence: Synthetic
      antiswitch s5 oligonucleotide

<400> SEQUENCE: 5
accuuuagac auuuaccucu aaaugucuaa aggugauacc acgcgaaagc gccuuggcag    60
caccuuuag                                                            69

<210> SEQ ID NO 6
<211> LENGTH: 69
<212> TYPE: RNA
<213> ORGANISM: Artificial Sequence
<220> FEATURE:
<223> OTHER INFORMATION: Description of Artificial Sequence: Synthetic
      antiswitch s6 oligonucleotide

<400> SEQUENCE: 6

-continued

<210> SEQ ID NO 7
<211> LENGTH: 101
<212> TYPE: RNA
<213> ORGANISM: Artificial Sequence
<220> FEATURE:
<223> OTHER INFORMATION: Description of Artificial Sequence: Synthetic
      antiswitch s7 oligonucleotide

<400> SEQUENCE: 7
accuuuagac auuuaccucu aaaugucuaa agguaaaaca uaccagaucg ccacccgcgc    60
uuuaaucugg agaggugaag aauacgacca ccuaccuuua g                        101

<210> SEQ ID NO 8
<211> LENGTH: 55
<212> TYPE: RNA
<213> ORGANISM: Artificial Sequence
<220> FEATURE:
<223> OTHER INFORMATION: Description of Artificial Sequence: Synthetic
      antiswitch s8 oligonucleotide

<400> SEQUENCE: 8
accuuuagac auuagauac cagcaucguc uugaugcccu uggcagcuaa auguc          55

<210> SEQ ID NO 9
<211> LENGTH: 99
<212> TYPE: RNA
<213> ORGANISM: Artificial Sequence
<220> FEATURE:
<223> OTHER INFORMATION: Description of Artificial Sequence: Synthetic
      antiswitch s9 oligonucleotide

<400> SEQUENCE: 9
uugcucacca ugguccucac cauggugagc aaaaaacaua ccagaucgcc acccgcgcuu    60
uaaucuggag aggugaagaa uacgaccacc uuugcucac                           99

<210> SEQ ID NO 10
<211> LENGTH: 15
<212> TYPE: RNA
<213> ORGANISM: Artificial Sequence
<220> FEATURE:
<223> OTHER INFORMATION: Description of Artificial Sequence: Synthetic
      GFP antisense oligonucleotide

<400> SEQUENCE: 10
accuuuagac auuua                                                     15

<210> SEQ ID NO 11
<211> LENGTH: 40
<212> TYPE: RNA
<213> ORGANISM: Artificial Sequence
<220> FEATURE:
<223> OTHER INFORMATION: Description of Artificial Sequence: Synthetic
      theophyllin e aptamer

<400> SEQUENCE: 11
aggugauacc agcaucgucu ugaugcccuu ggcagcaccu                          40

<210> SEQ ID NO 12
<211> LENGTH: 19
<212> TYPE: DNA
<213> ORGANISM: Artificial Sequence
<220> FEATURE:

<223> OTHER INFORMATION: Description of Artificial Sequence: Synthetic
    s1 FWD PCR primer

<400> SEQUENCE: 12
accagacaac ccaaagcaa                                                   19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
    s1 REV PCR primer

<400> SEQUENCE: 13
ctaaaggtgc tgccaaggg                                                   19

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
    s1 FWD PCR primer

<400> SEQUENCE: 14
tagcggatcc aggtctgatg agtccgtgag gacg                                  34

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
    GFP FWD PCR primer

<400> SEQUENCE: 15
attttggttg aattagatgg tga                                              23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
    GFP REV PCR primer

<400> SEQUENCE: 16
ctggcaattt accagtagta caaa                                             24

<210> SEQ ID NO 17
<211> LENGTH: 32
<212> TYPE: RNA
<213> ORGANISM: Artificial Sequence
<220> FEATURE:
<223> OTHER INFORMATION: Description of Artificial Sequence: Synthetic
    s1 or s8 target oligonucleotide

<400> SEQUENCE: 17
gguuaauuaa augucuaaag gugaagaaaa aa                                    32

<210> SEQ ID NO 18
<211> LENGTH: 96
<212> TYPE: RNA
<213> ORGANISM: Artificial Sequence
<220> FEATURE:
<223> OTHER INFORMATION: Description of Artificial Sequence: Synthetic

```
                    ncRNA construct
<220> FEATURE:
<221> NAME/KEY: modified_base
<222> LOCATION: (50)
<223> OTHER INFORMATION: a, u, c, g, unknown or other

<400> SEQUENCE: 18
ggaucccuga ugaguccgug aggacgaaac gguaggaauu ccuaccgucn accggagucg      60
acuccggucu gaugaguccg ugaggacgaa cucgag                               96

<210> SEQ ID NO 19
<211> LENGTH: 27
<212> TYPE: RNA
<213> ORGANISM: Artificial Sequence
<220> FEATURE:
<223> OTHER INFORMATION: Description of Artificial Sequence: Synthetic
      s9 target oligonucleotide

<400> SEQUENCE: 19
ccgcggacca uggugagcaa gggaaaa                                         27

<210> SEQ ID NO 20
<211> LENGTH: 91
<212> TYPE: RNA
<213> ORGANISM: Artificial Sequence
<220> FEATURE:
<223> OTHER INFORMATION: Description of Artificial Sequence: Synthetic
      cooperative switch oligonucleotide

<400> SEQUENCE: 20
gcuacgauac cagcaucguc uugaugcccu uggcagcgua gcuaggaagg uuuagcuaca     60
cuuccauguc uaacacaccu uuagacaugg a                                    91

<210> SEQ ID NO 21
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic cMyc siRNA sense strand oligonucleotide
<220> FEATURE:
<223> OTHER INFORMATION: Description of Artificial Sequence: Synthetic
      cMyc siRNA sense strand oligonucleotide

<400> SEQUENCE: 21
ucccgcgacg augccccuca tt                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic cMyc siRNA antisense strand
      oligonucleotide
<220> FEATURE:
<223> OTHER INFORMATION: Description of Artificial Sequence: Synthetic
      cMyc siRNA antisense strand oligonucleotide

<400> SEQUENCE: 22
ugaggggcau cgucgcggga tt                                              22

<210> SEQ ID NO 23
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic Egr-1 siRNA sense strand
      oligonucleotide
<220> FEATURE:
<223> OTHER INFORMATION: Description of Artificial Sequence: Synthetic
      Egr-1 siRNA sense strand oligonucleotide

<400> SEQUENCE: 23
ucguccagga uggccgcggt t                                               21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic Egr-1 siRNA antisense strand
      oligonucleotide
<220> FEATURE:
<223> OTHER INFORMATION: Description of Artificial Sequence: Synthetic
      Egr-1 siRNA antisense strand oligonucleotide

<400> SEQUENCE: 24
ccgcggccau ccuggacgat t                                               21
```